(12) United States Patent
Ferrari et al.

(10) Patent No.: US 10,058,633 B2
(45) Date of Patent: Aug. 28, 2018

(54) BIODEGRADABLE SCAFFOLDS

(71) Applicants: Mauro Ferrari, Houston, TX (US);
Rachel Buchanan, Austin, TX (US);
Christine Smid, Austin, TX (US);
Ennio Tasciotti, Houston, TX (US)

(72) Inventors: Mauro Ferrari, Houston, TX (US);
Rachel Buchanan, Austin, TX (US);
Christine Smid, Austin, TX (US);
Ennio Tasciotti, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/270,324

(22) Filed: Sep. 20, 2016

(65) Prior Publication Data
US 2017/0136154 A1 May 18, 2017

Related U.S. Application Data

(63) Continuation of application No. 13/809,291, filed as application No. PCT/US2011/029832 on Mar. 24, 2011.
(Continued)

(51) Int. Cl.
*A61L 27/56* (2006.01)
*A61L 27/54* (2006.01)
(Continued)

(52) U.S. Cl.
CPC ............... *A61L 27/56* (2013.01); *A61L 27/16* (2013.01); *A61L 27/18* (2013.01); *A61L 27/20* (2013.01);
(Continued)

(58) Field of Classification Search
CPC .... A61F 2/00; A61F 2/28; A61F 13/00; A61L 27/56
(Continued)

(56) References Cited

U.S. PATENT DOCUMENTS 5,522,895 A 6/1996 Mikos
6,107,102 A 8/2000 Ferrari
(Continued)

FOREIGN PATENT DOCUMENTS

EP 1664168 A2 6/2006
WO WO-1997045532 A1 12/1997
(Continued)

OTHER PUBLICATIONS

International Search Report and Written Opinion for PCT/US11/29832, dated Jun. 7, 2011.
(Continued)

*Primary Examiner* — Yashita Sharma
(74) *Attorney, Agent, or Firm* — Winstead PC

(57) ABSTRACT

In some embodiments, the present invention provides compositions that comprise: (1) a biodegradable polymer matrix; and (2) at least one biodegradable reinforcing particle that is dispersed in the matrix. In some embodiments, the biodegradable reinforcing particle is selected from the group consisting of porous oxide particles and porous semiconductor particles. In additional embodiments, the compositions of the present invention further comprise a (3) porogen particle that is also dispersed in the matrix. In further embodiments, the compositions of the present invention are also associated with one or more active agents. In various embodiments, the active agents are associated with the biodegradable polymer matrix, the biodegradable reinforcing particle, and/or the porogen particle. In various embodiments, the compositions of the present invention may be
(Continued)

utilized as scaffolds, such as scaffolds for treating bone defects. Further embodiments of the present invention pertain to methods of making the compositions of the present invention.

26 Claims, 57 Drawing Sheets

Related U.S. Application Data

(60) Provisional application No. 61/363,126, filed on Jul. 9, 2010, provisional application No. 61/363,835, filed on Jul. 13, 2010.

(51) Int. Cl.
| | | |
|---|---|---|
| *A61L 27/16* | (2006.01) | |
| *A61L 27/18* | (2006.01) | |
| *A61L 27/20* | (2006.01) | |
| *A61L 27/38* | (2006.01) | |
| *A61L 27/44* | (2006.01) | |

(52) U.S. Cl.
  CPC ....... *A61L 27/3834* (2013.01); *A61L 27/3847* (2013.01); *A61L 27/446* (2013.01); *A61L 27/54* (2013.01); *A61L 2300/64* (2013.01); *A61L 2430/02* (2013.01)

(58) Field of Classification Search
  USPC ....... 623/23.47–23.63; 424/9.411, 93.7, 724, 424/400, 422–426, 486
  See application file for complete search history.

(56) References Cited

U.S. PATENT DOCUMENTS

| | | | |
|---|---|---|---|
| 6,124,373 A | 9/2000 | Peter et al. | |
| 6,281,257 B1 | 8/2001 | Ma et al. | |
| 6,355,270 B1 | 3/2002 | Ferrari et al. | |
| 6,635,281 B2 * | 10/2003 | Wong et al. | 424/473 |
| 6,656,508 B2 | 12/2003 | Goldenberg et al. | |
| 6,858,229 B1 | 2/2005 | Hubbell et al. | |
| 7,186,267 B2 | 3/2007 | Aston et al. | |
| 7,763,277 B1 | 7/2010 | Canham et al. | |
| 2002/0001619 A1 | 1/2002 | Goldenberg et al. | |
| 2002/0168406 A1 | 11/2002 | Goldenberg et al. | |
| 2003/0114366 A1 | 6/2003 | Martin et al. | |
| 2005/0095416 A1 * | 5/2005 | Hanzawa et al. | 428/304.4 |
| 2005/0177249 A1 | 8/2005 | Kladakis et al. | |
| 2006/0026335 A1 | 2/2006 | Hodgson et al. | |
| 2007/0178159 A1 | 8/2007 | Chen et al. | |
| 2008/0085292 A1 * | 4/2008 | Rezania et al. | 424/422 |
| 2008/0095820 A1 * | 4/2008 | Kumta et al. | 424/423 |
| 2008/0102030 A1 | 5/2008 | Decuzzi et al. | |
| 2008/0206308 A1 | 8/2008 | Jabbari et al. | |
| 2008/0206344 A1 | 8/2008 | Decuzzi et al. | |
| 2008/0280140 A1 | 11/2008 | Ferrari et al. | |
| 2008/0311182 A1 | 12/2008 | Ferrari et al. | |
| 2009/0012627 A1 | 1/2009 | Claesson et al. | |
| 2010/0029785 A1 | 2/2010 | Decuzzi et al. | |
| 2010/0196435 A1 | 8/2010 | Freeman et al. | |

FOREIGN PATENT DOCUMENTS

| | | |
|---|---|---|
| WO | WO-2005020849 A2 | 3/2005 |
| WO | WO-2006023130 A2 | 3/2006 |
| WO | WO-2007089997 A2 | 8/2007 |
| WO | WO-2007/120248 A2 | 10/2007 |
| WO | WO-2008006658 A1 | 1/2008 |
| WO | WO-2008/021908 A2 | 2/2008 |
| WO | WO-2008/041970 A2 | 4/2008 |
| WO | WO-2008073856 A2 | 6/2008 |
| WO | WO-2010040188 A1 | 4/2010 |
| WO | WO-2010074675 A1 | 7/2010 |
| WO | WO-2010082910 A1 | 7/2010 |
| WO | WO-2012/005783 A1 | 1/2012 |

OTHER PUBLICATIONS

International Preliminary Report on Patentability for PCT/US11/29832, dated Jan. 24, 2013.
Peter et al., Crosslinking characteristics of an injectable poly(propylene fumarate)/beta-tricalcium phosphate paste and mechanical properties of the crosslinked composite for use as a biodegradable bone cement, J Biomed Mater Res. 1999; 44: 314-21.
Mano et al., Bioinert, biodegradable and injectable polymeric matrix composites for hard tissue replacement: state of the art and recent developments, Composites Science and Technology 64(2004), 789-817.
Rezwan et al. Biodegradable and bioactive porous polymer/inorganic composite scaffolds for bone tissue engineering, Biomaterials 27(2006) 3413.
Boccaccini et al., Bioactive composite materials for tissue engineering scaffolds, Expert Review of Medical Devices 2005, 2(3), 303.
Chung et al., Surface engineered and drug releasing pre-fabricated scaffolds far tissue engineering, Advanced Drug Delivery Reviews, 59(4-5), 2007, 249.
Tan et al. , Injectable, Biodegradable Hydrogels for Tissue Engineering Applications, Materials 2010, 3, 1746.
Mano et al., Natural origin biodegradable systems in tissue engineering and regenerative medicine: present status and some moving trends, J R Soc Interface, 2007 4(17): 999-1030.
Ranganathan et al., Shaping the micromechanical behavior of multi-phase composites for bone tissue engineering, Acta Biomater. Sep. 2010, pp. 3448-3456.
Tasciotti E. et al, Mesoporous silicon particles as a multistage delivery system for imaging and therapeutic applications, 2008 Nature Nanotechnology 3, 151-157.
Cohen M.H. et al., Microfabrication of silicon-based nanoporous particulates for medical applications, Biomedical Microdevices 5:3, 253-259, 2003.
Foraker, A.B. et al., Microfabricated Porous Silicon Particles Enhance Paracellular Delivery of Insulin Across Intestinal Caco-2 Cell Monolayers, Pharma. Res. 20 (1), 110-116 (2003).
Salonen, J. et al., Pharmacokinetics study on mesoporous silica-captopril controlled release systems, Jour. Contr. Rel. 108, 362-374 (2005).
Paik J.A. et al., Micromachining of mesoporous oxide films for microelectromechanical system structures, J. Mater. Res., vol. 17, Aug. 2002, p. 2121.
Chiappini, E. Tasciotti, J.R. Fakhoury, D. Fine, L. Pullan, Y.-C. Wang, L. Fu, X. Liu, and M. Ferrari. Tailored Porous Silicon Microparticles: Fabrication and Properties. ChemPhysChem. 11:1029-1035 (2010).
Salonen J, Lehto V-P., Fabrication and chemical surface modification of mesoporous silicon for biomedical applications,Chemical Engineering Journal 2008;137(1):162-172.
Sun W, Puzas JE, Sheu T-J, Fauchet PM., Porous silicon as a cell interface for bone tissue engineering, Physica status solidi (a) 2007;204(5):1429-1433.
C.A. Prestidge, T.J. Barnes, C.H. Lau, C. Barnett, A. Loni, and L. Canham. Mesoporous silicon: a platform for the delivery of therapeutics. Expert Opin Drug Deily. 4:101-110 (2007).
C.A. Prestidge, T.J. Barnes, A. Mierczynska-Vasilev, W. Skinner, F. Peddie, and C. Barnett. Loading and release of a model protein from porous silicon powders. physica status solidi (a). 204:3361-3366 (2007).
C.A. Prestidge, T.J. Barnes, A. Mierczynska-Vasilev, I. Kempson, F. Peddie, and C. Barnett. Peptide and protein loading into porous silicon wafers. physica status solidi (a). 205:311-315 (2008).
E.J. Anglin, M.P. Schwartz, V.P. Ng, L.A. Perelman, and M.J. Sailor. Engineering the Chemistry and Nanostructure of Porous Silicon Fabry-Pérot Films for Loading and Release of a Steroid. Langmuir. 20:11264-11269 (2004).

(56) References Cited

OTHER PUBLICATIONS

M. Kilpeläinen, J. Riikonen, M.A. Vlasova, A. Huotari, V.P. Lehto, J. Salonen, K.H. Herzig, and K. Järvinen. In vivo delivery of a peptide, ghrelin antagonist, with mesoporous silicon microparticles. Journal of Controlled Release. 137:166-170 (2009).

M. Ferrari, Nanogeometry: Beyond drug delivery, Nat Nano. 3:131-132 (2008).

Vallet-Regi M., Ordered Mesoporous Materials in the Context of Drug Delivery Systems and Bone Tissue Engineering, 2006. Chem Eur J 12:5934-5943.

W. Linhart, F. Peters, W. Lehmann, K. Schwarz, A.F. Schilling, M. Amling, J.M. Rueger, M. Epple, Biologically and chemically optimized composites of carbonated apatite and polyglycolide as bone substitution materials, Journal of Biomedical Materials Research 54 (2001) 162-171.

J. Salonen, A.M. Kaukonen, J. Hirvonen, and V.P. Lehto. Mesoporous silicon in drug delivery applications. Journal of Pharmaceutical Sciences. 97:632-653 (2008).

B. Godin, J. Gu, R.E. Serda, R. Bhavane, E. Tasciotti, C. Chiappini, X. Liu, T. Tanaka, P. Decuzzi, and M. Ferrari. Tailoring the degradation kinetics of mesoporous silicon structures through PEGylation. Journal of Biomedical Materials Research Part A. 94A:1236-1243 (2010).

R.E. Serda, A. Mack, M. Pulikkathara, A.M. Zaske, C. Chiappini, J.R. Fakhoury, D. Webb, B. Godin, J.L. Conyers, X.W. Liu, J.A. Bankson, and M. Ferrari. Cellular Association and Assembly of a Multistage Delivery System. Small. 6:1329-1340 (2010).

S. Ferrati, A. Mack, C. Chiappini, X. Liu, A.J. Bean, M. Ferrari, and R.E. Serda. Intracellular trafficking ofsilicon particles and logic-embedded vectors. Nanoscale. 2:1512-1520 (2010).

\* cited by examiner

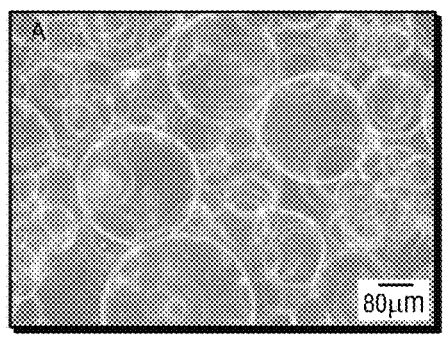
FIG. 7A
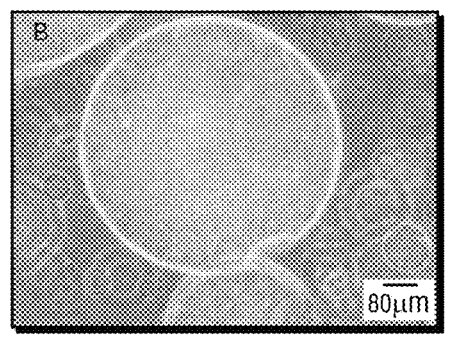
FIG. 7B
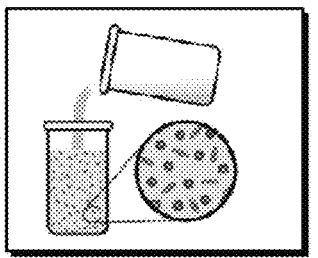
FIG. 7C
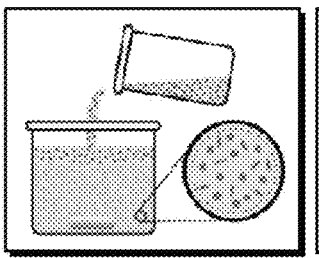
FIG. 7D
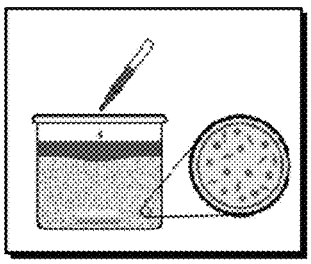
FIG. 7E
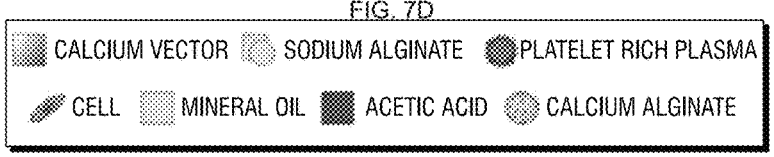
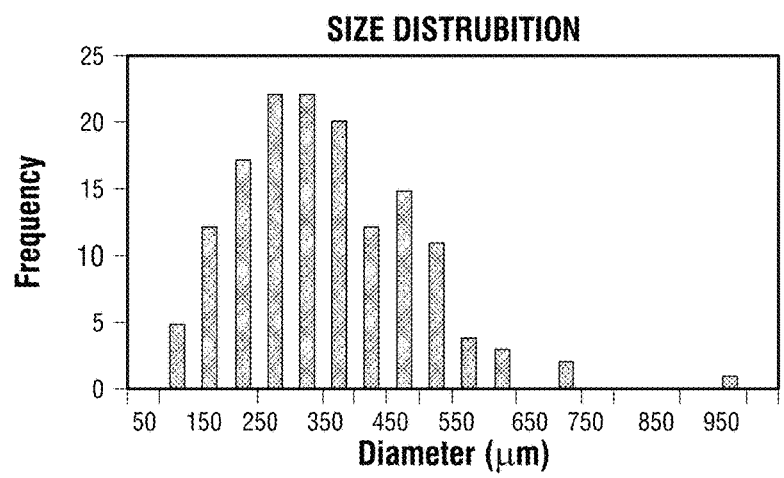
FIG. 7F

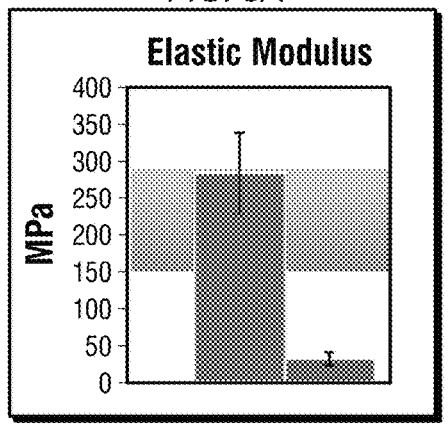
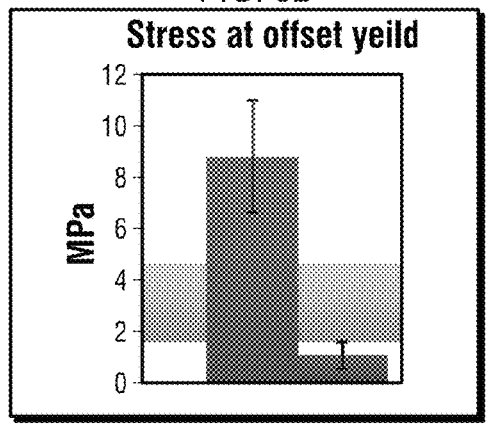
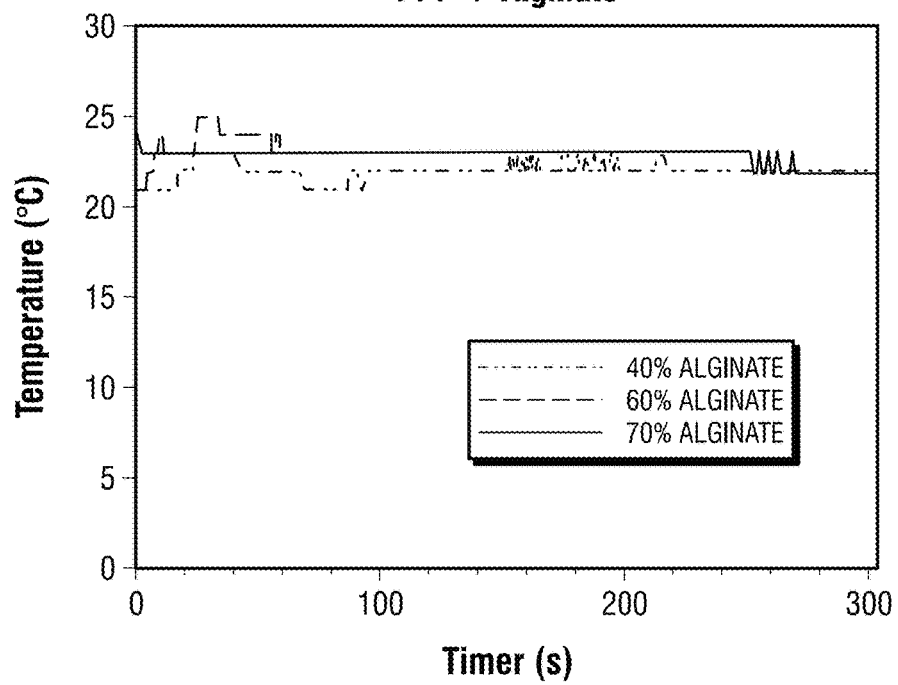
FIG. 9

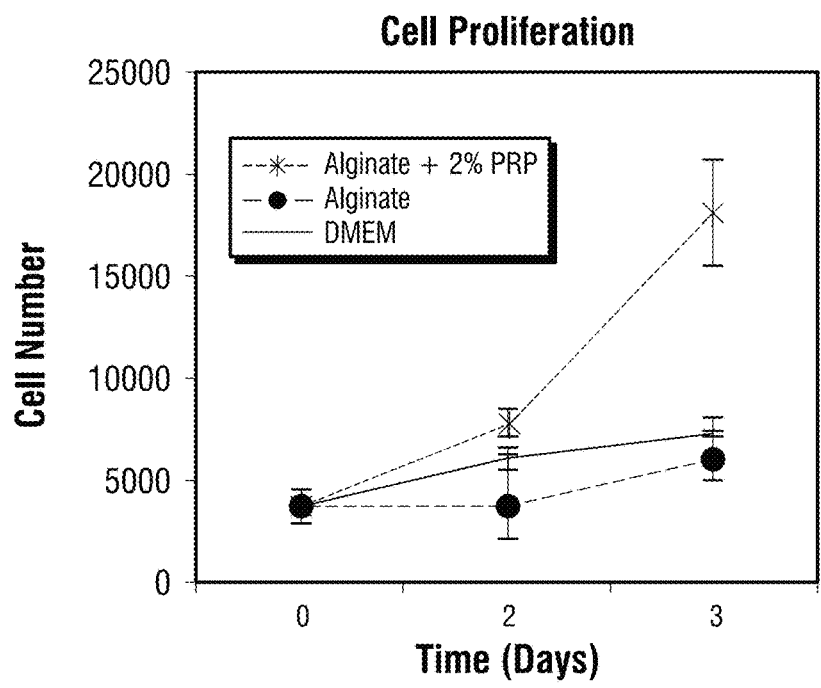
FIG. 10E
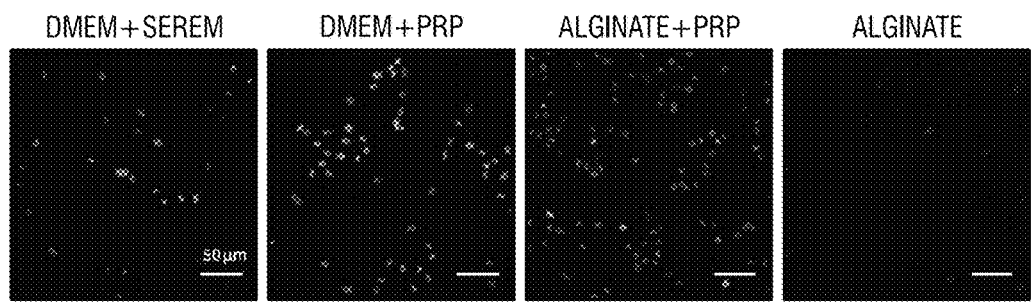
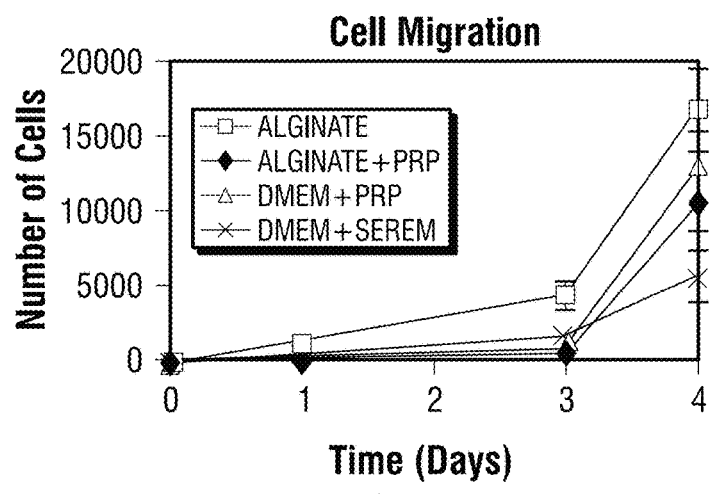
FIG. 10F

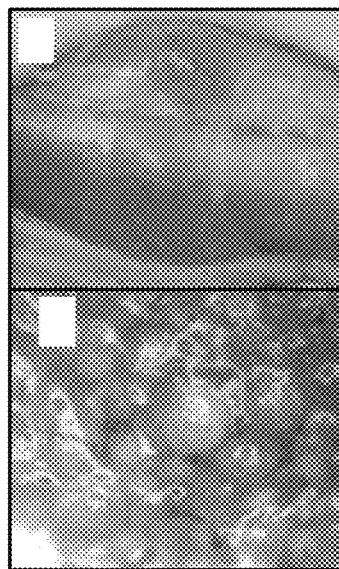
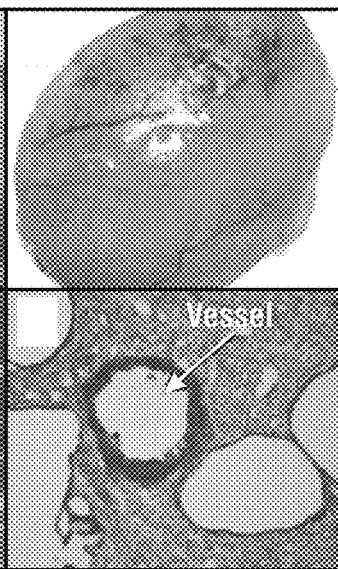
FIG. 10G
FIG. 10H

FIG. 10I
FIG. 10J
FIG. 10K
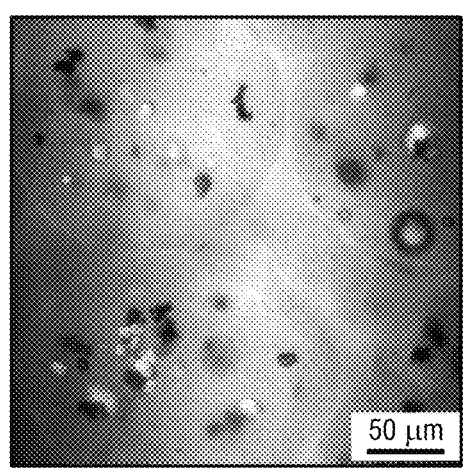
FIG. 10L
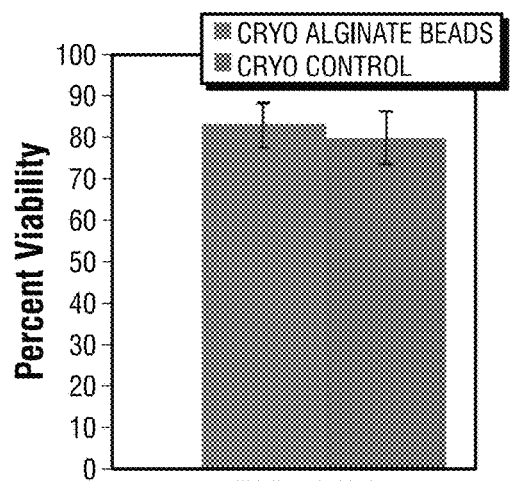
FIG. 10M

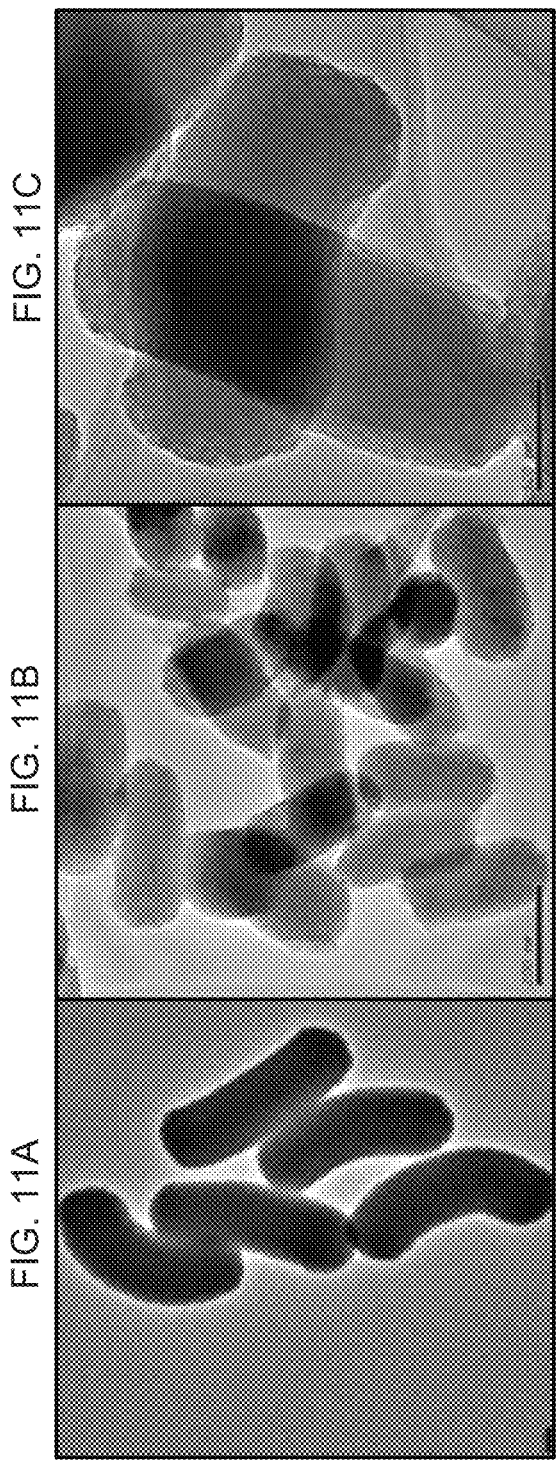

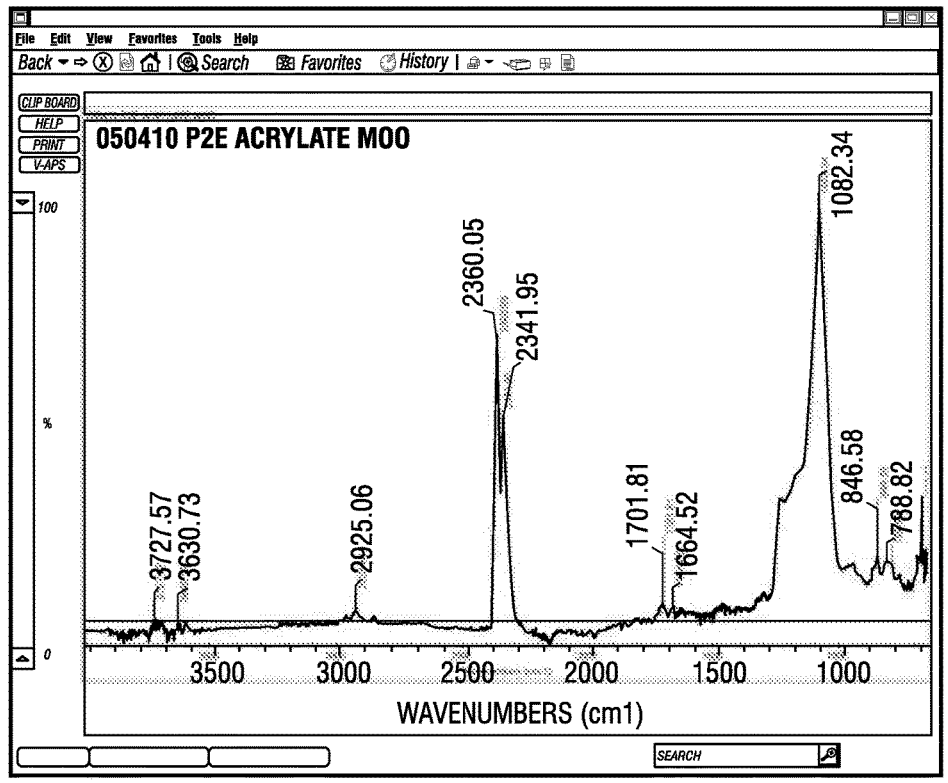
FIG. 18
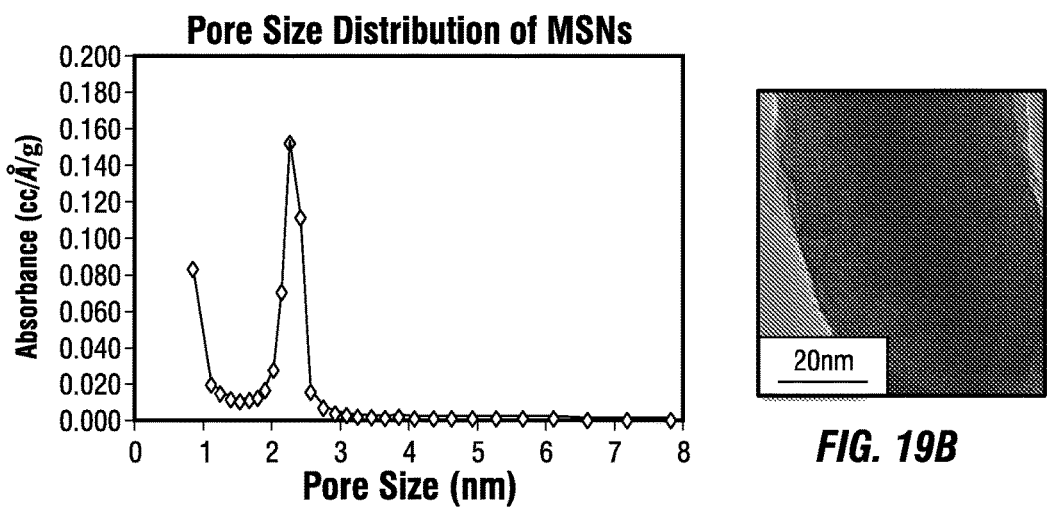
FIG. 19A
FIG. 19B

| MPS Type | ZETA Potential | σ |
|---|---|---|
| CONTROL | 30.3925 | 1.559217 |
| 10% APTES | 9.81333 | 0.456107 |
| 20% APTES | 7.54333 | 0.607069 |
| 30% APTES | 5.38333 | 0.411866 |

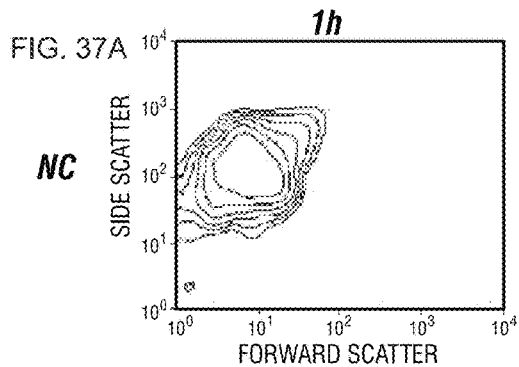
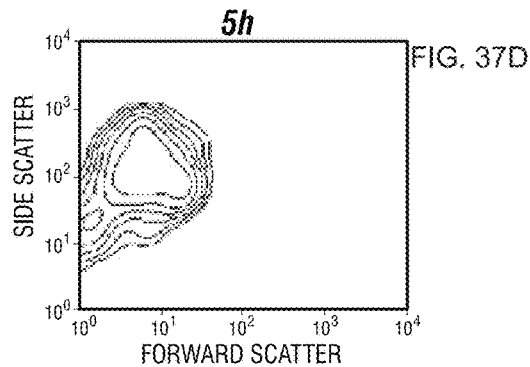
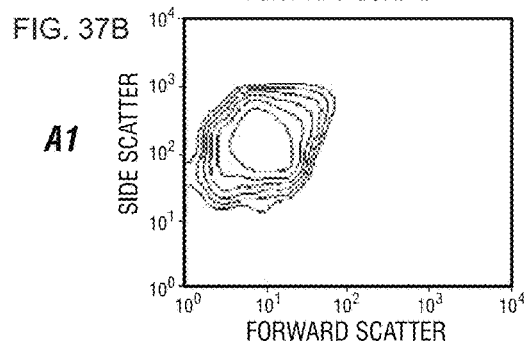
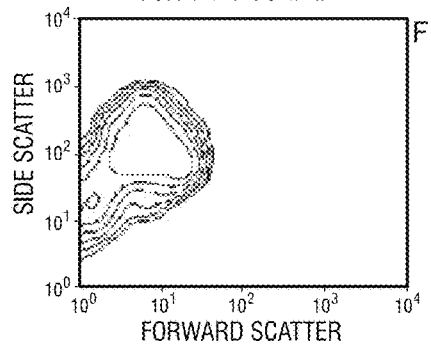
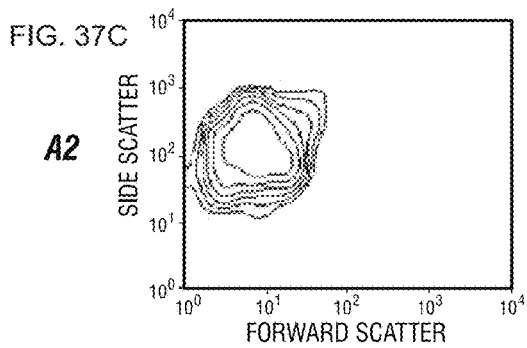
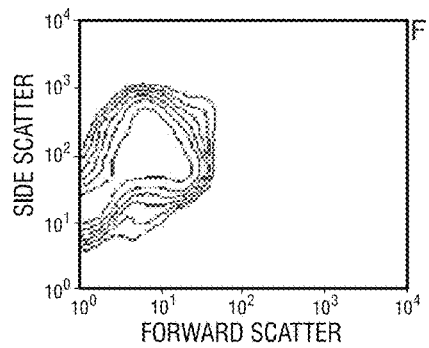
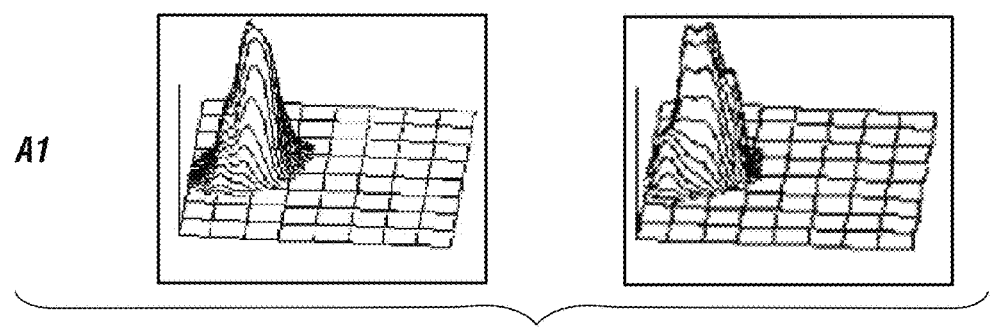

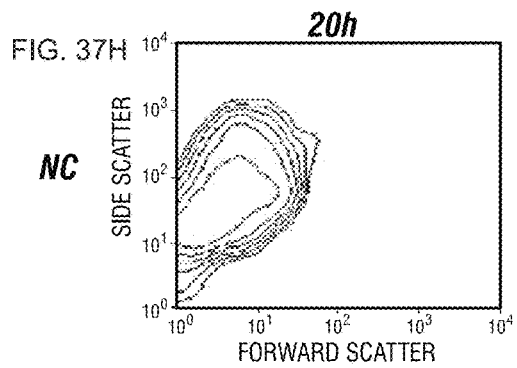
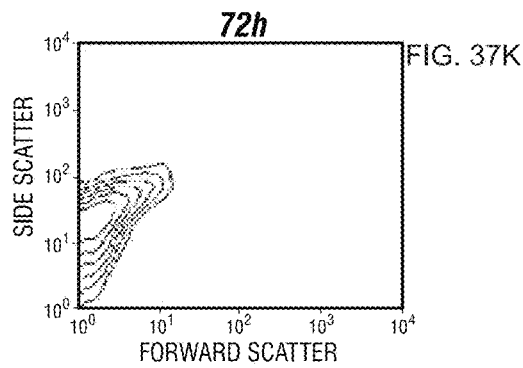
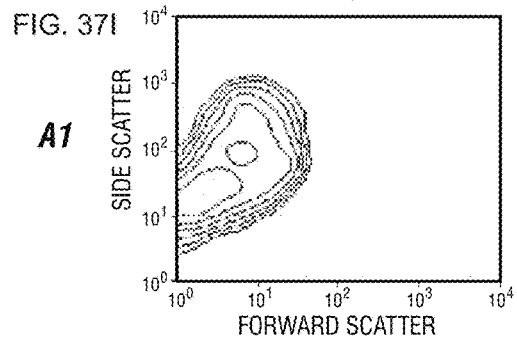
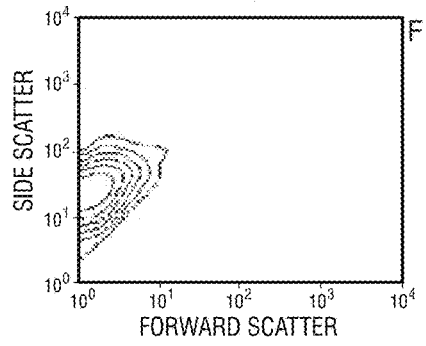
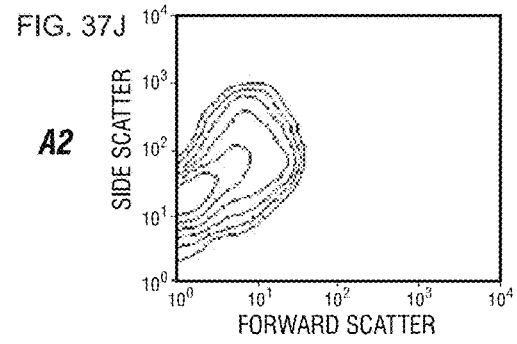
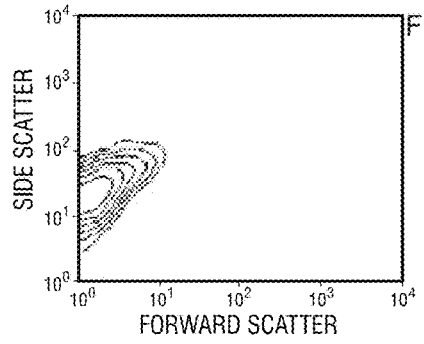
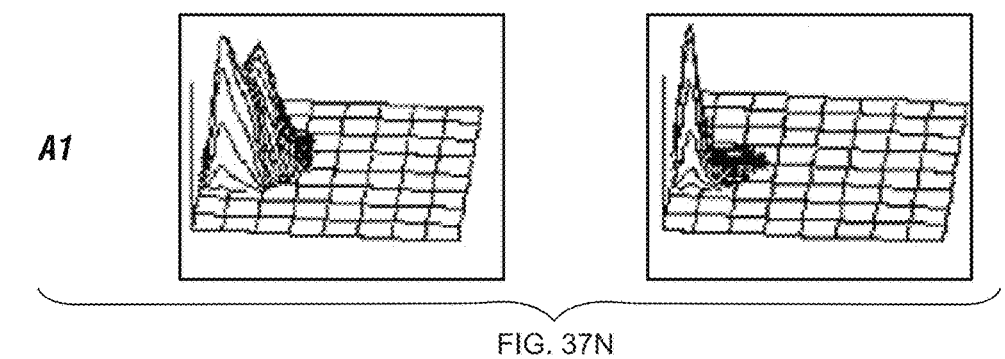
FIG. 37N

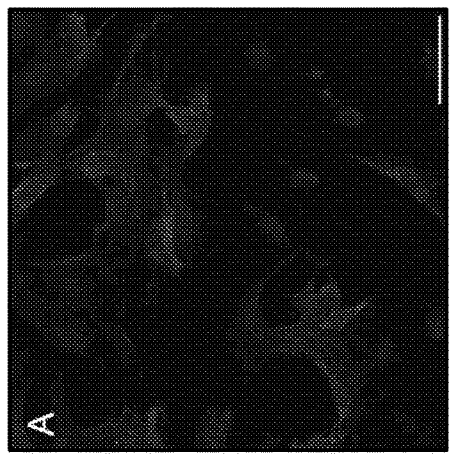
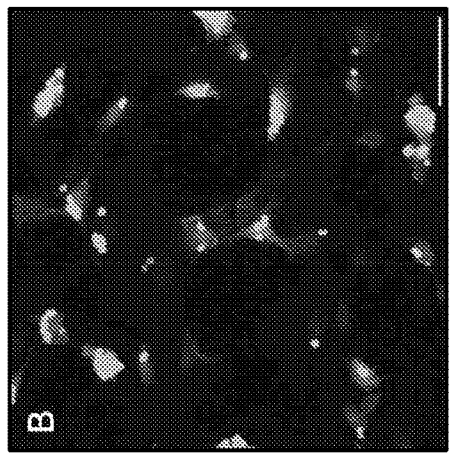
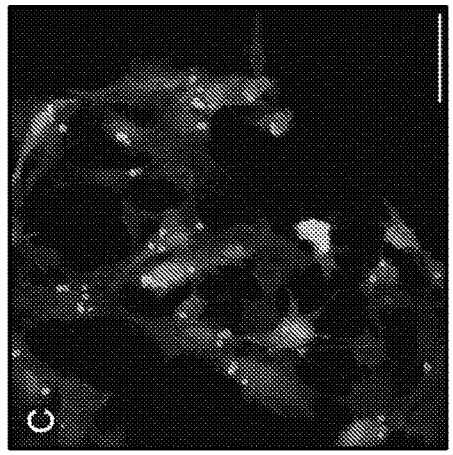
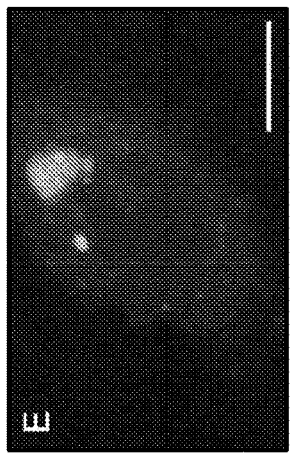
*FIG. 41A* *FIG. 41B* *FIG. 41C* *FIG. 41D* *FIG. 41E* *FIG. 41F*

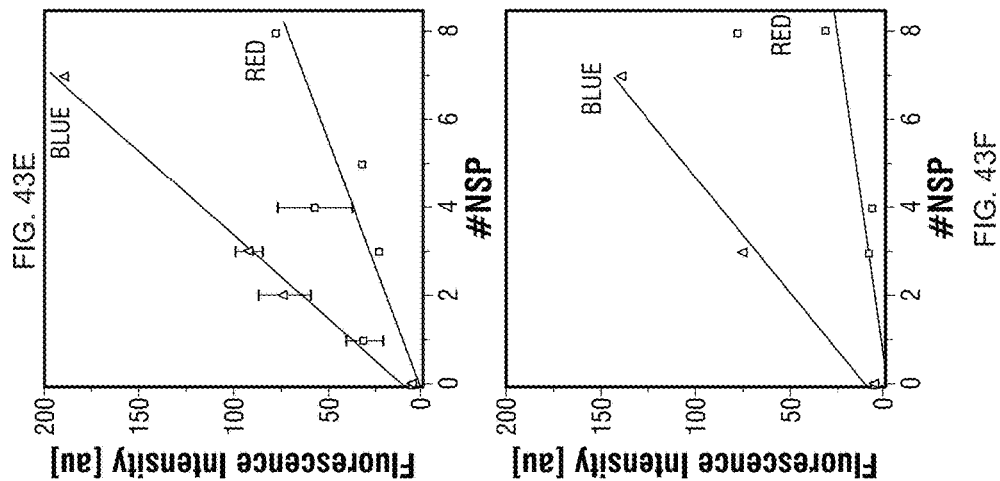
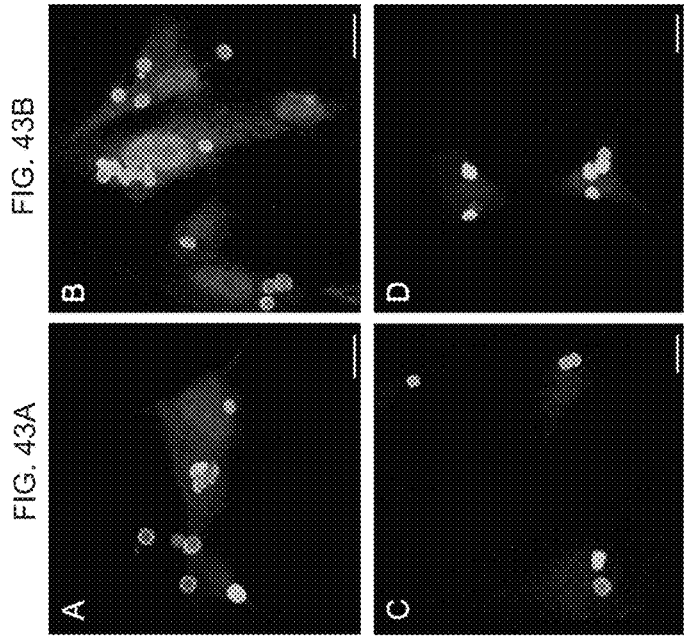

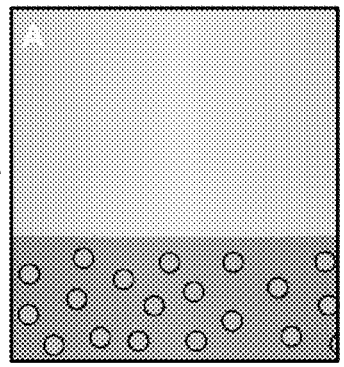
FIG. 44A
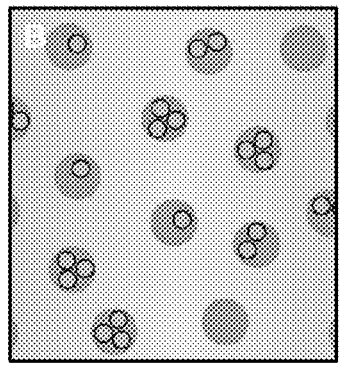
FIG. 44B
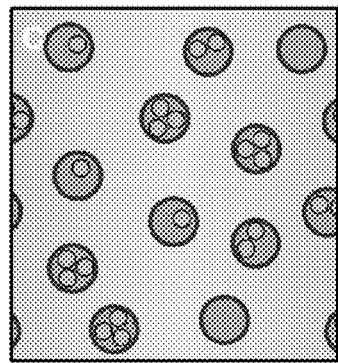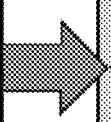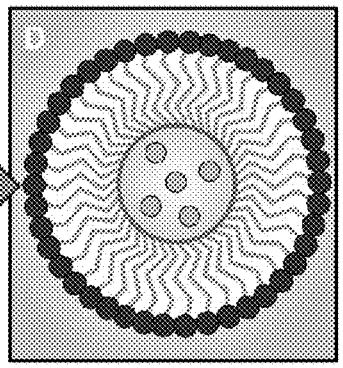
FIG. 44C
FIG. 44D
● Hydrophilic Part   ／ Lipophilic Part   ◎ pSi Particle

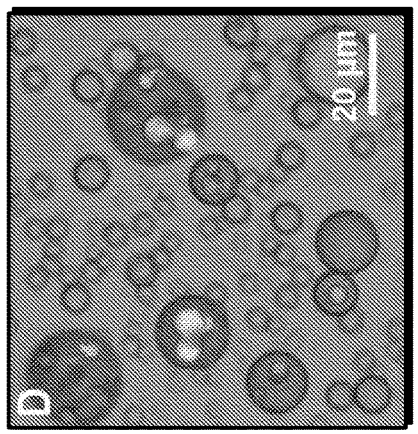
FIG. 47D
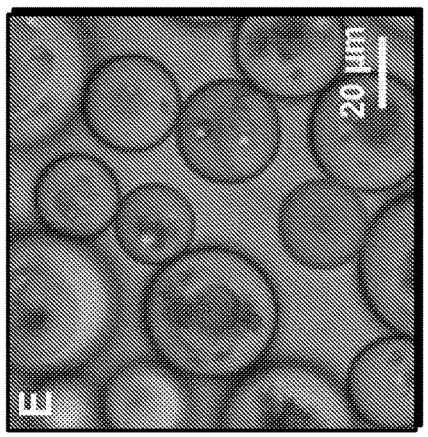
FIG. 47E
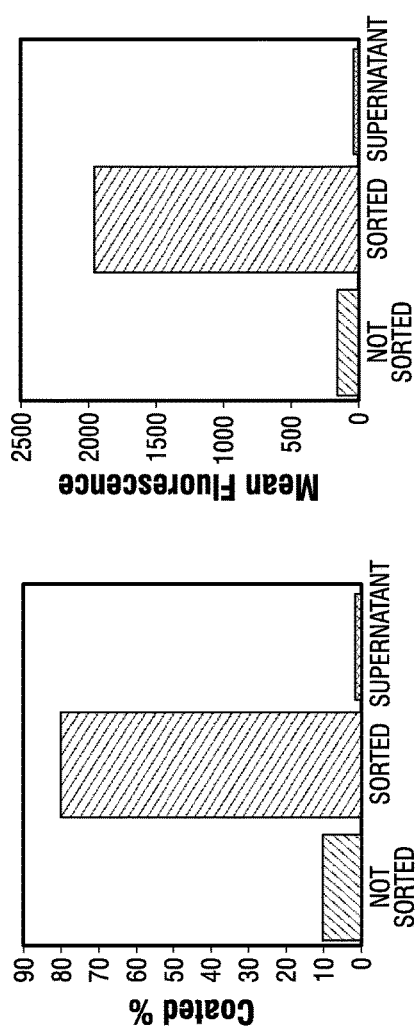
FIG. 47A
FIG. 47B
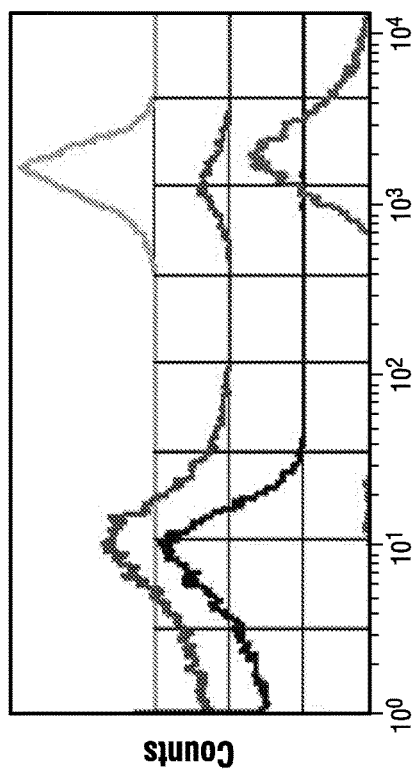
FIG. 47C

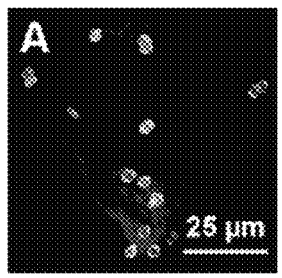 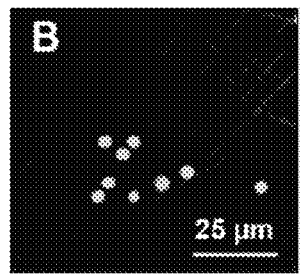 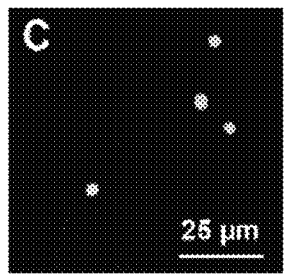
*FIG. 54A*  *FIG. 54B*  *FIG. 54C*
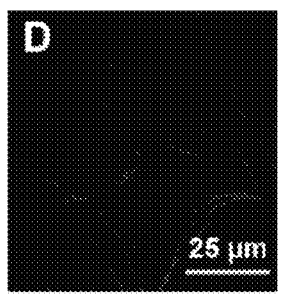 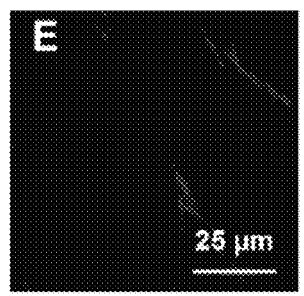 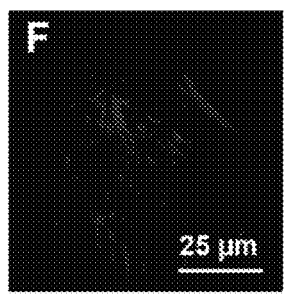
*FIG. 54D*  *FIG. 54E*  *FIG. 54F*
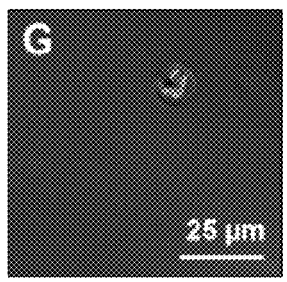 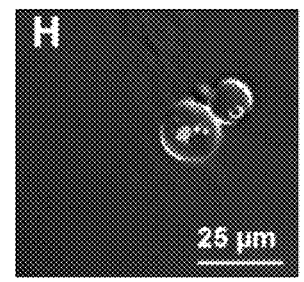 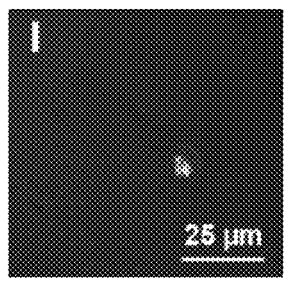
*FIG. 54G*  *FIG. 54H*  *FIG. 54I*
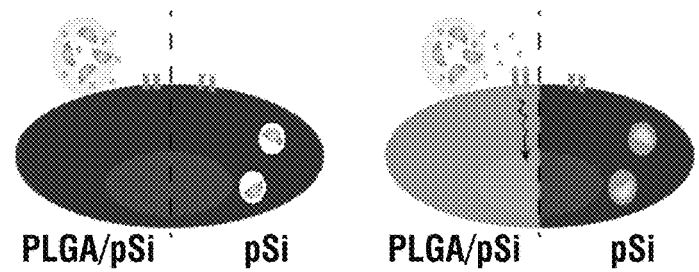
FIG. 54J

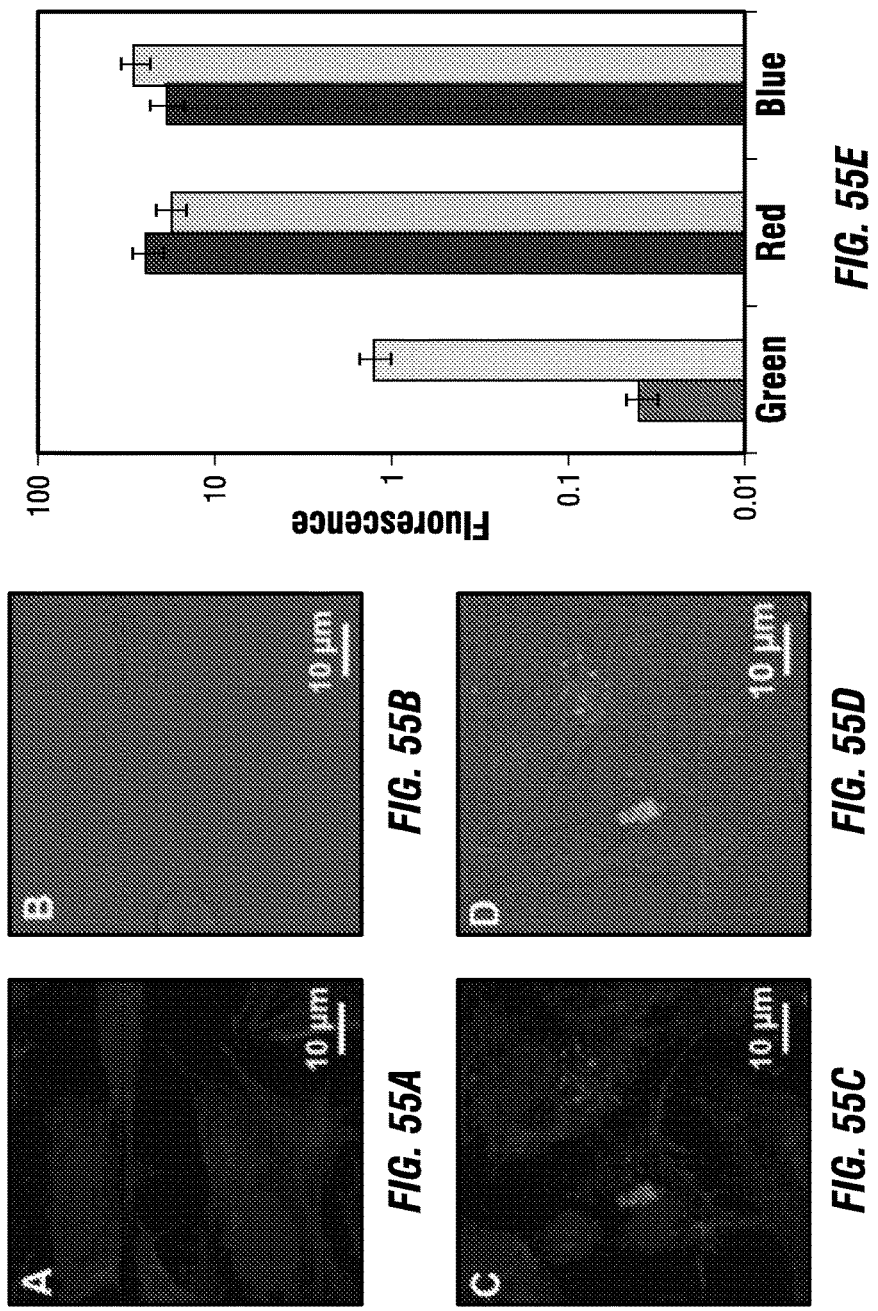

BIODEGRADABLE SCAFFOLDS

CROSS-REFERENCE TO RELATED APPLICATIONS

This application is a continuation of U.S. application Ser. No. 13/809,291, filed Mar. 22, 2013, which claims priority to U.S. Provisional Patent Application No. 61/363,835, filed on Jul. 13, 2010 and U.S. Provisional Patent Application No. 61/363,126, filed on Jul. 9, 2010. The entirety of each of the above-identified applications are incorporated herein by reference.

STATEMENT REGARDING FEDERALLY SPONSORED RESEARCH

This invention was made with government support under DARPA Grant No. W911NF-09-1-0044, awarded by the U.S. Department of Defense. The government has certain rights in the invention.

BACKGROUND OF THE INVENTION

Current compositions and methods for tissue engineering or wound healing through the use of scaffolds suffer from various limitations. Such limitations may include insufficient biocompatibility, insufficient biodegradability, lack of mechanical stability, and insufficient porosity for the delivery of active agents. Therefore, there is currently a need to develop new methods and compositions for tissue engineering and wound healing that address the aforementioned limitations.

BRIEF SUMMARY OF THE INVENTION

In some embodiments, the present invention provides compositions that comprise: (1) a biodegradable polymer matrix (e.g., an unsaturated biodegradable polymer, such as poly(propylene fumarate) (PPF)); and (2) at least one biodegradable reinforcing particle that is dispersed in the matrix. In some embodiments, the biodegradable reinforcing particle is selected from the group consisting of porous oxide particles and porous semiconductor particles (e.g., mesoporous silica particles). In additional embodiments, the compositions of the present invention further comprise a (3) porogen particle that is also dispersed in the matrix. In various embodiments, such porogen particles may be hydrogels (e.g., alginates, fibrins, and gelatins), natural or synthetic biodegradable particles, biodegradable porous particles (e.g., silicon porous particles), and biocompatible vesicles (e.g., liposomes and/or micelles).

In further embodiments, the compositions of the present invention are associated with one or more active agents. In various embodiments, the active agents are associated with the biodegradable polymer matrix, the biodegradable reinforcing particle, and/or the porogen particle. In some embodiments, the active agent comprises therapeutics, antibiotics, proteins, platelet rich plasma (PRP), cells (e.g., stem cells), degradation inducers of porogen particles (e.g., lactic acid and/or sodium citrate), anti-inflammatory agents, cell viability enhancing agents (e.g., glucose), and/or imaging agents (e.g., barium sulfate).

In various embodiments, the compositions of the present invention may be utilized as scaffolds, such as scaffolds for treating bone defects. Accordingly, in some embodiments, the present invention also pertains to methods of treating a bone defect in a subject by applying to an area of the bone defect in the subject a scaffold of the present invention. Further embodiments of the present invention pertain to methods of making the compositions of the present invention.

The methods and compositions of the present invention have numerous applications and advantages. For instance, in various embodiments, the compositions and methods of the present invention may be used in the treatment of bone defects, wound healing, tissue engineering, and the prevention or treatment of microbial infections.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated in the appended Figures. Understanding that these Figures depict only typical embodiments of the invention and are therefore not to be considered limiting of its scope, the invention will be described with additional specificity and detail through the use of the accompanying Figures in which:

FIG. 1C: confocal image green—cells; FIGS. 1D-1F are scanning electron microscopy (SEM) images).

FIG. 6A shows the integration of matrix components.

FIG. 6B shows the injection of the bioactive matrix into the bone defect;

FIG. 6C shows the area of the bone defect 1 week after injection. Degradation of alginate porogens and delivery of cells and SEs to the surrounding scaffold can be seen.

FIG. 6D shows the area of the bone defect 2 weeks after injection. Degradation of silicon enclosures (SEs) and microparticles or nanoparticles (MSNs) and initial vascularization can be seen.

FIG. 6E shows the area of the defect 3 weeks after injection. Woven bone formation can be seen.

FIG. 6F shows a remodeled bone that is formed after the completion of treatment.

FIGS. 7A-7F show various experimental results and schemes related to calcium alginate bead production.

FIGS. 7A-7B show calcium alginate beads produced without PRP (FIG. 7A), or with PRP (FIG. 7B).

FIGS. 7C-7E depict a scheme for production of calcium alginate beads by an internal gelation/emulsion technique. Insoluble calcium complex is dispersed in the aqueous phase containing sodium alginate and bioactive components (FIG. 7C). The aqueous phase is added to the oil phase with a surfactant present. Continuous stirring forms a stable emulsion (FIG. 7D). An oil soluble acid is then added to the mixture, thereby reducing the pH and triggering the release of calcium ions from the calcium complex to initiate gelation of the formed microspheres (FIG. 7E).

FIG. 7F shows the size distribution of the formed calcium alginate beads. The peak size is in the range of 250 to 400 microns.

FIGS. 8A-8B show elastic modulus (FIG. 8A) and stress (FIG. 8B) at offset yield of composite putty containing 40% alginate porogens and porous PPF scaffolds. The results are compared to native human trabecular bone.

FIG. 9 presents a temperature profile of PPF cross-linking with varying amounts of alginate porogens.

FIGS. 10A-10B show PDGF (platelet-derived growth factor), VEGF (vascular endothelial growth factor) (FIG. 10C), and RANTES (Regulated on Activation, Normal T Expressed and Secreted) (FIG. 10D), release from PRP within alginate porogens of varying sizes.

FIG. 10E shows the effects of PRP released from PRP loaded alginate porogens on cell proliferation over a three day period.

FIG. 10F shows the effects of PRP release from PRP loaded alginate porogens on cell migration. DAPI stained cells that migrated through an 8 micron transwell towards the released chemokines are shown on the top panel. Cell hemacytometer count of cells that migrated through the 8 micron transwell over the period of 4 days is illustrated in the graph on the bottom panel.

FIG. 10G shows subcutaneous implantation of calcium alginate porogens clotted in a fibrin matrix in rats, vascularization of the scaffold at 2 weeks (FIGS. 10H-I), H&E stain (FIG. 10J), and Goldner Trichrome stain (FIG. 10K) of histological section from the scaffold. The results indicate vessel formation and premature collagen formation (green).

FIG. 10L shows viability staining of stem cells cryofreezed in alginate porogens after thawing. Live cells are shown in green, and dead cells are shown in red. The bottom panel shows a trypan blue exclusion count of viable cells after cryopreservation and thawing (FIG. 10M).

FIGS. 11A-11C demonstrate an increase in aspect ratio and a decrease in the size of alginate porogen beads through the adjustment of tetraethyl orthosilicate (TEOS) (FIG. 11A), cetyl trimethyl ammonium bromide (CTAB) (FIG. 11B), and ammonia (FIG. 11C).

FIG. 18 presents an FTIR for post modified acrylate nanorods showing C=O peaks at 1716 $cm^{-1}$ and C=C peaks at 1621 $cm^{-1}$.

FIGS. 19A-19B present Brunauer-Emmett-Teller (BET) data showing the pore size distribution of silica nanorods to be around 2.56 nm.

FIG. 20A shows high cell viability after 24 hours of treatment with silica concentrations of about 0.01% by weight. The silica used in this experiment are washed E (post modified) and washed CC (co-condensated).

FIG. 20B shows viable cell count of MDA231 cells incubated with mesoporous nanorods (MSNRs). The cells are stained with Annexin V, which is indicative of apoptosis.

FIG. 20C shows MTT assays of human umbilical vein endothelial cells (HUVEC) incubated with MSNRs.

FIG. 25A shows the stress offset of control, 2.5% co-condensated silica nanorods (CC) and post-modified silica (E)

FIG. 25B shows the compressive modulus of 2.5% co-condensated silica nanorods (CC) and post-modified silica when dispersed in PPF polymer.

FIG. 26A shows data relating to the mineralization of agarose-coated silica nanoparticle scaffolds.

FIG. 26B shows images from a mineralization study with Rat Compact Bone stromal cells after 3 weeks.

From left to right the first panel shows a phase image of matrigel alone in osteogenic media;

the second panel shows a phase image of matrigel and mSNR in osteogenic media; and the third panel shows a phase image of matrigel and mSNR, in osteogenic media. The sample was stained with Von Kossa stain for calcium-phosphate mineral (brown) and alkaline phosphatase enzyme activity (blue). The sample was also stained with the nuclear counterstain, nuclear fast red (pink).

Figure 26A:
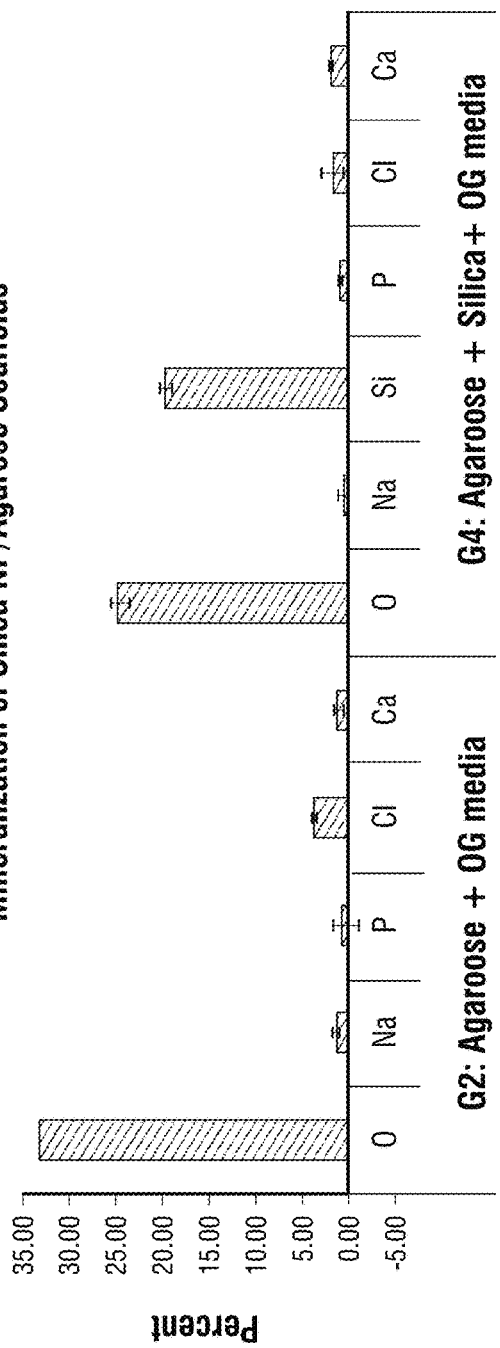
FIGS. 26A-26C show data relating to the mineralization of various scaffolds, and the use of PPF in various compositions.
Figure 26B:
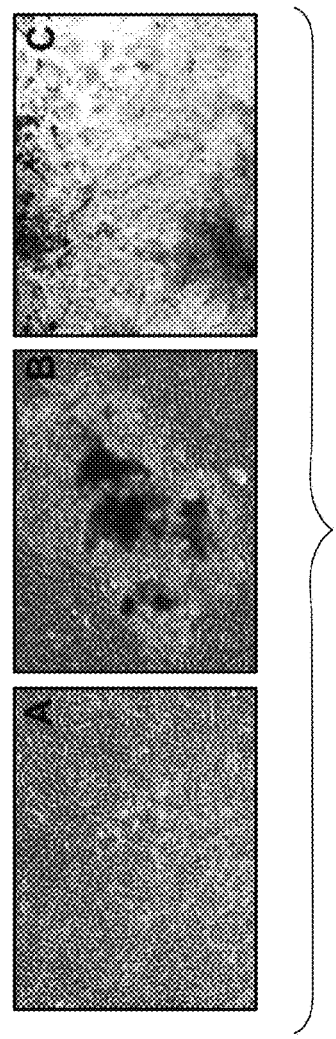
Figure 26C:
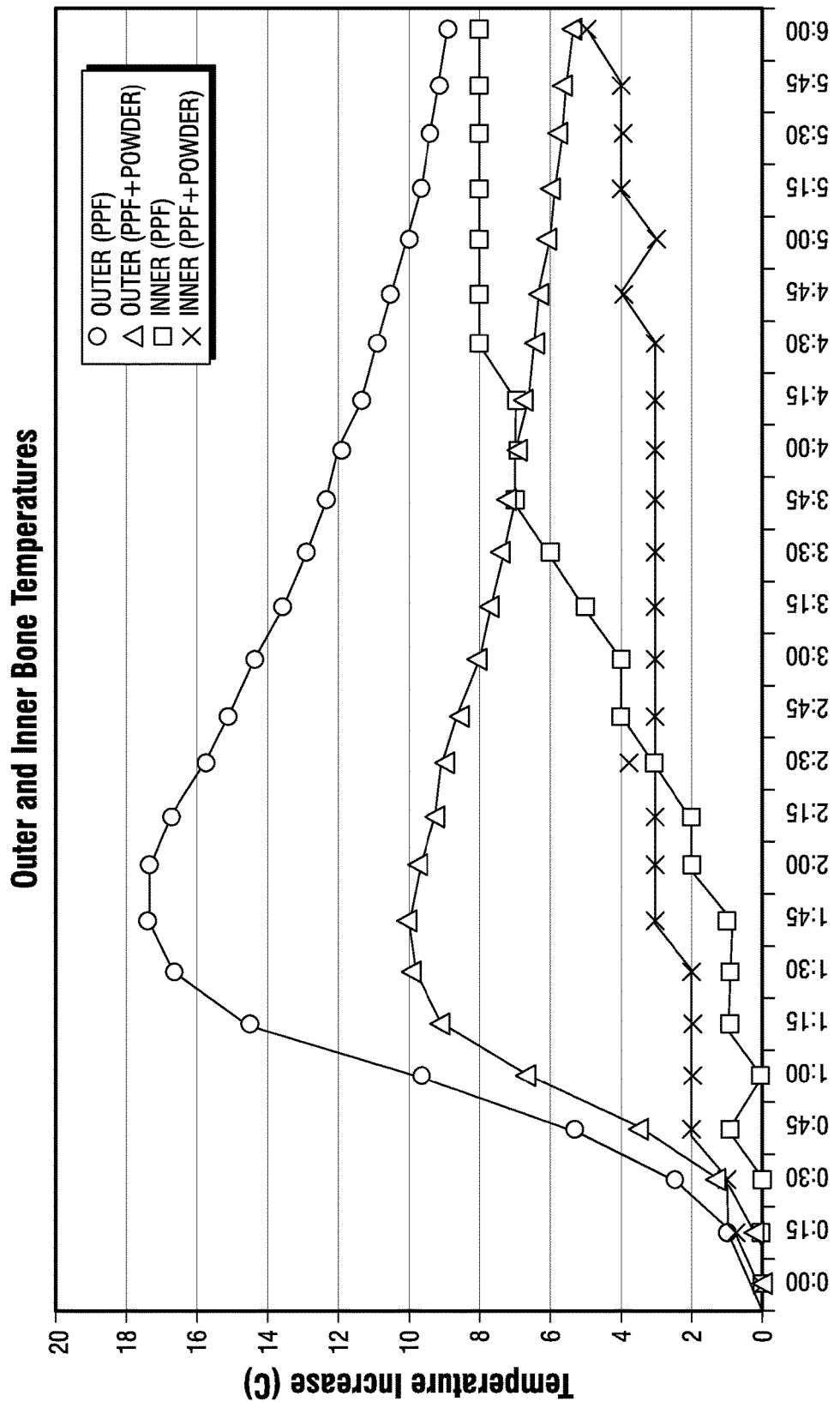

FIG. 26C shows temperature increase due to PPF injectable putty cross-linking.

Figure 27:
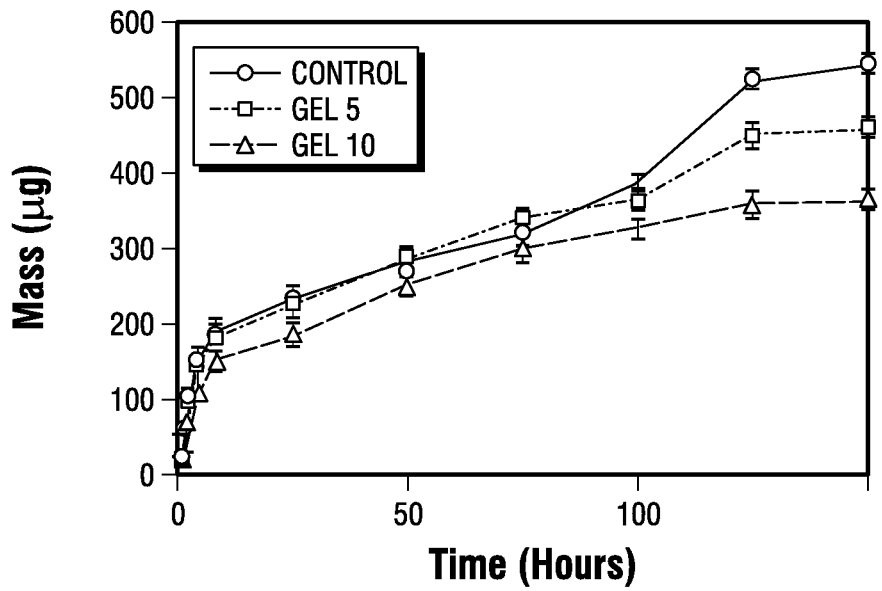

FIG. 27 shows cefazolin release from gelatin-coated mesoporous silicon (MPS).

Figure 28:
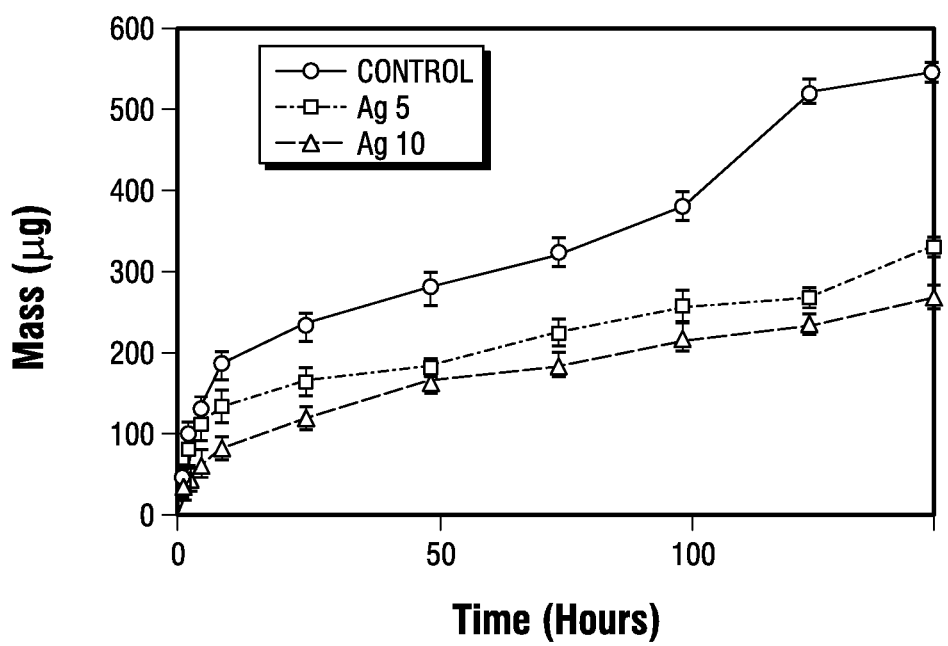

FIG. 28 shows cefazolin release from agarose coated MPS.

Figure 29:
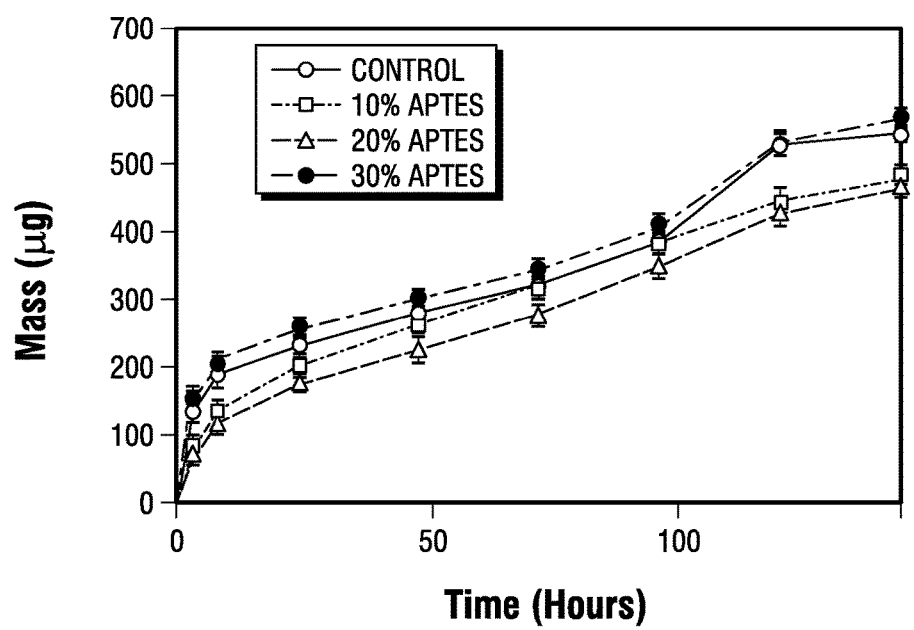

FIG. 29 shows cefazolin release from APTES coated MPS.

Figure 30:
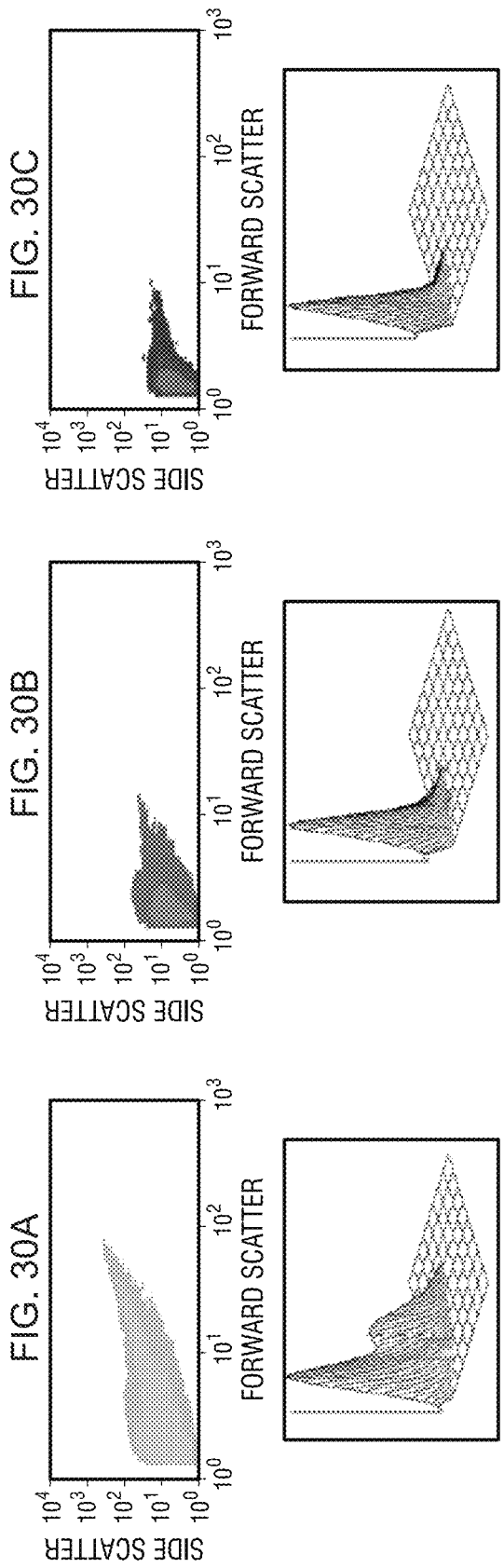

FIGS. 30A-30C show results from the flow cytometry analysis of MPS (FIG. 30A: 2000×g rcf; FIG. 30B: 10000×g rcf; FIG. 30C: 26000×g rcf). Data are from one experiment representative of three. SSC: side scatter; FSC: forward scatter.

Figure 31:
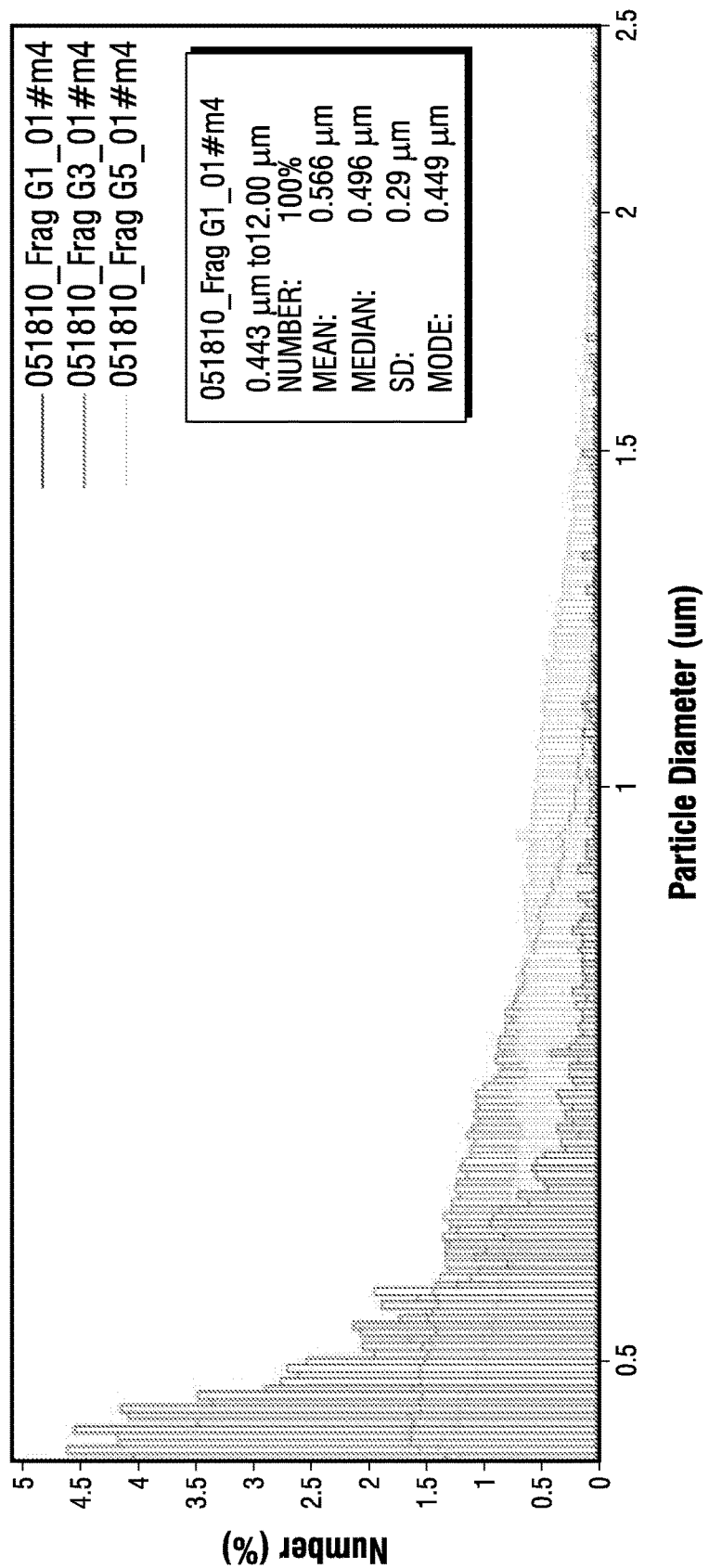

FIG. 31 shows results from multisizer analysis of the MPS.

Figure 32:
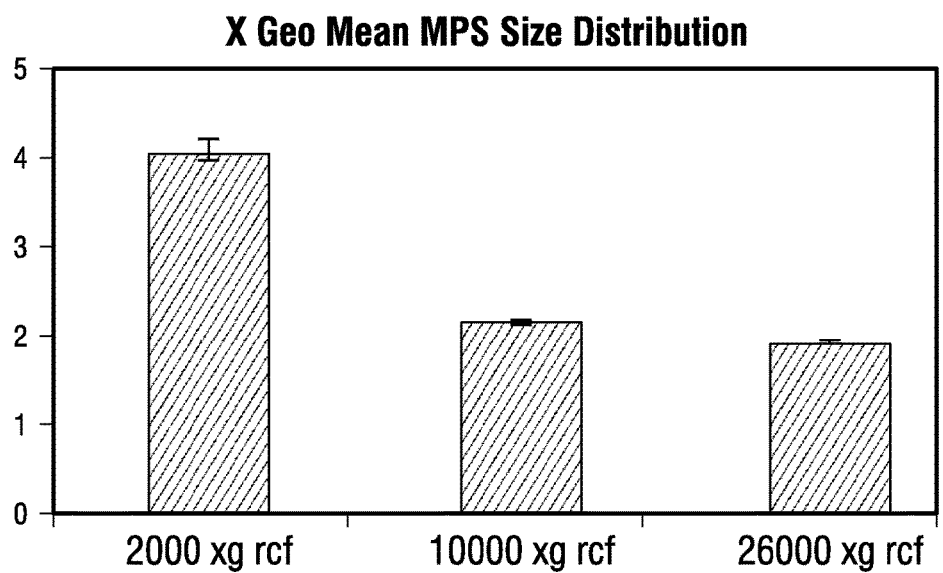

FIG. 32 presents results of FACS analysis of geometric mean X value of MPS Size Distribution.

Figure 33:
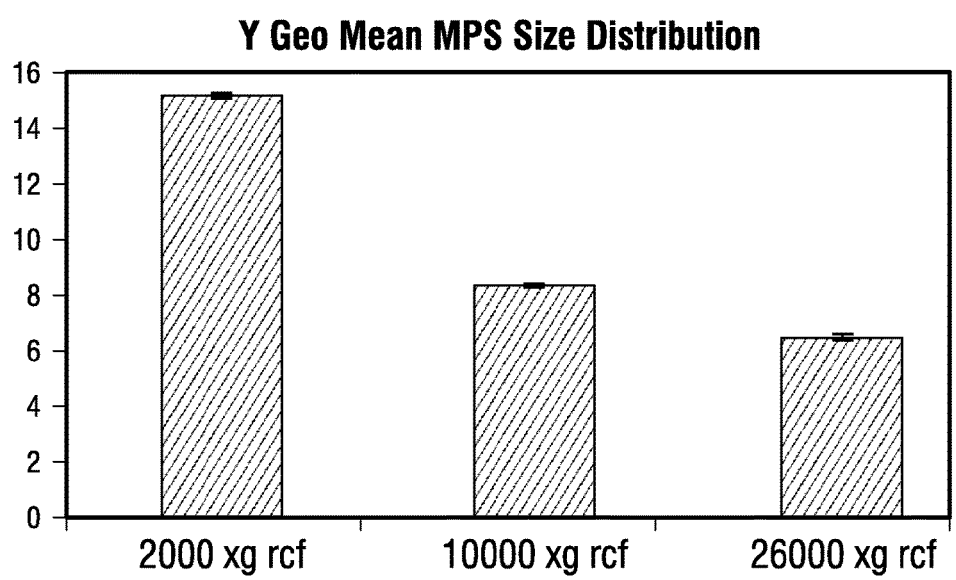

FIG. 33 presents results of FACS analysis of geometric mean Y value of MPS Size Distribution.

Figures 34A, 34B:
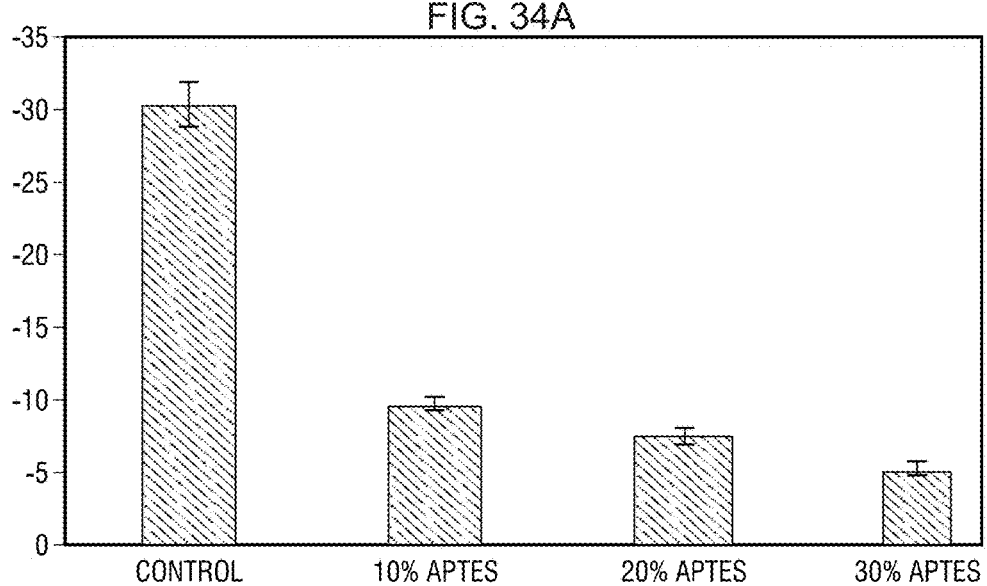
Figure 35A:
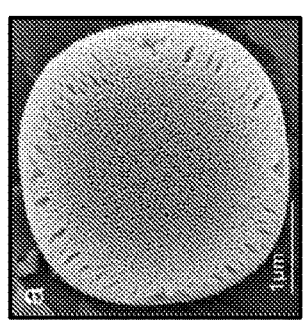
Figure 35B:
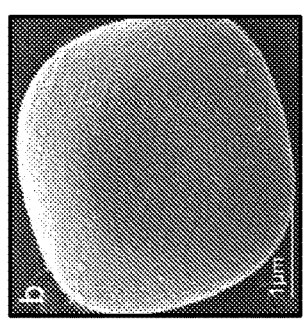
Figure 35C:
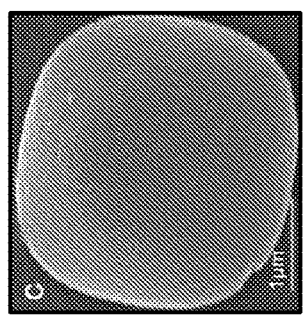
Figure 35D:
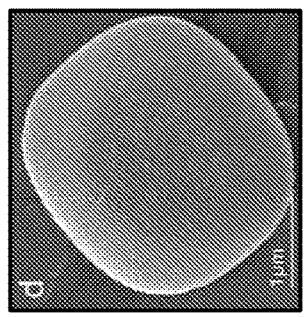
Figure 35E:
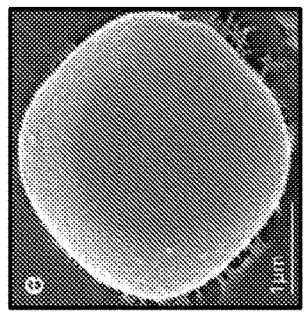
Figure 35F:
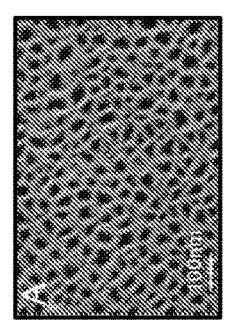
Figure 35G:
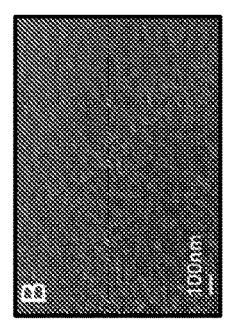
Figure 35H:
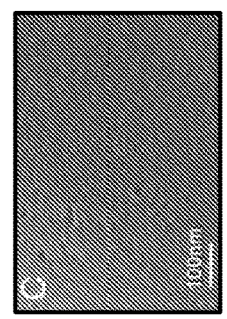
Figure 35I:
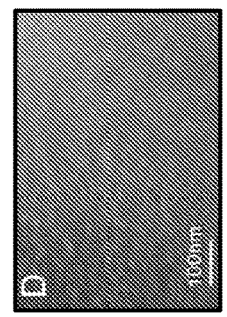
Figure 35J:
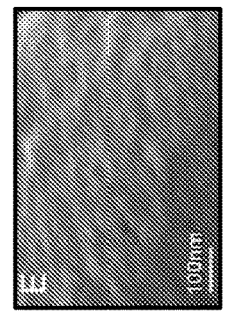
Figure 36A:
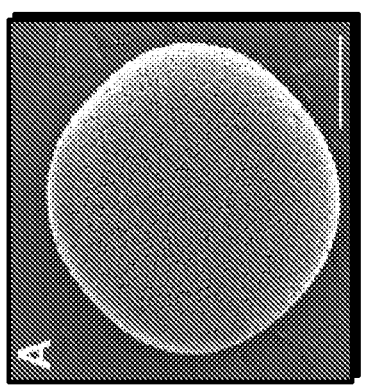
Figure 36B:
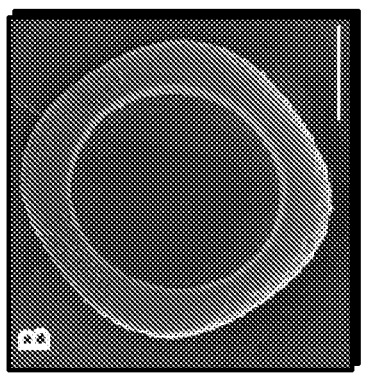
Figure 36C:
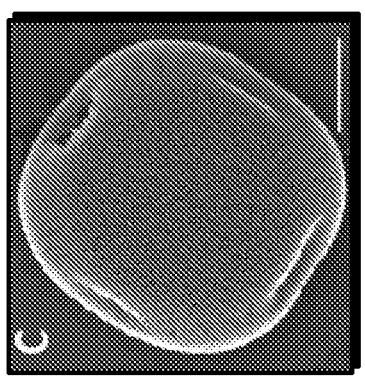
Figure 36D:
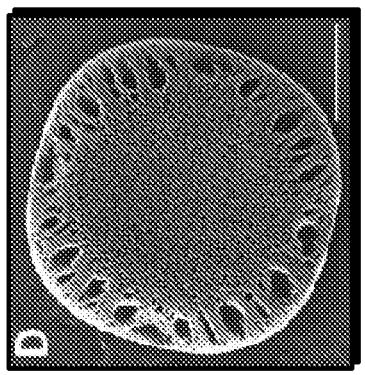
Figure 36E:
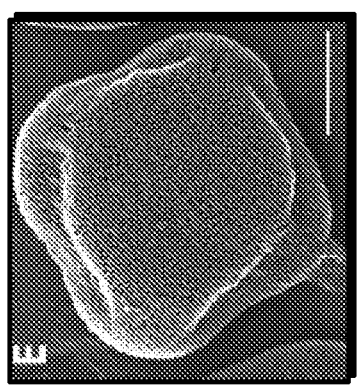
Figure 36F:
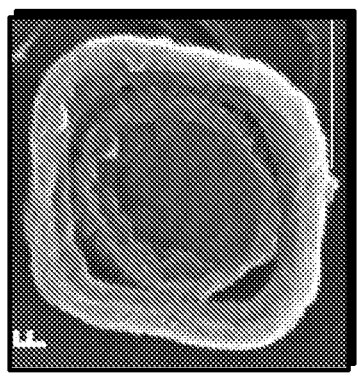
Figure 36G:
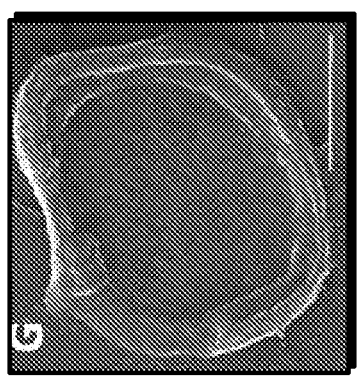
Figure 36H:
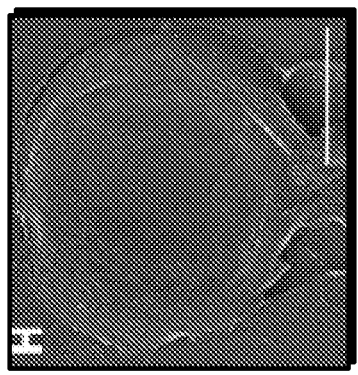

FIGS. 34A-34B presents zeta potential of different surface modified MPS.

FIGS. 35A-35J show agarose modification of nanoporous silicon particles (NSP): NSP observed with SEM at low (FIGS. 35A-35E) and high (FIGS. 35F-35J) magnification: (a and A) bare NSP and (b, c, d and e) agarose coated NSP with different agarose concentration (0.05, 0.125, 0.25 and 0.5% respectively).

FIGS. 36A-36H show silicon particles (NSP) degradation: SEM observation at different times of NSP: bare NSP after (FIG. 36A) 2 hours, (FIG. 36B) 4 hours, (FIG. 36C) 8 hours, (FIG. 36D) 12 hours, (FIG. 36E) 1 day, (FIG. 36F) 2 days, (FIG. 36G) 3 days, and (FIG. 36H) 4 days of incubation with PBS. Scale bar is 1 µm.

Figure 37O:
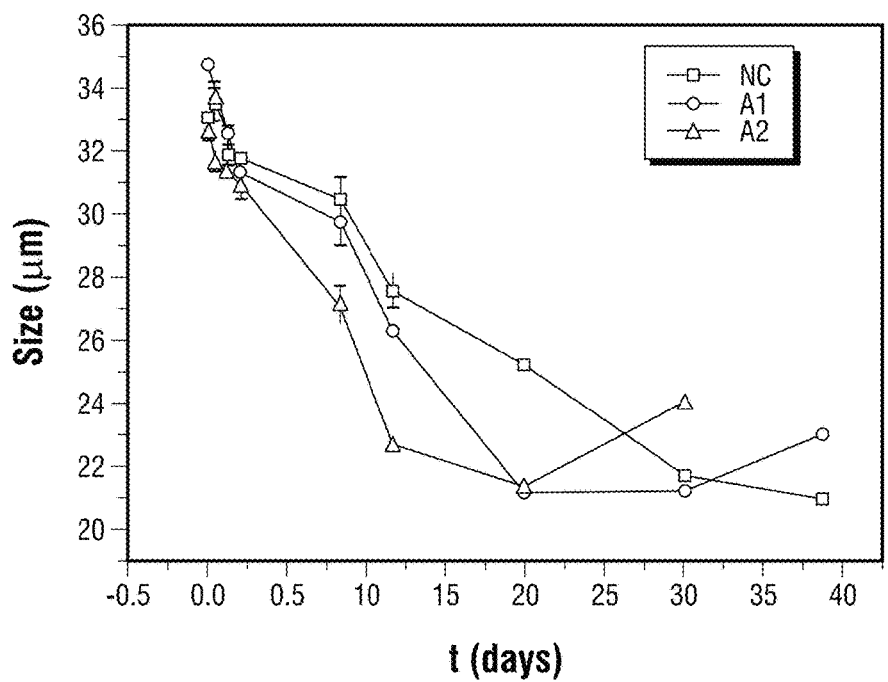
Figure 37P:
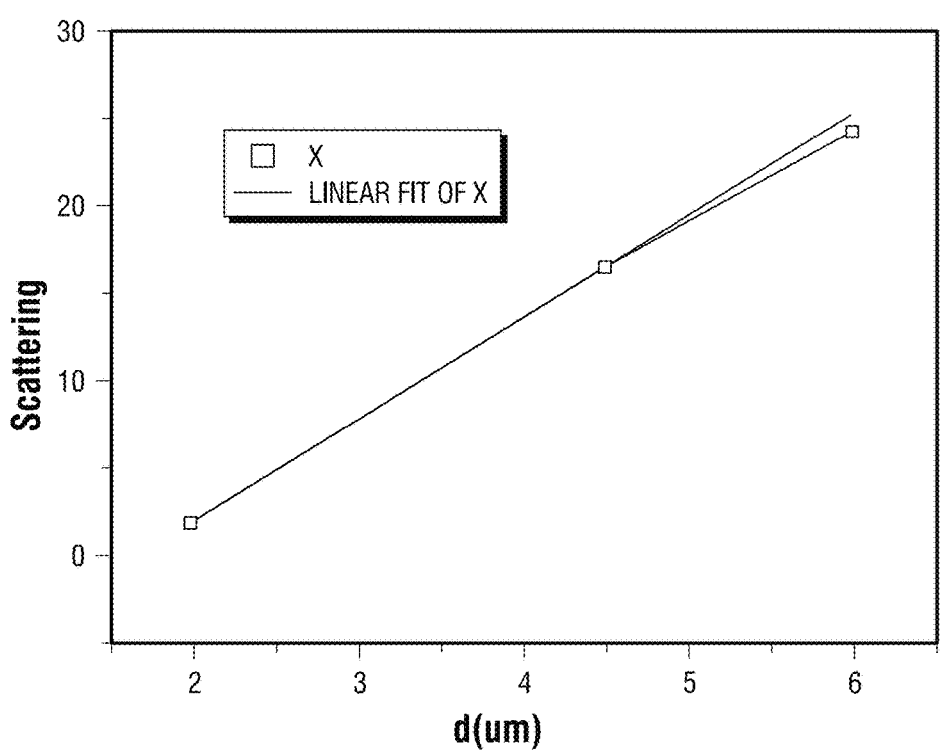

FIGS. 37A-37P show particles degradation as measured through FACS: (FIGS. 37A, 37D, 37H, and 37K) Forward and side scattering data analysis for bare (NC) compared with nanoporous silicon particles coated two agarose concentrations (0.05% agarose concentration (A1) (FIG. 37B, FIG. 37E, FIG. 37I, and FIG. 37L) and 0.125% agarose concentration (A2) (FIG. 37C, FIG. 37F, FIG. 37J, and FIG. 37M), over time (1 h-72 h); (FIG. 37O) size measurements over time of bare (NC) and agarose coated nanoporous silicon particles with two agarose concentrations (0.05% and 0.125%, A1 and A2 respectively); and (FIG. 37P) shows the correlation.

Figure 38A:
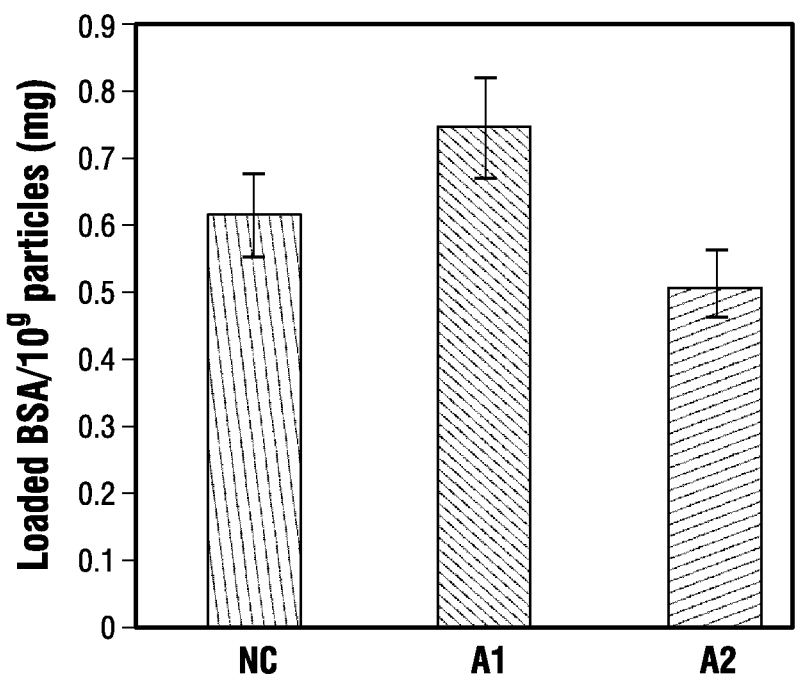
Figure 38B:
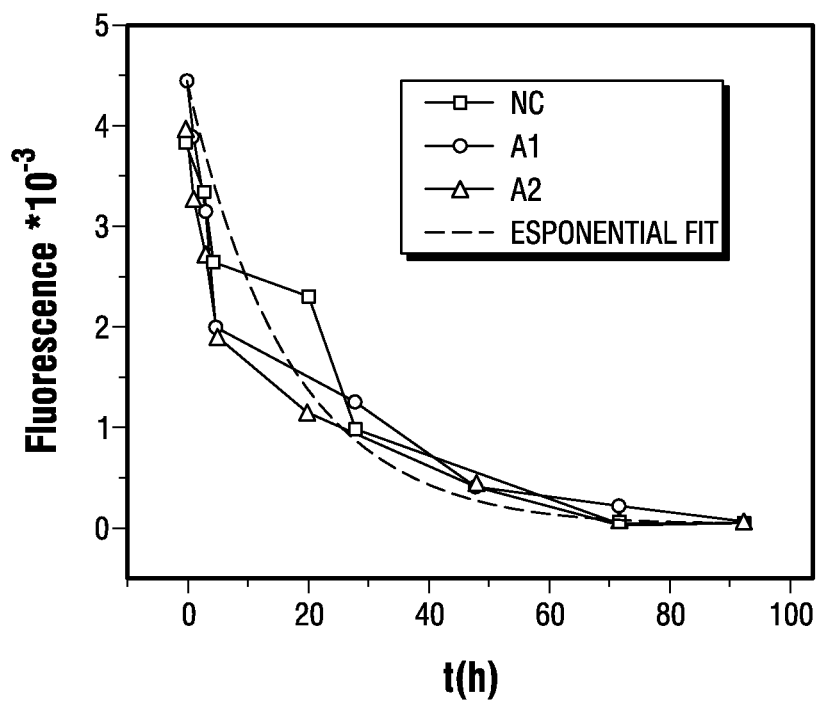
Figure 38C:
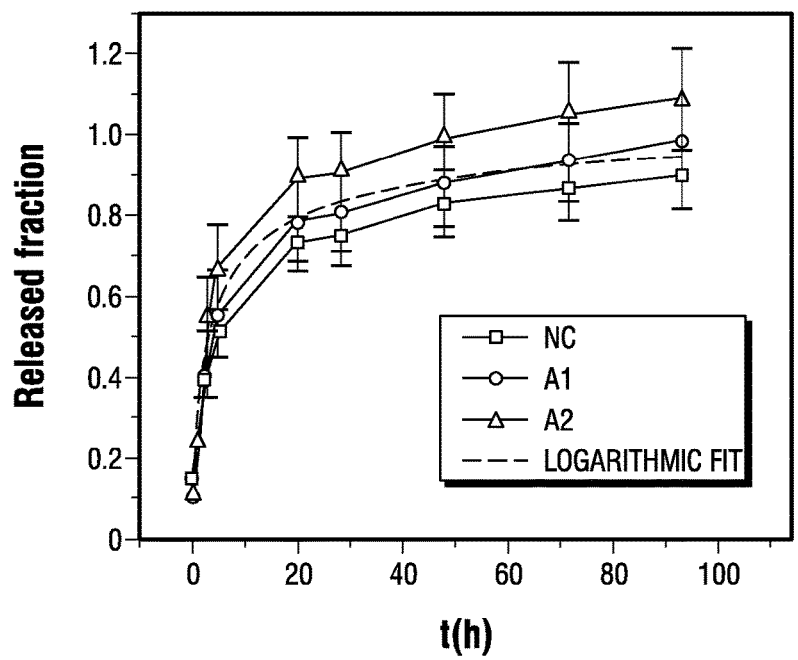

FIGS. 38A-38C show protein load and release: (FIG. 38A) amount of BSA loaded in bare (NC) and agarose coated particles with two agarose concentrations (0.125 and 0.05%, A1 and A2, respectively); (FIG. 38B) fluorescence of agarose coated (A1 and A2) and NC nanoporous silicon particles (NSP), as measured by FACS, and (FIG. 38C) BSA released from agarose coated (A1 and A2) and NC NPS, as measured with spectrofluorimetry.

FIGS. 39A-39D show gel electrophoresis: (FIG. 39A) SDS-page of protein solution released after 24 hours from bare (NC) and agarose coated (Ag) nanoporous silicon particles treated for different times with trypsin (treatment duration in minutes, printed in white on each column) 1, 2 and 3 indicate the most abundant digestion products. (FIG. 39B, FIG. 39C, FIG. 39D) SDS-page relative intensity quantification with ImageJ of trypsin (Tryp), BSA and the three most abundant digestion products (Dig.1, 2 and 3) detected in the protein solution released after 24 hours from bare (NC) and agarose coated (Ag—composition 0.125%) silicon particles after different trypsin treatment duration.

Figure 40A:
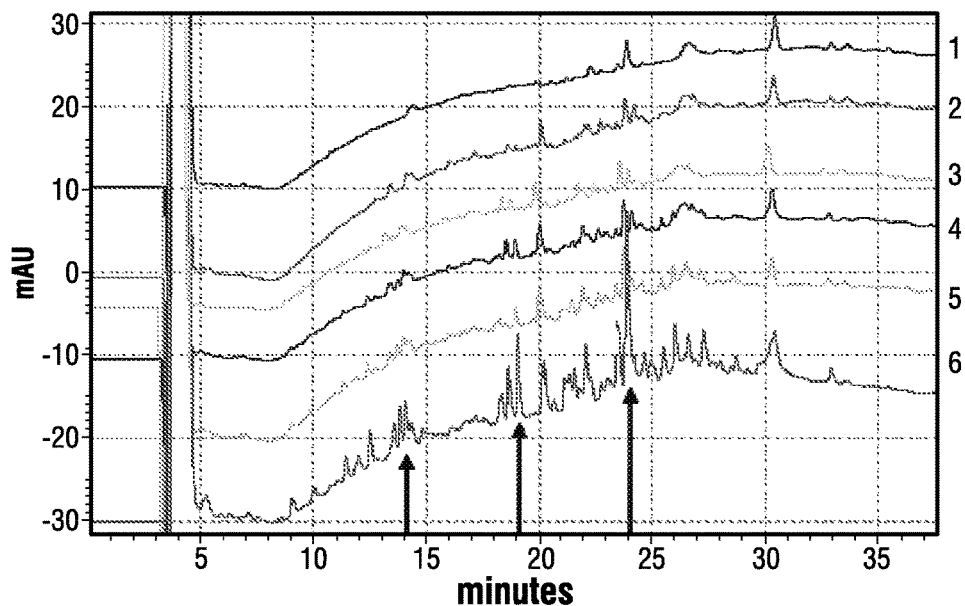
Figure 40B:
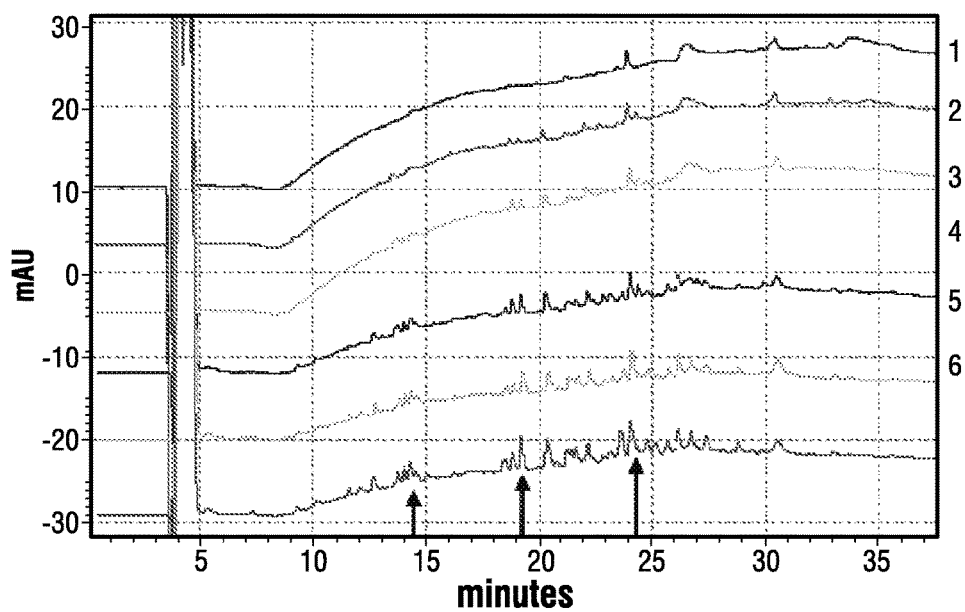

FIGS. 40A-40B show released protein solution chromatography through high pressure liquid chromatography (HPLC) analysis of BSA solution released after 24 hours by (FIG. 40A) NC and (FIG. 40B) Ag particles not treated (blue-1) and treated with trypsin for 15 minutes, 2 hours, 4 hours, 8 hours and 18 hours (green-2, light blue-3, brown-4, light green-5 and pink-6, respectively). Arrows point to three digestion products, the amount of which increases with trypsin treatment time.

FIGS. 41A-41F show in vitro confocal study of cellular internalization of silicon particles (NSP) and protein uptake: (FIG. 41A—control) cells (HUVEC) incubated for 48 hours without NSP; (FIG. 41B) with BSA loaded NSP added into the media; (FIG. 41C) with agarose coated BSA loaded NSEs added into the media; (FIG. 41D) with NC and (FIG. 41E) Ag BSA loaded NSP placed in a transwell on top of the cells, or (FIG. 41F) in BSA solution. White scale bar is 50 µm in FIG. 41A-41C and 10 µm in FIG. 41D-41F.

Figure 42:
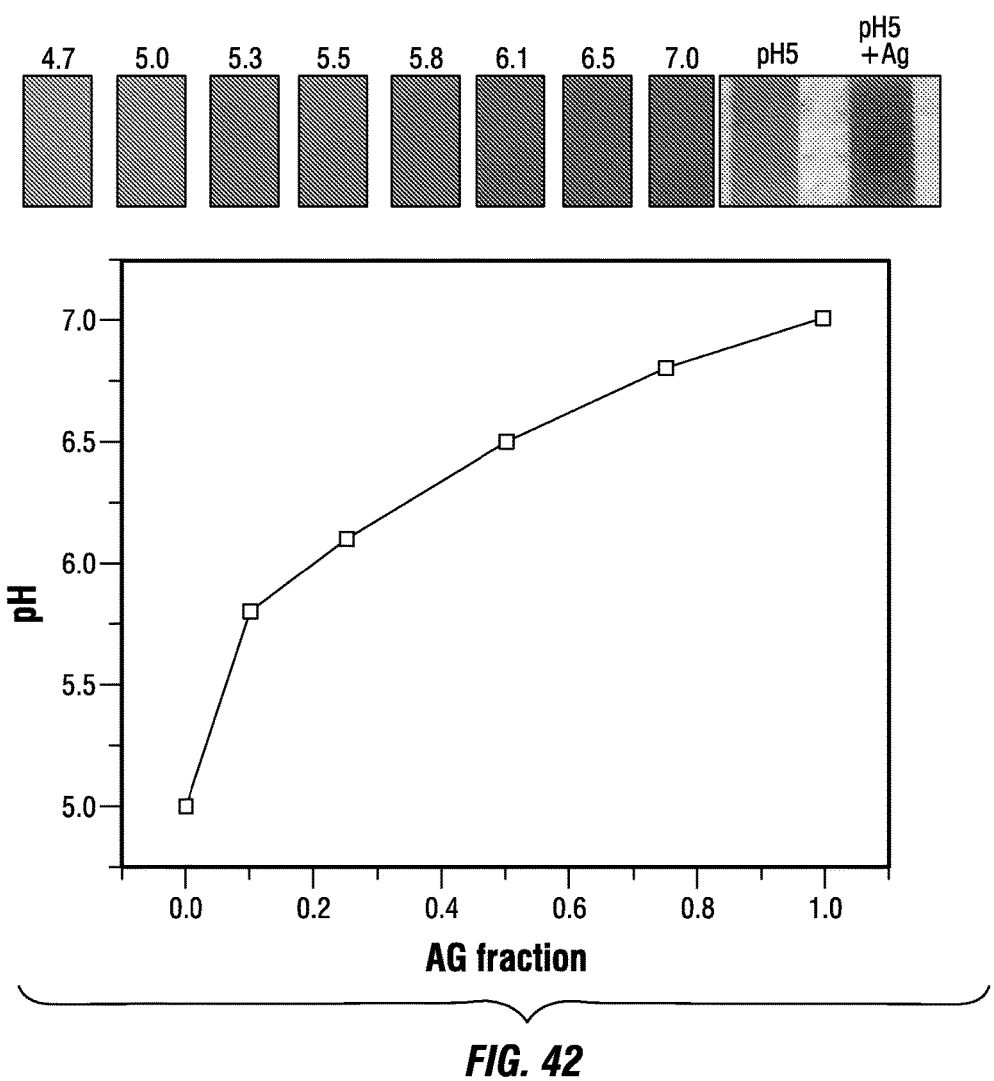
Figure 45A:
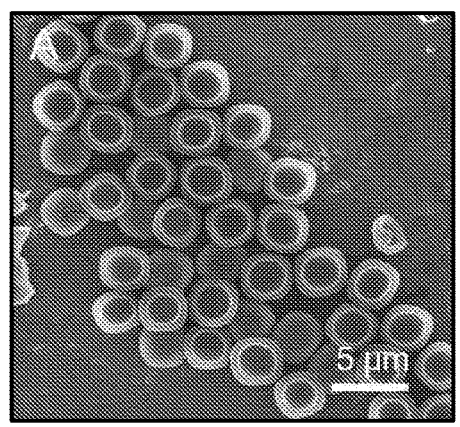
Figure 45B:
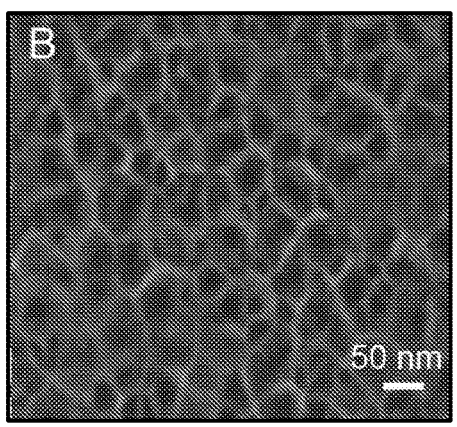
Figure 45C:
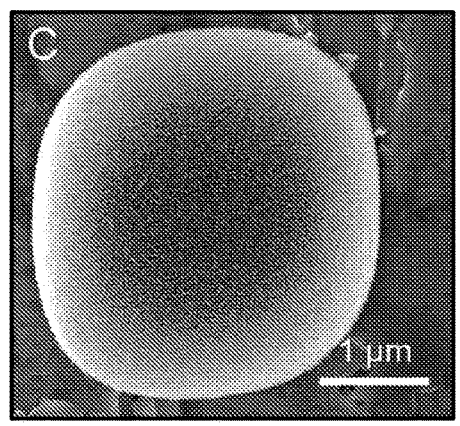
Figure 45D:
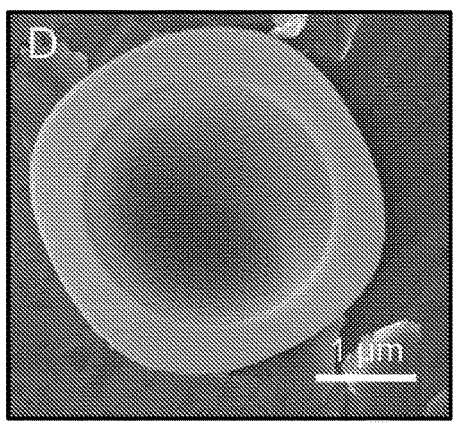

FIG. 42 shows pH measurement of acid solution change due to agarose coating solution.

FIGS. 43A-43F show confocal study of cellular uptake of protein from internalized particles (NSP): HUVEC incubated for (FIG. 43A, FIG. 43C, respectively) 24 hours and (FIG. 43B, FIG. 43D respectively) 48 hours with (FIG. 43A, FIG. 43B) FITC-BSA loaded agarose coated NSP, (43C, 43D) FITC-BSA loaded not coated NSP. Scale bar is 10 µm. FIG. 43E and FIG. 43F show quantification of uptake of BSA within the cells: fluorescence intensity within (FIG. 43E) the nucleus and (FIG. 43B) the cytoplasm of the cells quantified with NIS-Elements. Red square and blue triangle refer to NC and Ag NSP, respectively.

FIGS. 44A-44D are schematic diagrams of PLGA/pSi microspheres fabrication through the S/O/W emulsion method. (FIG. 44A) PLGA/pSi suspension was poured into water phase. (FIG. 44B) The suspension was emulsified in the water phase. (FIG. 44C) Surfactants were added to stabilize the structures. (FIG. 44D) Cartoon depicting the final composition of a PLGA/pSi microsphere (components not in scale).

FIGS. 45A-45D show an SEM image of pSi particles at: (FIG. 45A) lower magnification showing particle uniformity in size and shape; and (FIG. 45B) a higher magnification micrograph revealing the pore structure as seen on the surface of the particle. Low power micrographs illustrate: (FIG. 45C) the front; and (FIG. 45D) rear surfaces of a pSi particle.

FIGS. 46A-46D show a physical characterization and size distribution of PLGA/pSi microspheres. (FIG. 46A) SEM image of presorted microspheres. (FIG. 46B) An optical microscopy image shows the presence of pSi particles (arrows) enclosed in the larger PLGA spheres. (FIG. 46C) Fluorescence microscope, and (FIG. 46D) the size distribution of PLGA/pSi microspheres displays the uniform product centered around 24.5 µm.

FIGS. 47A-47E show a FACS analysis of nonsorted and sorted PLGA/pSi microspheres prepared with 488-DyLight conjugated pSi particles (DyLight-PLGA/pSi microspheres): (FIG. 47A) the percent of DyLight-PLGA/pSi microspheres in the non-sorted, sorted microspheres and supernatant; (FIG. 47B) the mean fluorescence of the sorted, nonsorted microspheres, and the supernatant; (FIG. 47C) fluorescence intensity and distribution of 488-DyLight conjugated pSi particles (light green), nonsorted microspheres (blue), sorted microspheres (dark green), and supernatant solution (black). Also shown are confocal images of (FIG. 47D) nonsorted microspheres and (FIG. 47E) sorted microspheres.

FIGS. 48A-48D show release profiles of FITC-BSA from various examined PLGA/pSi microsphere formulations, including: (FIG. 48A) total FITC-BSA released over 27 days; (FIG. 48B) first three day release; (FIG. 48C) day 5 to 15 release; and (FIG. 48D) day 15 to 27 release.

Figure 49A:
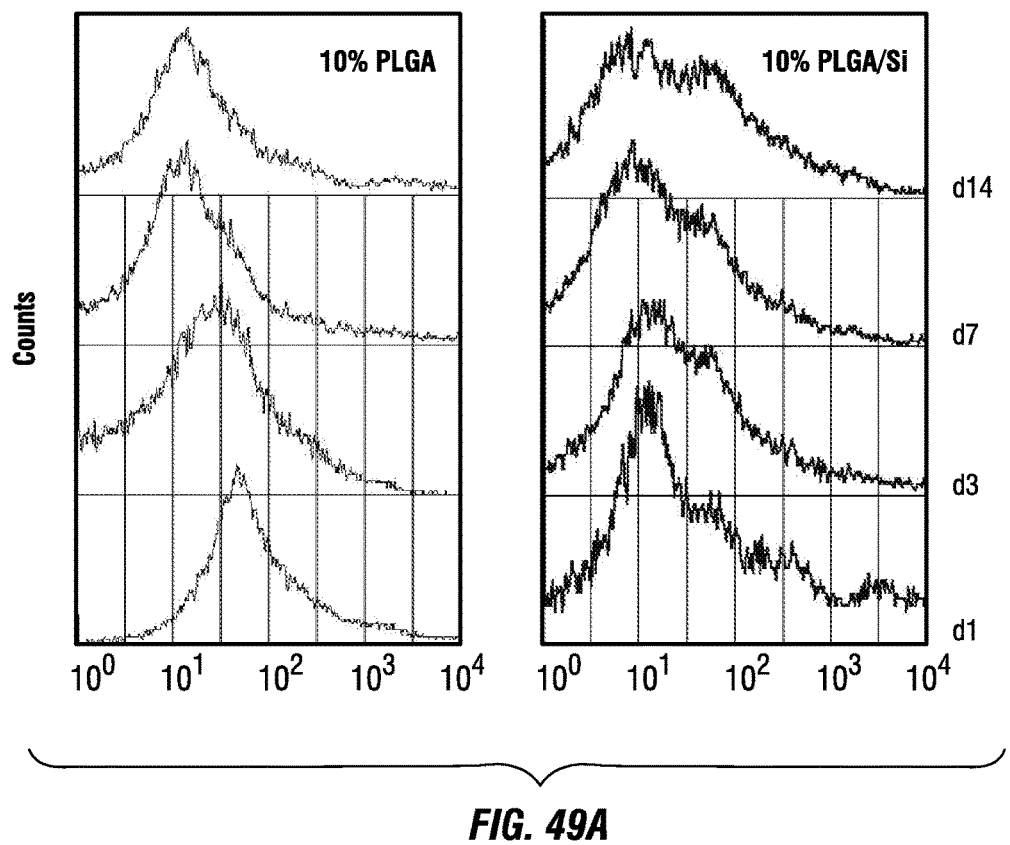
Figure 49B:
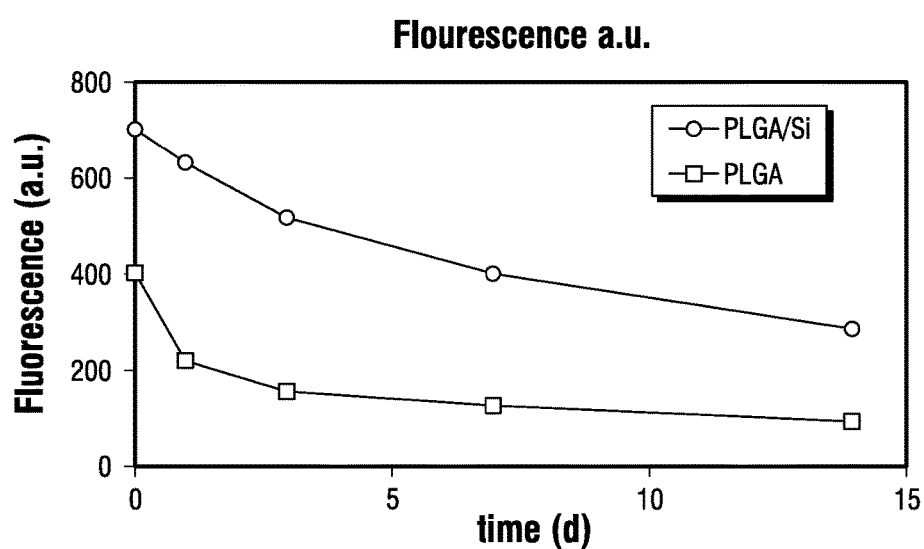
Figure 50A:
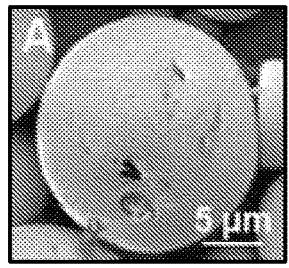
Figure 50B:
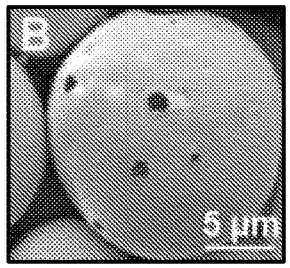
Figure 50C:
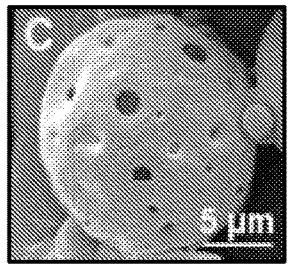
Figure 50D:
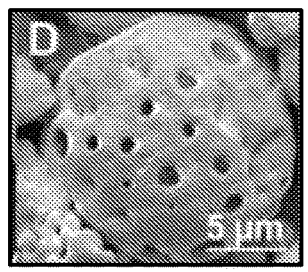
Figure 50E:
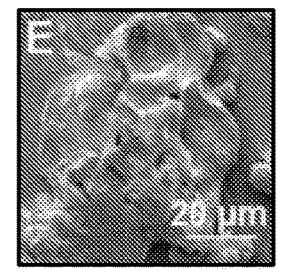
Figure 50F:
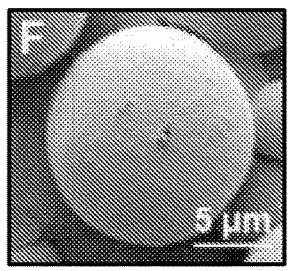
Figure 50G:
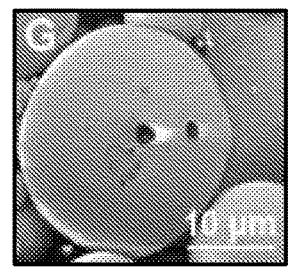
Figure 50H:
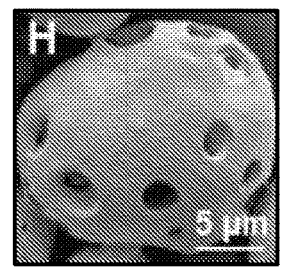
Figure 50J:
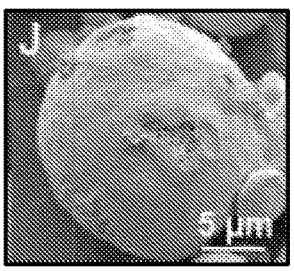
Figure 50K:
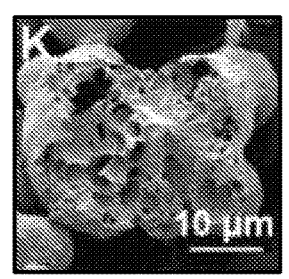
Figure 50L:
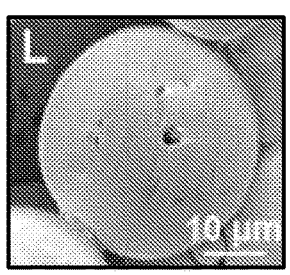
Figure 50M:
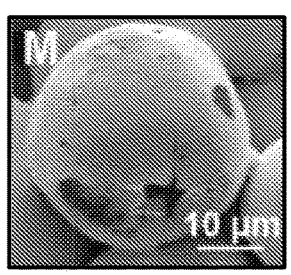
Figure 50N:
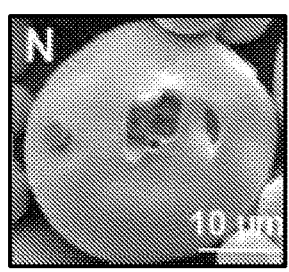
Figure 50O:
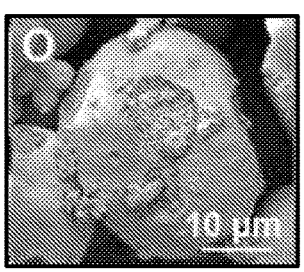
Figure 50P:
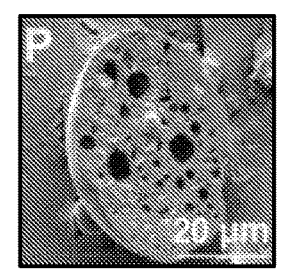

FIGS. 49A-49B show PLGA and PLGA/pSi microspheres analyzed via FACS during in vitro release.

FIG. 49A shows histographic overlay of the fluorescence intensity and distribution of control PLGA (left) and PLGA/pSi (right) over 2 weeks of incubation in PBS.

FIG. 49B shows decrease of fluorescence intensity as measured through FACS dropped to minimum at day 3 in control PLGA. PLGA/pSi showed slow decrease in fluorescence intensity and displayed 3 fold the intensity of control at 2 weeks.

FIGS. 50A-50H and FIGS. 50J-50P show SEM images of PLGA/pSi microsphere degradation over 1, 2, 3, 4, and 6 weeks with 6% coating (FIGS. 50A-50E), 10% coating (FIGS. 50F-50H and FIGS. 50J-50K), or 20% coating (FIGS. 50L-50P).

Figure 51A:
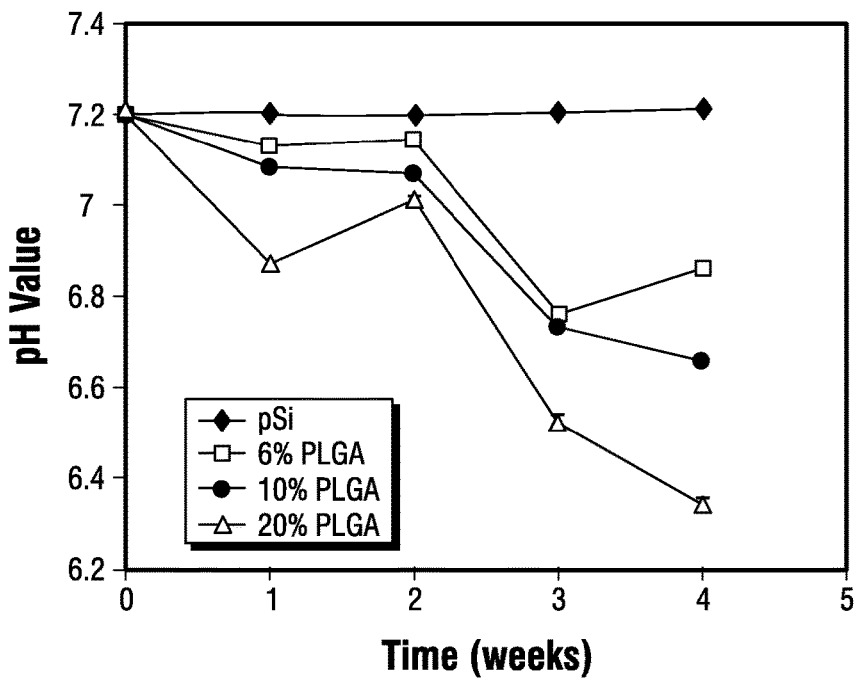
Figure 51B:
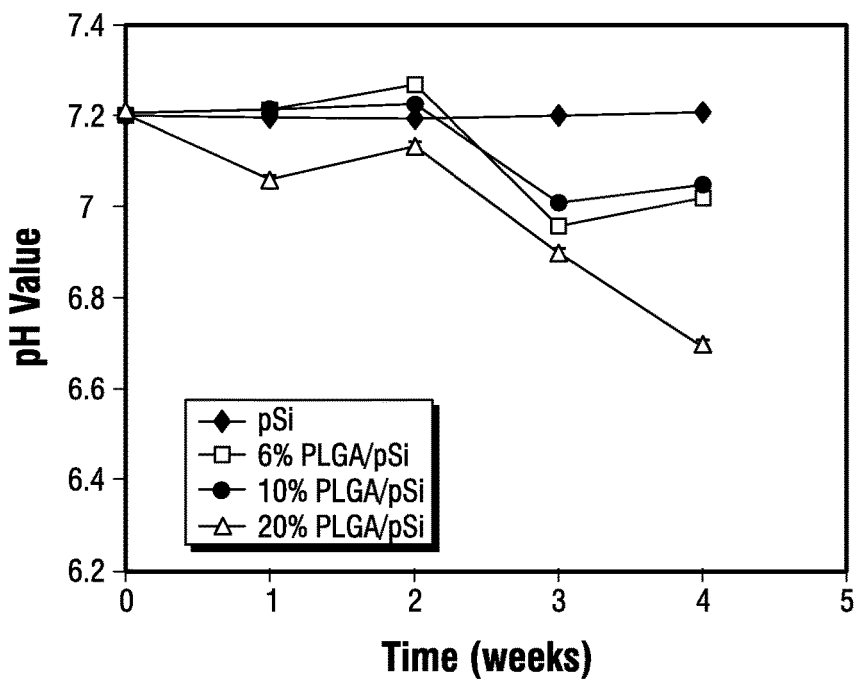

FIGS. 51A-51B show the pH of pSi, PLGA, and PLGA/pSi microsphere degradation byproducts in PBS at 37° C. over 4 weeks for (FIG. 51A) PLGA-only microspheres (control) and (FIG. 51B) PLGA/pSi microspheres.

Figure 52:
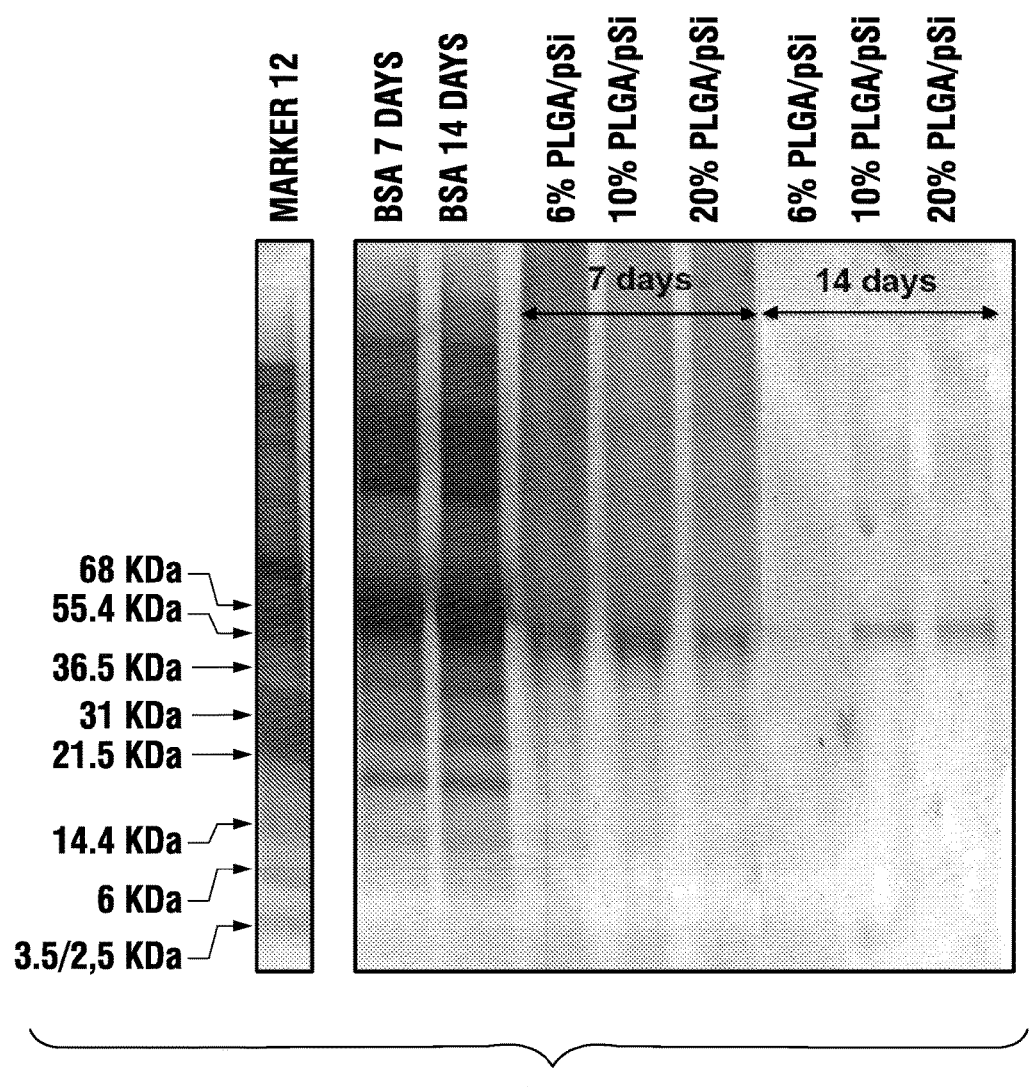

FIG. 52 shows FITC-BSA degradation over 2 weeks. SPS-PAGE of release products showed BSA (approximately 68 kDa) released from PLGA/pSi microspheres suffered no degradation bands compared to controls (BSA in solution for 7 and 14 days, columns 2 and 3, respectively).

FIGS. 53A-53G show mineralization on the surface of PLGA/pSi microspheres, including SEM images of (FIG. 53A, FIG. 53C) PLGA and (FIG. 53B, FIG. 53D) PLGA/pSi microspheres in osteogenic media after 3 and 21 days, respectively. Also shown are (FIG. 53E-FIG. 53F) SEM images at day 21 at higher magnification. In addition, the (FIG. 53G) EDX spectrum of mineralized PLGA/pSi microspheres on day 3 (gray dot line) and day 14 (black solid line) is shown.

FIGS. 54A-54J show confocal microscopy images of PLGA/pSi microparticles (loaded with green fluorescent BSA) were not internalized by bone marrow derived stromal cells (BMSCs) at (FIGS. 54D-54G) 0 hour, (FIGS. 54E-54H) 48 hours, or (FIGS. 54F-54I) 120 hours, while (FIG. 54G) pSi microparticles were internalized by BMSCs at 0.5 hours (FIG. 54A), 48 hours (FIG. 54B), and 120 hours (FIG. 54C).

FIG. 54J shows a schematic diagram of the mechanism of action of PLGA/pSi microspheres compared to pSi. Following internalization, pSi is trapped within lysosomes, while the PLGA/pSi particles are not endocytosed by BMSC and release their payload outside the cells where it can exert its bioactive function and trigger nuclear changes through the classic mechanism of signal cascade.

FIGS. 55A-55E show confocal images of stained HUVEC (green-BSA, red-actine filaments, blue-nuclei) after 7 days in culture (FIG. 55A, FIG. 55B—control, BSA in solution), or after incubation with BSA loaded PLGA/pSi microspheres (FIG. 55C, FIG. 55D), with overlap of all three fluorescent channels (FIG. 55A and FIG. 55C), or bright field and green channels (FIG. 55B and FIG. 55D). Average fluorescence intensity of the three fluorescent channels (FIG. 55E) related to control HUVEC (dark color bars) and HUVEC incubated with PLGA/pSi (light color bars) as measured at the confocal microscope are also shown.

Figure 56:
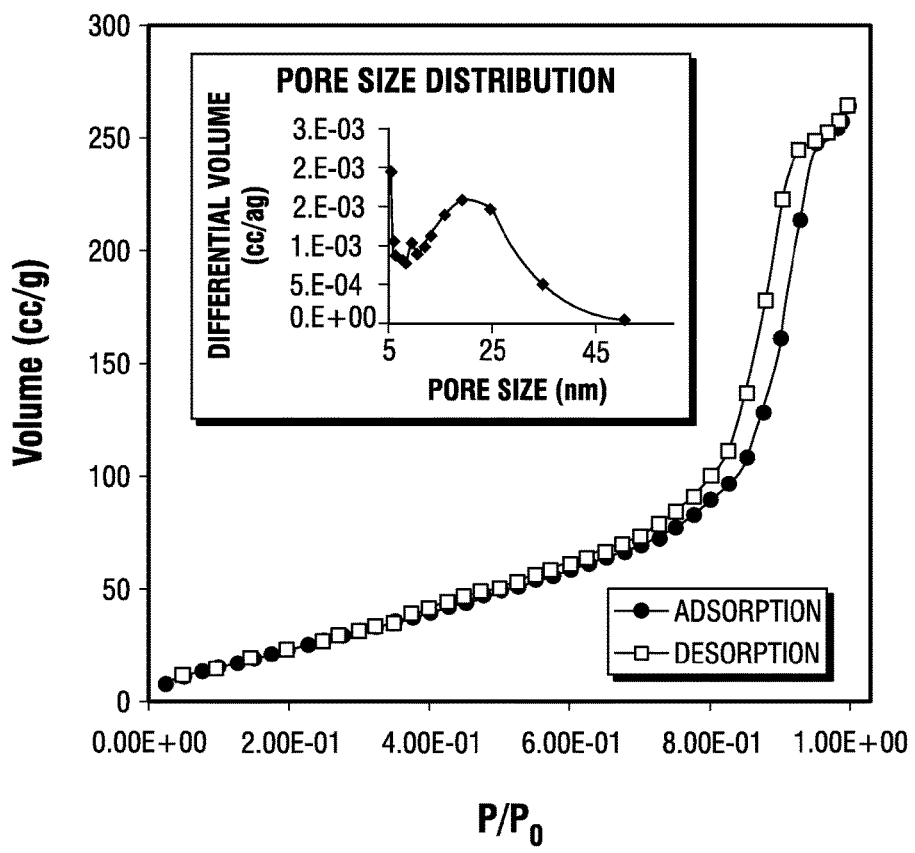

FIG. 56 shows an analysis of the porous structure of MP2 porous silicon microparticles by nitrogen adsorption-desorption isotherms at 77K. The inset graph shows pore size distribution according to the Barrett-Joyner-Halenda model.

Figure 57:
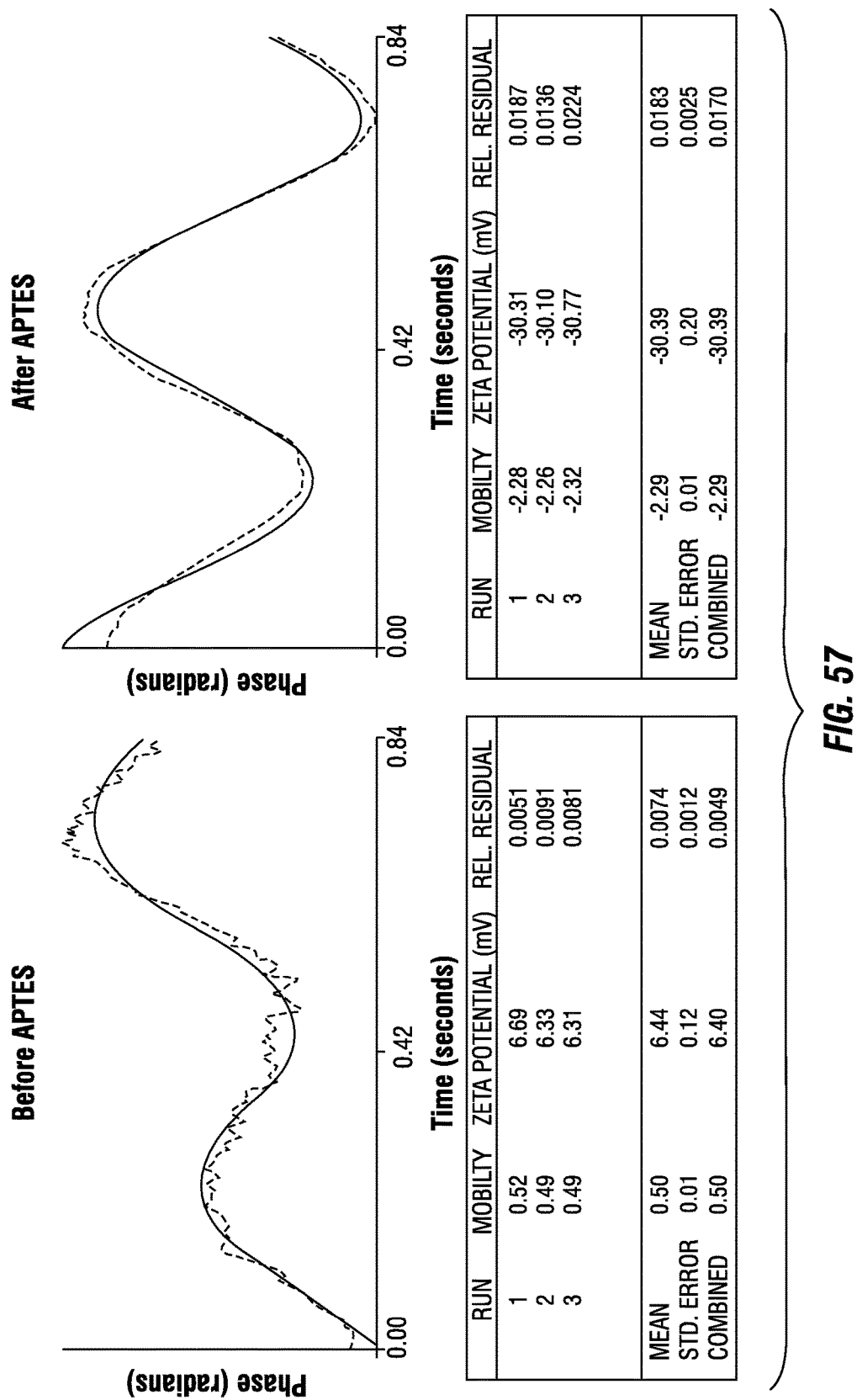

FIG. 57 shows Zeta potential analysis indicating that the oxidized pSi surface had a surface charge of $-30.39$ My (left panel), while the APTES modified pSi particles had a value of 6.44 mV(right panel).

Figure 58:
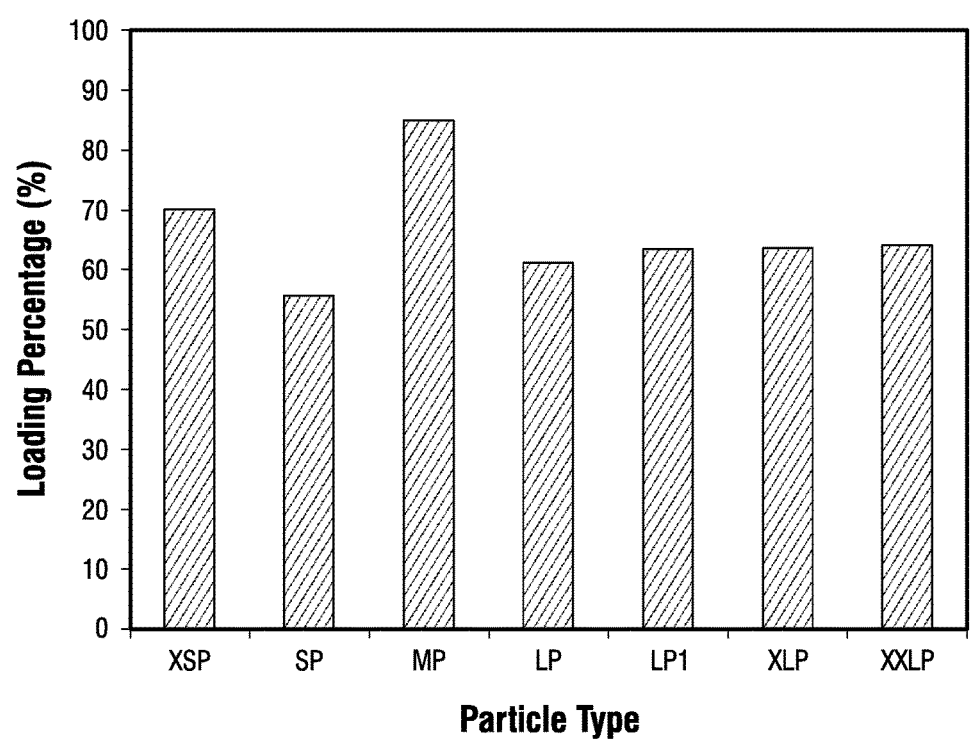

FIG. 58 shows the loading efficiency of seven different types of pSi particles. For a certain concentration of FITC-BSA solution, mesoporous silicon particles has the highest loading efficiency.

DETAILED DESCRIPTION OF EXEMPLARY EMBODIMENTS

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Definitions

Unless otherwise specified "a" or "an" means one or more.

"Microparticle" means a particle having a maximum characteristic size from 1 micron to 1000 microns, or from 1 micron to 100 microns.

"Nanoparticle" means a particle having a maximum characteristic size of less than 1 micron.

"Nanoporous" or "nanopores" refers to pores with an average size of less than 1 micron.

"Biodegradable material" refers to a material that can dissolve or degrade in a physiological medium, such as PBS or serum.

"Biocompatible" refers to a material that, when exposed to living cells, will support an appropriate cellular activity of the cells without causing an undesirable effect in the cells such as a change in a living cycle of the cells; a release of proinflammatory factors; a change in a proliferation rate of the cells and a cytotoxic effect.

APTES stands for 3-aminopropyltriethoxysilane.

Loading capacity or loading efficiency refers to an amount of a load that can be contained in pores of a porous object.

Introduction

Insufficient healing occurring in cases of traumatic fractures or injuries may be substantial. For instance, severe leg injuries are typically repaired with bone grafts. Pins, plates or screws hold the grafts to healthy bone while external fixation provides support. However, it may take months to years before the injured patient fully recovers. Therefore, a technology that provides both immediate mechanical stability to restore function and accelerates the regeneration process is needed.

The ideal tissue engineering scaffold may require several characteristics. Such characteristics may include biocompatibility, biodegradability, mechanical stability, interconnected porosity and the ability to deliver active agents, such as therapeutic and/or imaging agents. To achieve such properties, one may combine diverse technologies into a multifunctional composite materials. For instance, it is well known in the field of tissue engineering (TE) that the porosity and pore interconnectivity of the scaffold may be essential for tissue in-growth, vascularization and nutrient supply. However, high porosity may severely compromise mechanical properties. The challenge may lie in the trade-off between porosity and mechanical integrity, wherein porosity is usually negatively correlated with mechanic al strength.

The present disclosure presents a strategy for conquering the challenge of meeting mechanical requirements of tissue engineering scaffolds while maintaining the porous structure necessary for tissue integration and supplying of essential bioactive molecules for accelerated tissue regeneration. In some embodiments, the present invention provides compositions that comprise: (1) a biodegradable polymer matrix; and (2) at least one biodegradable reinforcing particle that is dispersed in the matrix. In additional embodiments, the compositions of the present invention further comprise a (3) porogen particle that is also dispersed in the matrix. In further embodiments, one or more of the above-mentioned individual components are associated with an active agent.

In further embodiments, the compositions of the present invention may be utilized as scaffolds, such as scaffolds for treating bone defects. Accordingly, in various embodiments, the present invention also provides methods of treating a bone defect in a subject by applying to an area of the bone defect in the subject a scaffold of the present invention. Further embodiments of the present invention pertain to methods of making the compositions of the present invention.

As discussed in more detail below, the methods and compositions of the present invention have numerous applications and advantages. More detailed aspects of various embodiments of the present invention will now be described below as specific and non-limiting examples.

Biodegradable Polymer Matrix

In the present invention, biodegradable polymer matrices generally refer to polymer-based matrices that show at least some biodegradability. In various embodiments, the biodegradable polymer matrices of the present invention may comprise a biodegradable polymer. Non-limiting examples of suitable biodegradable polymers include collagen, gelatin, alginate, polycaprolactone, and poly(lactic-co-glycolic acid) (PLGA).

In many embodiments, the biodegradable polymer may be an unsaturated biodegradable polymer (i.e. a biodegradable polymer containing at least one unsaturated carbon-carbon bond, such as a double or a triple bond). Such unsaturated polymers may be cross-linkable in situ. Non-limiting examples of unsaturated biodegradable polymers include poly(propylene fumarate) (PPF), poly(E-caprolactone-fumarate), and mixtures and co-polymers thereof.

Additional biodegradable polymers that may be used in the polymer matrices of the present invention are disclosed, for example, in WO 2010/040188; WO2006/023130; WO1997/045532; US2005/0177249; US2006/026335; U.S. Pat. Nos. 6,858,229, 5,522,895, 6,281,257, and 6,124,373; Mano et al. Composites Science and Technology. 2004. 64:789-817; Rezwan et al. Biomaterials. 2006. 27:3413; Boccaccini et al. Expert Review of Medical Devices. 2005. 2(3):303; Advanced Drug Delivery Reviews. 2007. 59(4-5): 249; and Tan et al. Materials. 2010. 3:1746; J R Soc. Interface. 2007. 4(17): 999-1030.

As set forth in more detail below, the biodegradable polymer matrices of the present invention may be associated with one or more active agents. Furthermore, the biodegradable polymer matrices of the present invention may be associated with biodegradable reinforcing particles and porogen particles.

In a more specific embodiment, the biodegradable polymer matrix comprises PPF. By way of background PPF is an example of an in situ cross-linkable polymer that exhibits mechanical properties close to the ones of the trabecular bone. See, e.g. Peter et al. J Biomed Mater Res. 1999; 44: 314-21. As set forth in more detail below, these properties of PPF's in the biodegradable polymer matrices of the present invention may be further amplified by the use of biodegradable reinforcing particles, porogen particles and active agents.

Biodegradable Reinforcing Particles

In the present invention, biodegradable reinforcing particles generally refer to particles of the nano scale that provide mechanical strength to the surrounding polymer matrix. Biodegradable reinforcing particles may also simultaneously release active agents upon biodegradation. Generally, the biodegradable reinforcing particles of the present invention are dispersed in the biodegradable polymer matrix and selected from the group consisting of porous oxide particles and porous semiconductor particles.

A person of ordinary skill in the art will recognize that various suitable biodegradable reinforcing particles may be used in the present invention. Non-limiting examples of suitable biodegradable reinforcing particles include biodegradable oxide microparticles or nanoparticles (e.g., silica particles), or biodegradable semiconductor microparticles or nanoparticle (e.g., silicon particles). In many embodiments, the biodegradable reinforcing particles of the present invention may comprise porous or mesoporous microparticles or nanoparticles, such as mesoporous silica or silicon particles. In some embodiments, the biodegradable reinforcing particles may comprise nanoporous microparticles or nanoparticles.

In various embodiments, the biodegradable reinforcing particles of the present invention may also be associated with an active agent. Non-limiting examples of suitable active agents include degradation inducers of the porogen particles, imaging agents (e.g., barium sulfate), proteins, platelet rich plasma, cell viability enhancing agents (e.g., glucose), anti-inflammatory agents, antibiotics, therapeutic agents, growth factors, DNA, siRNA, and the like. Such active agents may also include: agents that can prevent an infection at a site of a bone defect, such as a bone fracture; agents that can contribute to bone regeneration at a site of a bone defect; and agents that can contribute to cell viability at a site of a bone defect.

In more specific embodiments, the biodegradable reinforcing particles of the present invention contain an imaging agent, which may facilitate imaging and/or monitoring of a site of a bone defect, such as a bone fracture. One non-limiting example of such an imaging agent may be barium sulfate, which may facilitate X-ray imaging of a bone defect site.

In more specific embodiments, biodegradable reinforcing particles that comprise porous microparticles or nanoparticles (reinforcing microparticles or nanoparticles) may contain one or more active agents, such as therapeutic and/or imaging agents that may be released upon the degradation of the particles. The active agents which may be contained inside the reinforcing microparticles or nanoparticles may include, without limitation, antibiotics, anti-inflammatory agents, proteins (such as growth factor), and nucleic acids (such as DNA and siRNA). In some embodiments, the growth factors may include one or more of PDGFαβ, PDGFαα, PDGFββ, TGF1, TGF2, vascular endothelial growth factor (VEGF) and/or epithelial growth factor (EGF).

In some embodiments, the reinforcing microparticles or nanoparticles may contain one or more proteins, such as fibrin, fibronectin and vitronectin. In some embodiments, the reinforcing microparticle or nanoparticle may contain platelet-rich plasma (PRP). PRP may contain PDGFαβ, PDGFαα, PDGFββ, TGF1, TGF2, VEGF, EGF, fibrin, fibronectin and/or vitronectin. In some embodiments, the reinforcing microparticles or nanoparticles may contain a cell viability enhancing agent, which may be, for example, a sugar, such as glucose or glucose derivative, such as glucose lactam. In some embodiments, the reinforcing microparticles or nanoparticles may contain a bone loss preventing agent, which may be, for example, a biphosphonate, such as etidronate, clodronate, tiludronate, pamidronate, neridronate, olpadronate, alendronate, ibandronate, risendronate, or zolendronate.

In some embodiments, the reinforcing microparticles or nanoparticles may contain one or more imaging agents, which may used for imaging or monitoring the treated bone defect site. Such imaging agents may include, but not be limited to X-ray contrast agents, such as barium sulfate; MRI contrast agents; ultrasound contrast agents; fluorescent agents, such as fluorescent dyes and quantum dots; and metal nanoparticles. In more specific embodiments, the reinforcing microparticle or nanoparticle is a mesoporous silica particle, and the active agent is an imaging agent that is embedded into the matrix of the silica particle.

In various embodiments, the biodegradable reinforcing particles may constitute from 1% to 30%, from 2% to 25%, from 3% to 20%, or from 5% to 15% of the volume of the composition (or any sub-range within these ranges).

In many embodiments, biodegradable reinforcing particles may be anisotropic particles (i.e. particles that have one of their dimensions (e.g., length or thickness) substantially different from the other two, which may define a cross-section of the particle).

An aspect ratio of the biodegradable reinforcing particle may be defined as a ratio between the length or thickness and its mean lateral dimension (i.e., mean dimension of its cross-section). Such a mean lateral dimension may be a diameter of a circular cross-section, a side-length for a square cross-section, or a square root of a product of two lateral dimensions for structures that have a cross-section characterized by two dimensions (such as a rectangular cross-section or an elliptical cross-section). For the anisotropic particle, the aspect ratio is substantially different than 1.

In many embodiments, the biodegradable reinforcing particle may be an elongated, rod-like particle. In some embodiments, the biodegradable reinforcing particles have an aspect ratio of at least 2, at least 4, at least 10, at least 20, at least 50, at least 100, at least 200, at least 500, or at least 1000. Such elongated particles may be prepared using the methods disclosed in the Examples below. Such elongated particles may be also be prepared using the techniques disclosed in U.S. patent application Ser. No. 13/044,250 and PCT Application No. PCT/US11/27746.

In various embodiments, biodegradable reinforcing particles of the present invention may have a cross-section having the greater of lateral dimension(s) of no more than 10 microns, no more than 5 microns, no more than 2 microns, no more than 1 micron, no more than 500 nm, no more than 200 nm, no more than 100 nm, or no more than 50 nm. In many embodiments, the smaller of the lateral dimension(s) of the biodegradable reinforcing particles' cross-section is no more than 5 microns, no more than 2 microns, no more than 1 micron, no more than 500 nm, no more than 200 nm, no more than 100 nm, or no more than 50 nm. In many embodiments, the smaller of the lateral dimension(s) of the cross-section of the biodegradable reinforcing particles may be no more than 5 microns, no more than 2 microns, no more than 1 micron, no more than 500 nm, no more than 200 nm, no more 100 nm, or no more than 50 nm.

The cross-section of the biodegradable reinforcing particles of the present invention may have a variety of shapes. In some embodiments, the cross-section may be circular or elliptical. In some embodiments, the cross-section may be rectangular. Considerations for selecting shapes and sizes of reinforcing particles are disclosed, for example, in Ranganathan et al. Acta Biometer. 2010. 6(9):3448-56. Epub 2010 Mar. 24.

In many embodiment, the biodegradable reinforcing particles may be integrated in the biodegradable polymer matrix. Such integration may be involve covalently binding the reinforcing particles with the polymer matrix. For such covalent binding, the reinforcing particles may comprise a chemical moiety that is capable of covalently bonding to the biodegradable polymer. One non-limiting example of such a chemical moiety may be an acrylate. In some embodiments, the chemical moiety may be introduced on a surface of the biodegradable reinforcing particles after the particles are fabricated or synthesized. Yet, in some other embodiments, the chemical moiety may be introduced into the biodegradable reinforcing particles during their fabrication or synthesis.

Porogen Particles

In the present invention, porogen particles generally refer to biodegradable particles of the micron scale that are dispersed in the polymer matrix. In addition, the porogen particles of the present invention may be associated with one or more active agents. Upon degradation, the porogen particles of the present invention may leave interconnected porosity throughout the matrix while simultaneously releasing active agents (e.g., cells). In addition, the porogen particles of the present invention may contain within them additional particles, such as biodegradable porous particles (e.g., silicon porous particles).

In various embodiments, the porogen particles of the present invention (including any particles within the porogen particles) may be hydrogel porogen particles (e.g., alginates, fibrins, and gelatins), natural or synthetic biodegradable particles (e.g., particles derived from or coated with poly(lactic-co-glycolic acid) (PLGA)), biodegradable porous particles (e.g., silicon porous particles), and biocompatible vesicles (e.g., liposomes and/or micelles).

In various embodiments, a surface of a porogen particle (or a surface of a particle within the porogen particle) is modified with a biodegradable polymer. In some embodiments, the biodegradable polymer is agarose. In further embodiments, the biodegradable polymer is PLGA. In more specific embodiments, porogen particles contain biodegradable porous particles within them (e.g., silicon porous particles) that are coated with a biodegradable polymer (e.g., PLGA and/or agarose).

Without being bound by theory, Applicants envision that porogen particles of the present invention can help facilitate or control various properties of the compositions of the present invention. For instance, in some embodiments, porogen particles may help facilitate or control the bio-distribution of active agents to various parts of an organism (e.g., cells, tissues, organs, etc.).

In further embodiments, porogen particles can help facilitate or control the intracellular delivery of active agents to various organelles (e.g., lysosomes, cytoplasm and nuclei). For instance, in some embodiments, porogen particles can prevent or guide particles to lysosomes, cytoplasms, nuclei or other cellular organelles.

In addition, porogen particles may help facilitate the internalization of the particle by various cells and organelles. For instance, in some embodiments, an agarose coating on a biodegradable porous particle within a porogen particle may help enhance active agent delivery to the nuclei of cells.

In additional embodiments, porogen particles of the present invention may help facilitate, preserve or control the stability of active agents. For instance, in cases where the active agent is a protein, porogen particles of the present invention may help prolong protein stability by preserving protein structure over time and protecting the protein from enzymatic digestion.

In some embodiments, the porosity and pore interconnectivity within the compositions of the present invention may be created in vivo using porogen particles. In some embodiments, the porogen particles may have the ability to encapsulate cells, such as stem cells, an/or active agents, such as therapeutic and/or imaging agents. In some embodiments, the porogen particles may contain or encapsulate one or more proteins. For example, in certain embodiments, plateletrich plasma (PRP), which is a blood derived liquid that may provide proper ECM-like protein for cellular attachment and release one or more native factors from platelets to recruit and proliferate cells, may be integrated or incorporated within the porogen particles. Such incorporation may contribute to obtaining a desired size of the porogen particles, which may be from 100 microns to 700 microns, from 150 microns to 600 microns, or from 200 microns to 500 microns. Such incorporation may also provide a sustained release of growth factors from the porogen particles.

In various embodiments, the porogen particles of the present invention may degrade in a body of a patient with a rate faster than a biodegradation rate of the biodegradable polymer of the matrix, thereby forming a porous network in the matrix. In some embodiments, such a porous network may be necessary for formation of new vasculature at a bone defect site. In some embodiments, the biodegradation rate of the porogen particles may be no more than 3 months, no more than 2 months, no more than 1 month, no more than 2 weeks, no more than 10 days, no more than 7 days, no more than 6 days, no more than 5 days, no more than 4 days, no more than 3 days, no more than 2 days, or no more than 1 day.

In various embodiments, the porogen particles of the present invention may have a characteristic size, such as a diameter that may range from 100 microns to 700 microns, from 150 microns to 600 microns, or from 200 microns to 500 microns. In further embodiments, the porogen particles of the present invention may constitute from 20% to 95%, from 25% to 90%, from 30% to 80%, or from 35% to 75% of the volume of the composition.

In more specific embodiments, the porogen particles of the present invention (or any particles within them) may be hydrogel porogen particles (i.e. particles comprising a natural or synthetic hydrogel). Examples of natural hydrogels include hydrogels based on natural biodegradable polymers, such as gelatin or collagen. Examples of synthetic hydrogels include hydrogels based on synthetic biodegradable polymers, such as oligo(poly (ethylene glycol) fumarate (OPF).

In some embodiments, the hydrogel material in the porogen particle may comprise a polysaccharide polymer. In some embodiments, the hydrogel material may be an anionic polysaccharide, such as alginate. Various suitable porogen particles (including alginate) are disclosed in WO2005/020849, US2008/0206308, U.S. Pat. No. 6,656,508, US 2002/0001619, US 2002/0168406, WO2008/006658, WO2008/073856, EP1664168, US2007/0178159, and WO2007/089997.

In some embodiments, the hydrogel-based porogen particles may contain a metal ion, which may be replaced or dissociated from the complex to facilitate a degradation of the porogen particle. Such a replacement may be initiated by a degradation initiator, such as a chelation agent. The degradation initiator may be contained in one or more microparticles or nanoparticles, which may be dispersed in the polymer matrix or contained inside the porogen particle. In some cases, the microparticle or nanoparticle containing the degradation initiator may be a reinforcement microparticle or nanoparticle, as discussed above. In more specific embodiments where the porogen is an alginate, the replaceable metal ion in the hydrogel may be calcium, and the degradation initiator may be a calcium chelating compound, such as a phosphate (e.g., sodium phosphate), a citrate (e.g., sodium citrate) or a lactate (e.g., sodium lactate).

In addition to their porogenic role, the porogen particles of the present invention may also serve as a delivery vehicle for delivering one or more active agents, such as an imaging agent and/or a therapeutic agent (as discussed above). In such a case, one or more active agents may be contained inside the porogen particle. In some embodiments, active agents may be contained in particles within porogen particles.

Non-limiting examples of active agents which may be contained inside the porogen particle may include antibiotics, proteins (e.g., growth factors), platelet rich plasma, cells (e.g., stem cells), degradation inducers of porogen particles (e.g., lactic acid), anti-inflammatory agents, and nucleic acids (e.g., DNA and/or siRNA). In further embodiments, the porogen particle associated with the active agent is a biodegradable porous particle. In more specific embodiments, the porogen particles comprise alginate, and the active agent is a degradation inducer that comprises sodium citrate. In more specific embodiments, the alginate-based particle containing sodium citrate is within another porogen particle.

In further embodiments, the porogen particles may contain one or more growth factors, such as PDGF$\alpha\beta$, PDGF$\alpha\alpha$, PDGF$\beta\beta$, TGF1, TGF2, vascular endothelial growth factor (VEGF) and epithelial growth factor (EGF). In some embodiments, the porogen particle may contain one or more proteins, such as fibrin, fibronectin and vitronectin. Such proteins may act as cell adhesion molecules for osteoconduction and as matrix for bone, connective tissue and/or epithelial growth.

In some embodiments, the porogen particles may contain platelet-rich plasma (PRP), which may be released from the porogen matrix. PRP may contain PDGF$\alpha\beta$, PDGF$\alpha\alpha$, PDGF$\beta\beta$, TGF1, TGF2, VEGF, EGF, fibrin, fibronectin and/or vitronectin.

In some embodiments, the porogen particles may contain smaller size microparticles or nanoparticles, which may also contain one or more active agents, such as those mentioned above. Such microparticles or nanoparticles may be porous or mesoporous microparticles or nanoparticles. Such porous or mesoporous particles may be silicon or silica porous particles such as those disclosed in one of the following documents: (1) PCT publication no. WO 2007/120248 (published on Oct. 25, 2007); (2) PCT publication no. WO 2008/041970 (published on Apr. 10, 2008); (3) PCT publication no. WO 2008/021908 (published on Feb. 21, 2008); (4) U.S. Patent Application Publication No. 2008/0102030 (published on May 1, 2008); (5) U.S. Patent Application Publication No. 2003/0114366 (published on Jun. 19, 2003); (6) U.S. Patent Application Publication no. 2008/0206344 (published on Aug. 28, 2008); (7) U.S. Patent Application Publication no. 2008/0280140 (published on Nov. 13, 2008); (8) PCT Patent Application PCT/US2008/014001, filed on Dec. 23, 2008; (9) U.S. Pat. No. 6,107,102 (issued on Aug. 22, 2000); (10) U.S. Patent Application Publication No. 2008/0311182 (published on Dec. 18, 2008); (11) PCT Patent Application No. PCT/US2009/000239 (filed on Jan. 15, 2009); (12) PCT Patent Application No. PCT/US11/27746 (filed on Mar. 9, 2011); (13) U.S. Patent Application Publication No. 2010/0029785 (published on Feb. 4, 2010); (14) Tasciotti E. et al, 2008 Nature Nanotechnology 3, 151-157; (15) PCT Application No. PCT/US11/28861 (filed on Mar. 17, 2011); (16) PCT Application No. PCT/US11/28890 (filed on Mar. 17, 2010); (17) U.S. Provisional Patent Application No. 61/282,798 (filed on Apr. 1, 2010); and (18) U.S. Provisional Patent Application No. 61/322,766 (filed on Apr. 9, 2010). Each of the above documents are incorporated herein by reference in their entirety.

In some embodiments, the above-described microparticles or nanoparticles within the porogen particles may allow for a release of one or more active agents within the particles in a controlled and sustained fashion. In various embodiments, such controlled and sustained release may allow for optimizing a healing or regeneration process. For instance in a case of treating a bone defect (such as a bone fracture) the controlled and sustained release of active agents from the microparticles or nanoparticles may allow for optimizing the bone healing and/or regeneration process.

The active agents which may be contained inside the microparticles or nanoparticles of the above-described porogen particles may include antibiotics, anti-inflammatory agents, proteins (such as growth factor), and nucleic acids (such as DNA and siRNA). In some embodiments, the growth factors may include one or more of PDGFαβ, PDGFαα, PDGFββ, TGF1, TGF2, vascular endothelial growth factor (VEGF) and/or epithelial growth factor (EGF). In some embodiments, the microparticles or nanoparticles may contain one or more proteins, such as fibrin, fibronectin and vitronectin. In some embodiments, the micro or nanoparticle may contain platelet-rich plasma (PRP). PRP may contain PDGFαβ, PDGFαα, PDGFββ, TGF1, TGF2, VEGF, EGF, fibrin, fibronectin and/or vitronectin.

The above-described microparticles or nanoparticles within the porogen particles may also have a variety of shapes and sizes. In some embodiments, the maximum characteristic size of the particles may be less than about 100 microns, less than about 50 microns, less than about 20 microns, less than about 10 microns, less than about 5 microns, less than about 4 microns, less than about 3 microns, less than about 2 microns, or less than about 1 micron. Yet, in some embodiments, the maximum characteristic size of the particles may be from 100 nm to 3 microns, from 200 nm to 3 microns, from 500 nm to 3 microns, or from 700 nm to 2 microns.

Yet, in some embodiments, the maximum characteristic size of the particle may be greater than about 2 microns, greater than about 5 microns, or greater than about 10 microns.

A person of ordinary skill in the art will also recognize that the shape of the microparticles or nanoparticles within the porogen particles is not particularly limited. In some embodiments, the microparticles or nanoparticles may be a spherical particle. Yet, in some embodiments, the particles may be a non-spherical particle. In some embodiments, the microparticles or nanoparticle can have a symmetrical shape. Yet, in some embodiments, the microparticles or nanoparticle may have an asymmetrical shape.

In some embodiments, the microparticles or nanoparticles may have a selected non-spherical shape, such as an oblate spheroid, a disc or a cylinder. In some embodiments, the porous particle may be a truncated oblate spheroidal particle.

The microparticles or nanoparticles within the porogen particles of the present invention may also comprise a porous oxide material or a porous etched material. Examples of porous oxide materials include, but are not limited to, porous silicon oxide, porous aluminum oxide, porous titanium oxide and porous iron oxide. The term "porous etched materials" refers to a material, in which pores are introduced via a wet etching technique, such as electrochemical etching or electroless etching. Examples of porous etched materials include porous semiconductors materials, such as porous silicon, porous germanium, porous GaAs, porous InP, porous SiC, porous $Si_xGe_{1-x}$, porous GaP and porous GaN. Methods of making porous etched particles are disclosed, for example, US Patent Application Publication no. 2008/0280140.

In some embodiments, the porogen particles of the present invention may be a nanoporous particle. In some embodiments, an average pore size of the nanoporous particle may be from about 1 nm to about 1 micron, from about 1 nm to about 800 nm, from about 1 nm to about 500 nm, from about 1 nm to about 300 nm, from about 1 nm to about 200 nm, or from about 2 nm to about 100 nm. In some embodiments, the average pore size of the nanoporous particle can be no more than 1 micron, no more than 800 nm, no more than 500 nm, no more than 300 nm, no more than 200 nm, no more than 100 nm, no more than 80 nm, or no more than 50 nm.

In some embodiments, the average pore size of the nanoporous particle can be from about 5 nm to about 100 nm, from about 10 nm to about 60 nm, from about 20 nm to about 40 nm, or from about 30 nm to about 30 nm. In some embodiments, the average pore size of the porous particle can be from about 1 nm to about 10 nm, from about 3 nm to about 10 nm, or from about 3 nm to about 7 nm.

In general, pores sizes may be determined using a number of techniques, including $N_2$ adsorption/desorption and microscopy, such as scanning electron microscopy. In some embodiments, pores of the nanoporous particle may be linear pores. Yet, in some embodiments, pores of the nanoporous particle may be sponge like pores.

A person of ordinary skill in the art can also envision that various methods may be used to load active agents into the porous particles. Methods of loading active agents into porous particles are disclosed, for example, in U.S. Pat. No. 6,107,102 and US Patent Application Publication No. 2008/0311182.

In some embodiments, the porous particles within the porogen particles of the present invention are porous silicon particles. In general, porous silicon may be bioinert, bioactive or biodegradable, depending on its porosity and pore size. Also, a rate or speed of biodegradation of porous silicon may depend on its porosity and pore size. See e.g, Canham, Biomedical Applications of Silicon, in Canham L T, editor. Properties of porous silicon. EMIS datareview series No. 18. London: INSPEC. p. 371-376. The biodegradation rate of porous silicon particles may also depend on surface modification. Porous silicon particles and methods of their fabrication are disclosed, for example, in Cohen M. H. et al Biomedical Microdevices 5:3, 253-259, 2003; US Patent Application Publication No. 2003/0114366; U.S. Pat. Nos. 6,107,102 and 6,355,270; US Patent Application Publication No. 2008/0280140; PCT Publication No. WO 2008/021908; Foraker, A. B. et al. *Pharma. Res.* 20 (1), 110-116 (2003); and Salonen, J. et al. *Jour. Contr. Rel.* 108, 362-374 (2005). Porous silicon oxide particles and methods of their fabrication are disclosed, for example, in Paik J. A. et al. J. Mater. Res., Vol 17, August 2002, p. 2121.

In some embodiments, the porous particle may be a particle produced utilizing a top-down microfabrication or nanofabrication technique, such as photolithography, electron beam lithography, X-ray lithography, deep UV lithography, nanoimprint lithography or dip pen nanolithography. Such fabrication methods may allow for a scaled up production of particles that are uniform or substantially identical in dimensions.

Active Agents

As set forth above, the individual components of the compositions of the present invention may be associated with one or more active agents. In various embodiments, the active agent may be associated with the biodegradable polymer matrix, the biodegradable reinforcing particle, and/or the porogen particle.

In some embodiments, the active agent comprises antibiotics, proteins, platelet rich plasma, cells (e.g., stem cells), degradation inducers of porogen particles (e.g., lactic acid and/or sodium citrate), anti-inflammatory agents, cell viability enhancing agents (e.g., glucose), and/or imaging agents (e.g., barium sulfate,). More specific examples of active agents were described above. Additional active agents that may be suitable for use with the compositions of the present invention are disclosed in PCT Application Nos. PCT/US11/28861 and PCT/US11/28890, both filed on Mar. 17, 2010.

Use of Biodegradable Compositions as Scaffolds

In various embodiments, the compositions of the present invention may be utilized as scaffolds. In a specific example, the scaffolds of the present invention may be used for treating bone defects, such as bone fractures, maxillofacial defects, and craniofacial defects. Scaffolds of the present invention may also be utilized for tissue engineering, tissue regeneration, and wound healing. In additional embodiments, the scaffolds and compositions of the present invention may be used for treating or preventing a microbial infection, such as a bacterial infection at a site of a bone defect.

In more specific embodiments, the scaffolds of the present invention may be used in treating soft tissue injuries and facilitating ligament/tendon repair. Likewise, the scaffolds of the present invention may find various applications in tooth regeneration, neural repair (e.g., facilitation of spinal cord regeneration), and intervertebral disc replacement. The scaffolds of the present invention may also be used to treat cartilage defects. Likewise, the scaffolds of the present invention may be utilized as vascular grafts. The scaffolds of the present invention may also be used to make or engineer artificial tissues or organs, such as an engineered pancreas for type I diabetic patients. Additional applications for the scaffolds of the present invention can also be envisioned by persons of ordinary skill in the art.

Application of Scaffolds for Treatment of Bone Defects

As set forth previously, a specific embodiment of the present invention pertains to methods of treating a bone defect in a subject by applying to an area of the bone defect in the subject a scaffold of the present invention. For instance, in some embodiments, the bone defect treatment methods of the present invention include: (1) applying to an area of the bone defect in the subject a scaffold that comprises: (a) a biodegradable polymer matrix, and (b) at least one biodegradable reinforcing particle dispersed in the matrix, as previously described. In further embodiments, the applying step comprises injecting the subject with a composition of the present invention. In additional embodiments, the scaffold is formed from the composition in the body of the subject after the injecting. In further embodiments, the scaffold that is applied also comprises at least one porogen particle, as described above. In further embodiments, the applied scaffold also comprises one or more active agents, as also described.

Bone defects that can be treated with the scaffolds of the present invention include, without limitation, bone fractures, maxillofacial defects, craniofacial defects, spine defects (e.g., defects and/or injuries in intervertebral bodies), long bone defects (e.g., weight bearing and non-weight bearing defects), and combinations thereof. In various embodiments, the aforementioned defects to be treated may be critical size defects and/or non-critical size defects.

Methods of Making Biodegradable Compositions

Additional aspects of the present invention pertain to methods of making the above-mentioned biodegradable compositions. Such methods generally comprise dispersing in a biodegradable polymer matrix at least one biodegradable reinforcing particle, as previously described. Such methods may also involve the dispersion of porogen particles and/or active agents into the biodegradable polymer matrix. Additional details about such methods are described in the Examples below.

Advantages and Applications

The methods and compositions of the present invention provide numerous advantages. One of the advantages of the compositions of the present invention may lie in the compositions' mulitifunctionality, as the composition may have one or more of the following properties: optimal mechanical characteristic; injectability for irregular defects; and multiple (i.e. two or more) stages of bioactive release to enhance the bone healing process. The scaffold and compositions of the present invention may also be capable of providing one or more of the following advantages: i) cross-linking in situ, ii) conforming to a bone geometry, iii) providing immediate mechanical stability, iv) providing a continuous delivery of one or more active agents, which may be, for example, antibiotics and growth factors; v) promoting accelerated tissue regeneration and vi) degrading into benign by-products that may be resorbed and excreted by the body.

An additional advantage of the compositions of the present invention may be the ability to vary biodegradation and/or release rates of various components. For instance, the present compositions may allow for the biodegradation and/or release process to be adjusted to match the kinetics of the bone regeneration process and thus, progressively transfer the loads from the scaffold to the new tissue. The development of bone architecture may be naturally driven by the mechanical forces applied. As a result, osteoclasts may begin resorbing bone that is not subjected to the appropriate load and only remodel the newly formed bone in areas of high stress.

The tunability of both the release of active agents, such as therapeutic agents and/or imaging agents, and degradation rates of each individual component in the scaffold may also provide the ability to mimic and accelerate one or more natural regeneration processes. For instance, the scaffolds and compositions of the present invention may be designed to provide immediate stability to a minor or substantial bone defect. The present compositions and scaffolds of the present invention may also simultaneously initiate and/or accelerate the natural healing cascade.

Additional aspects of the present invention will now be described with reference to specific and non-limiting Examples.

EXAMPLES

Example 1. Scaffold Components

FIGS. 1A-1F shows alginate hydrogel microspheres encapsulating cells and bioactive molecules. Inside of the above porogen (~200-500 microns) is PRP as well as mesenchymal stem cells (FIG. 1A-1B optical image, FIG. 1C confocal image green-cells, FIG. 1D-1F SEM image). Also within the porogen may be microparticles or nanoparticles, which may be coated with a polymer, such as agarose or PLGA, that may also contain one or more active agents loaded within the nanopores (FIG. 2).

Figure 4:
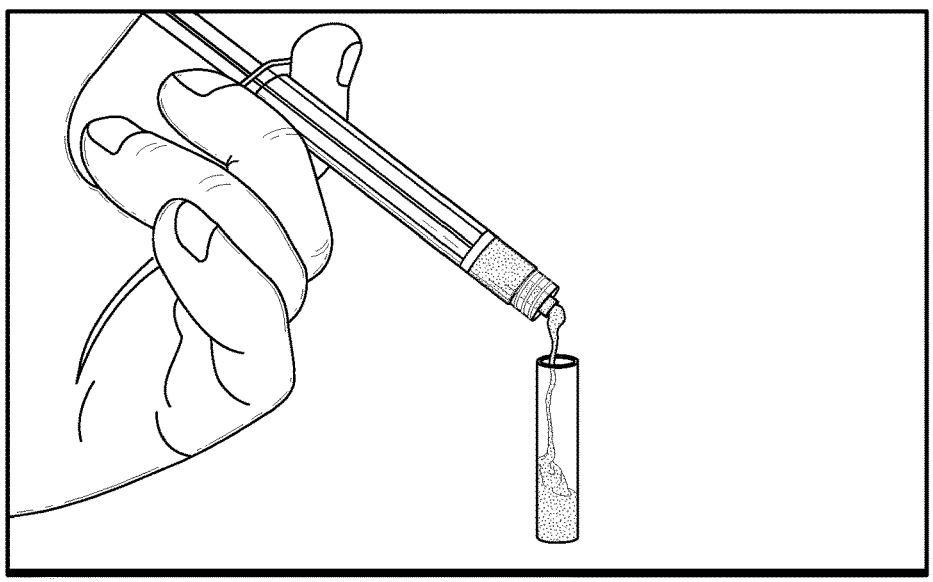
FIG. 4 illustrates the injectability of poly(propylene fumarate) (PPF).
Figure 5:
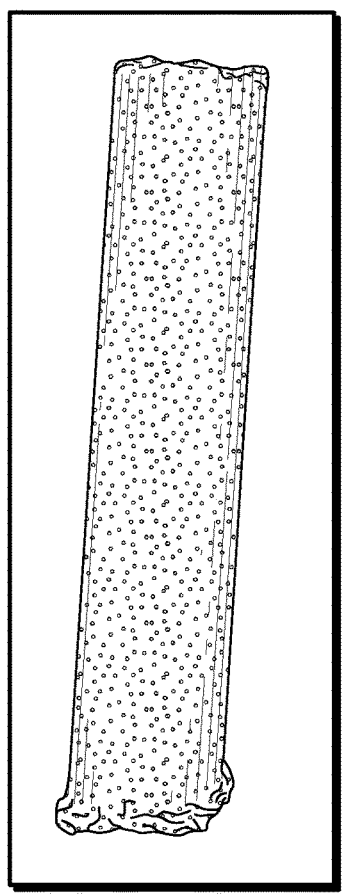
FIG. 5 is a photograph of an alginate/PPF composite scaffold fabricated using a cylindrical Teflon mold.
Figure 6A:
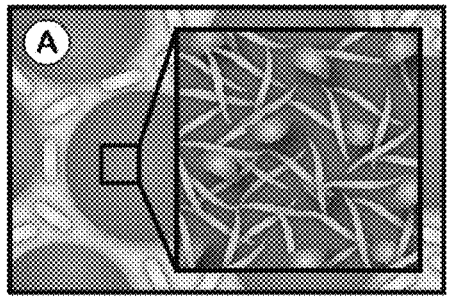
FIGS. 6A-6F illustrate the operation of a biodegradable scaffold to treat a bone defect.
Figure 6B:
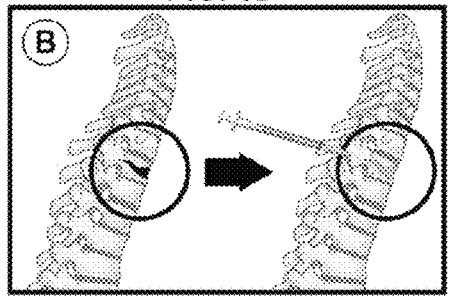
Figure 6C:
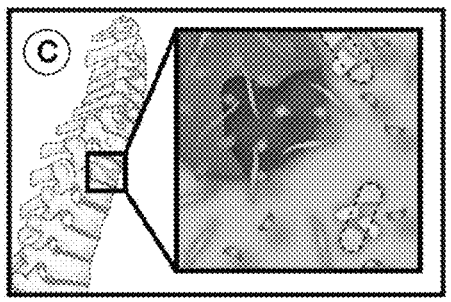
Figure 6D:
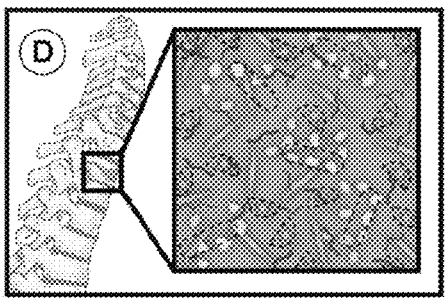
Figure 6E:
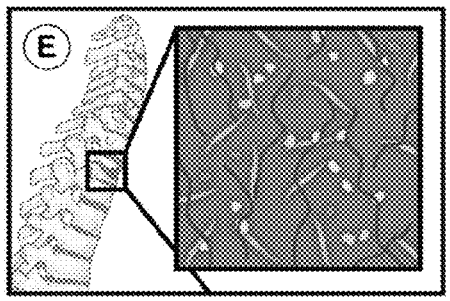
Figure 6F:
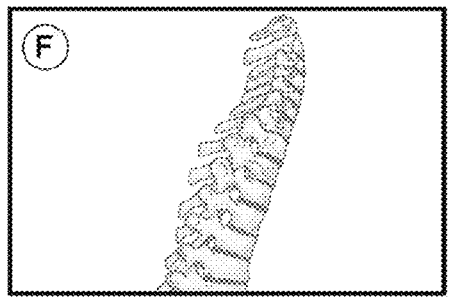

The porogen may be dispersed within a viscous polymer matrix, such as a PPF matrix, that may contain silica nanorods as mechanical reinforcement (FIGS. 3A-3D). In some embodiments, the composition with some or all mentioned components may be loaded into a syringe and injected into the bone defect where it may crosslink in the shape of the bone defect geometry (FIG. 4). Yet, in some embodiments, the composition may be used for forming a scaffold ex situ. After cross-linking, the scaffold composite may conform to the defect geometry as seen below in FIG. 5 using a cylindrical mold.

Example 2. Release of Active Agents from Scaffolds for Treatment

The multifaceted nature of the injectable matrix may provide ideal means of staggering the delivery of the above-mentioned active agents that may enhance stem cell activity at rates contingent upon the corresponding stage of fracture healing. For example, PRP may provide a cocktail of all necessary growth factors with the additional advantage of presenting them in optimal ratios for cell growth. PRP may therefore be a supplier of bioactive molecules throughout the entire scaffold and may be contained in one or more components of the composition and a scaffold formed therefrom, such as the porogen particles, the reinforcing microparticles or nanoparticles, the microparticles or nanoparticles with the porogen particles and the polymer matrix. In some embodiments, PRP may be contained in more than one of the above mentioned components of the composition or the scaffold. In some embodiments, PRP may be contained in each of the above mentioned components of the composition or the scaffold.

In some embodiments, one or more antibiotics may be incorporated into one or more components of the composition and a scaffold formed therefrom, such as the porogen particles, the reinforcing microparticles or nanoparticles, the microparticles or nanoparticles with the porogen particles and the polymer matrix. In some embodiments, one or more antibiotics may be contained in more than one the above mentioned components of the composition or the scaffold. In some embodiments, one or more antibiotics may be contained in each of the above mentioned components of the composition or the scaffold. Overall, the present system may provide antibiotics during the entirety of the healing process of a bone defect, such as bone fracture.

The operation of the scaffold in some embodiments may be illustrated as follows: The immediate delivery of growth factors may be supplied through the PRP dispersed within the porogen particles. Upon degradation of the porogen particles, the PRP may be released into the defect site. A faster degradation (and a faster release) may be achieved by using as porogen particles alginate capsules with a thin layer of alginate surrounding the encapsulated content. On the contrary, solid alginate beads may degrade in a longer time and may therefore provide a sustained release over 1 week or 2 weeks or 3 weeks or 4 weeks. To induce degradation of alginate porogen particles, the reinforcing microparticles or nanoparticles may be loaded with the calcium chelation agent, sodium citrate, and encapsulated within the alginate porogen itself. As the sodium citrate is slowly released from the reinforcing microparticles or nanoparticles, the calcium ions that gel the alginate may be replaced with citrate ions causing the gel to disassemble and "dissolve." The rate at which this degradation may occur may be controlled.

Secondly, upon the porogen particle degradation, the microparticles or nanoparticles that were contained inside the porogen particles may be released with the PRP in stage one. In case, when these micro or nanoparticles are mesoporous silicon microparticles or nanoparticles, they may be coated with a bulk degrading polymer, such as PLGA or agarose, which may provide a further extended sustained release.

In some embodiments, the mesoporous silicon microparticles or nanoparticles may be biodegradable porous silicon with well controlled shapes, sizes and pores. The size of the pores may confine the space for the entrapment of an active agent of choice while the porous silicon surface chemistry may affect the stability and duration of its interaction with the active agent.

The ability to load active agents within the porous matrix of the particle at room temperature may enable the use as the active agent sensitive compounds susceptible to temperature dependent degradation or inactivation. Polymer coating of the mesoporous micro or nanoparticles, such as mesoporous silicon micro or nanoparticles, may allow avoiding the burst release of the active agent, such as an antibiotic from the pores and to achieve its sustained release over the course of a week. Pore size and coating strategy may be used in parallel to provide sustainable release of active agents to enhance process of healing cascade and to prevent the establishment of possible infections in a bone defect site, such as fracture site.

Thirdly, for the final and longest delay of release, the reinforcing particles embedded within the polymer matrix may release PRP as the surrounding polymer matrix degrades exposing the pores of the reinforcing particles to the defect site. Due to the various rates of degradation of each above mentioned components, the needs of each phase of the healing cascade may be met.

The composition may be a composite material having the texture of a paste enabling it to conform to different shapes according to the specific application and including the reconnection of separated bones and the replacement of missing bone. In some embodiments, the composition may be used for treating bone defects, such as fracture or an injury for a bone in a body of an animal, which can be a warm bloodied animal, such a mammal, which may be a human. For example, the composition may be used for treating a bone fracture or an injury in a human body bone, such as a spine, a skull or a facial bone.

FIG. 6A-6F schematically depicts the use of the composition for vertebral body compression fractures. PPF refers to the polymer matrix, which may be poly(propylene fumarate); MSN refers to reinforcing micro or nanoparticles, which may mesoporous silica nanorods; SE refers to micro or nanoparticles inside the porogen beads, such micro or nanoparticles may be mesoporous silicon micro or nanoparticles.

Example 3. Synthesis, Characterization and Use of Alginate Porogens

The following example provides steps for incorporation of cells and platelet-rich plasma (PRP) and bioactive molecules into an alginate microsphere matrix during a fabrication process.

Protocol for Synthesis of Alginate Porogen Microparticles with the Incorporation of Cells and Platelet-Rich Plasma As depicted in FIG. 7C-7E, Calcium alginate beads were synthesized by emulsion in mineral oil with low surfactant conditions and acetic acid as a catalyst. In order to optimize the process and accomplish beads with sizes ranging from 300-500 µm, the concentration ratio of sodium alginate and platelet-rich plasma, the amount and type of surfactant, the stir rate and size of beaker and stir bar used for creating an optimal volume were all varied within the same protocol. Select runs of this process are provided in Table 1 below.

TABLE 1

Runs 1-6: Variables manipulated, values employed, bead size range obtained.

| Run | Percent Alginate Solution | Starting pH of Alginate Solution | Surfactant Concentration (Span80) | Stir Speed | Bead Size Range (average) | Notes |
|---|---|---|---|---|---|---|
| 1 | 2 | 7.55 | 2% | 2 on VWR | 80-100 µm | Did not sonicate CaCO3 prior to addition to alginate. Added CaCl2 to alginate mineral oil mixture |
| 2 | 2 | 7.55 | 4% | 2 on VWR | 80-200 µm | Added Alginate-mineral oil mixture to CaCl2 |
| 3 | 5 | 7.65 | 4% | 5-6 on Cimarec | 80-250 µm | |
| 4 | 5 | 7.61 | 4% | 4 on Cimarec | 80-300 µm | Larger beads but increased clumping (as seen in 4b) |
| 5 | 5 | 7.58 | 3% | 5-6 on Cimarec | Poor shape., difficult to characterize | |
| 6 | 4 | 7.56 | 3% | 4 on Cimarec | 80-300 µm | Some clumping, a few beads in 300 µm range |

The addition of PRP into the alginate matrix was found to be essential to create a desired viscosity for bead creation within the aimed 200-500 microns. The difference in size is illustrated in FIGS. 7A-7B and 7F.

The protocol for the incorporation of live cells into the microparticles is as follows: 5 grams of sodium alginate was slowly dissolved in 75 mM NaCl/12.5 mM HEPES in PRP:DI water (1:1) (5% w/v). The pH of the solution was adjusted to a value of ~7.5. Sonicated aqueous CaCO3 mixture with 500 mM Ca2+ equivalent was then added to the alginate solution. Mesenchymal stem cells were then added to the alginate solution suspended in PRP. The alginate-cell-CaCO3 mixture was then added to a solution of mineral oil with 2 Span80 by volume and stirred with a magnetic stir bar for 15 minutes. With continued stirring, a mixture of mineral oil and glacial acetic acid was slowly added and allowed to mix for 10 additional minutes to initiate the release of calcium from the carbonate and the subsequent gelation of the calcium alginate beads. Beads were then separated from the oil dispersion by partitioning the mixture above into an aqueous $CaCl_2$ solution. The beads were then collected by pipette and washed on a vacuum filter with 1% Tween 80 to remove residual oil. Due to the size distribution, a method of sieving out unwanted sizes was developed. Briefly, a 500 micron ASTM sieve was used to remove all beads larger than 500 microns, and a 212 micron sieve was used to remove all beads smaller than 212 microns.

Characterization of Alginate Porogens

Figure 1A:
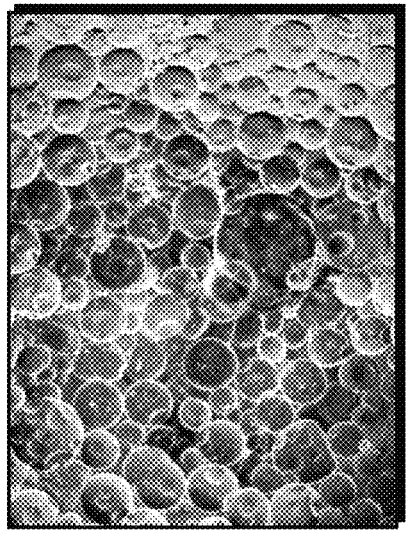
FIGS. 1A-1F present images of alginate hydrogel microspheres/beads (~200-500 microns). Inside the beads is platelet-rich plasma (PRP) as well as mesenchymal stem cells (FIGS. 1A-1B: optical image.
Figure 1B:
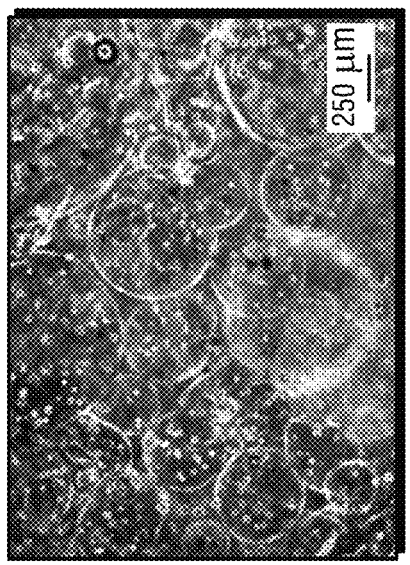
Figure 1C:
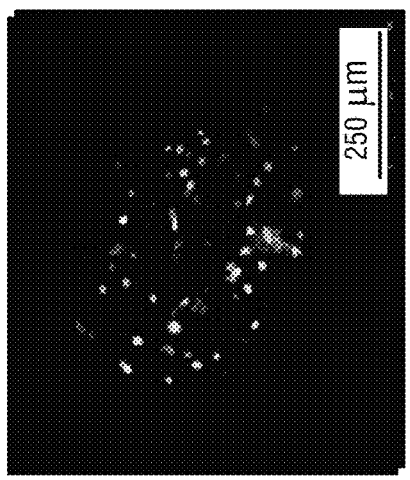

FIG. 1A provides optical images of alginate porogens with PRP (top left), and alginate porogens with mesenchymal stem cells (FIG. 1B, top center). FIG. 1C also shows confocal microscopy images of alginate porogens with mesenchymal stem cells labeled with green fluorescence (CSFB) (top right). In addition, FIGS. 1D-1F shows SEM images of alginate porogens (bottom).

Figure 1D:
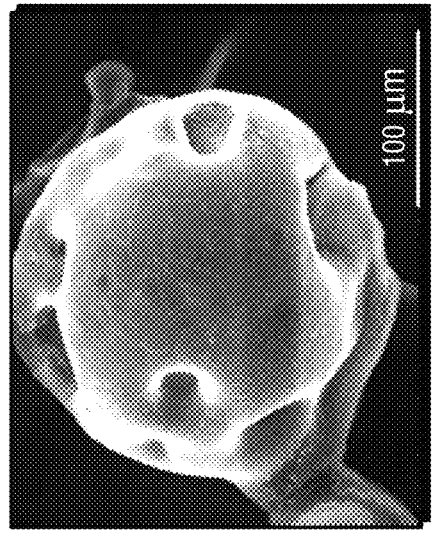
Figure 1E:
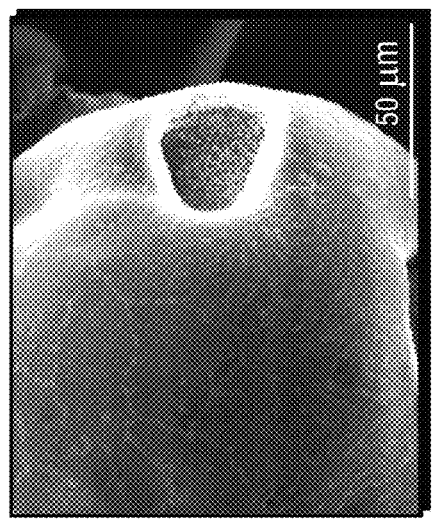
Figure 1F:
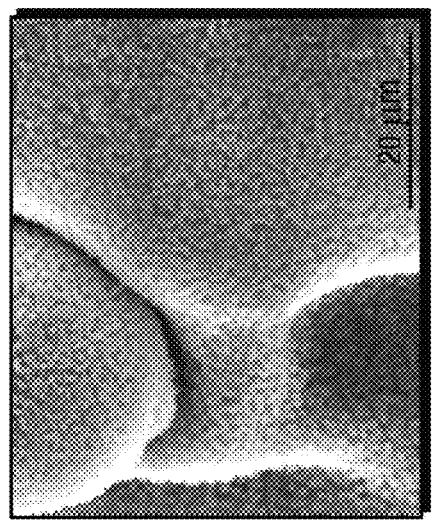
Figure 2:
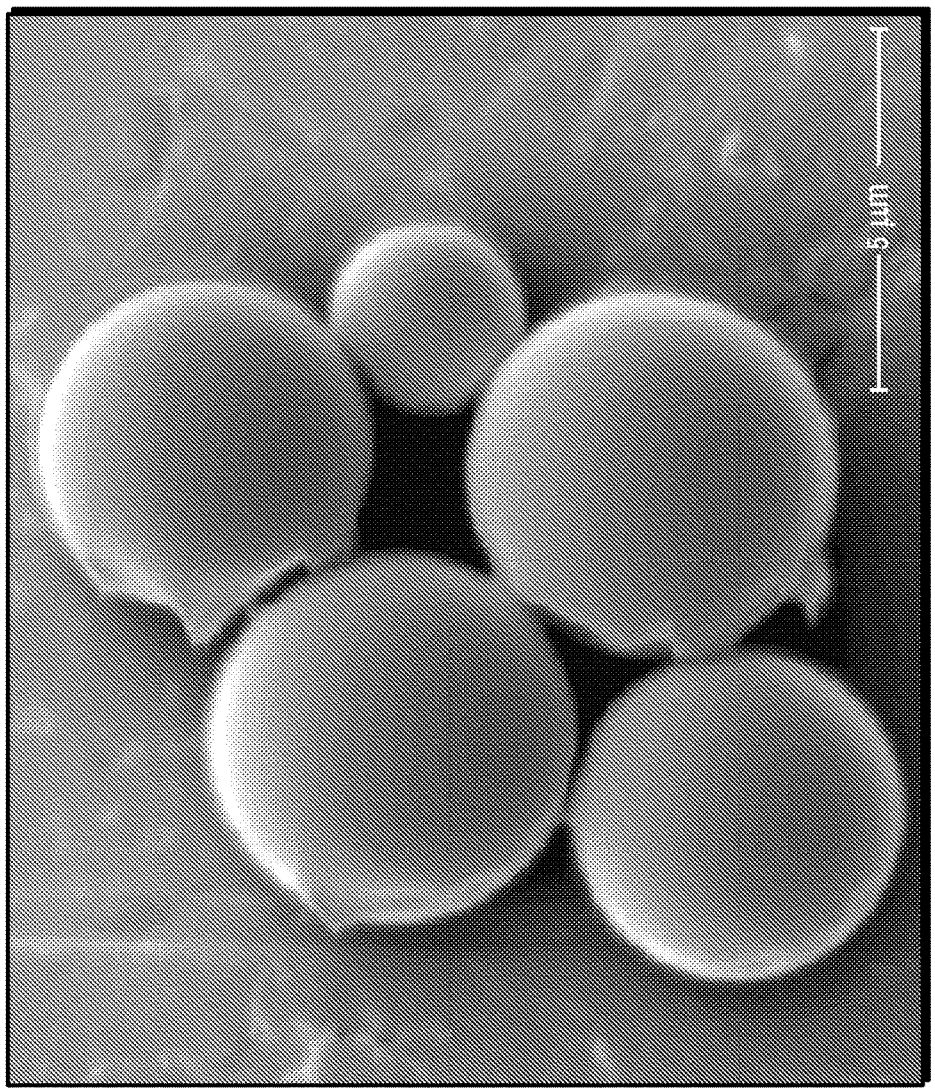
FIG. 2 shows poly(lactic-co-glycolic acid) (PLGA) coated mesoporous silicon.
Figure 3B:
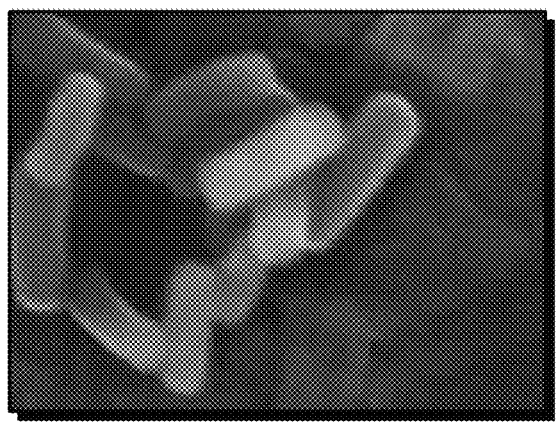
FIGS. 3A-3D show images of surface-modified and co-condensated silica nanorods SEM (FIGS. 3A-3B) at two different magnifications and transmission electron microscope (TEM) (FIG. 3C-3D) at two different magnifications.
Figure 3D:
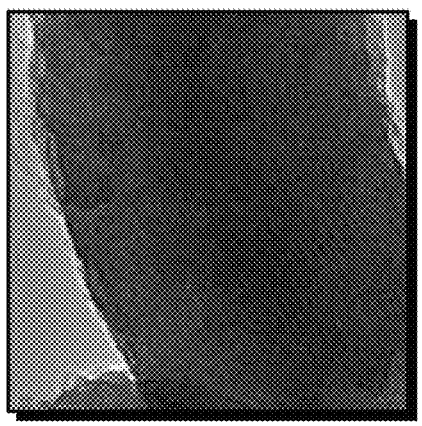
Figure 3A:
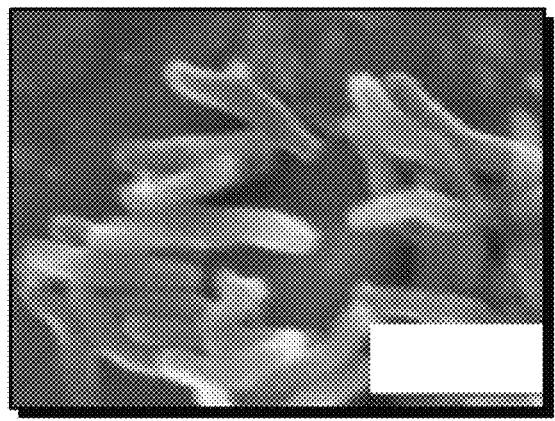
Figure 3C:
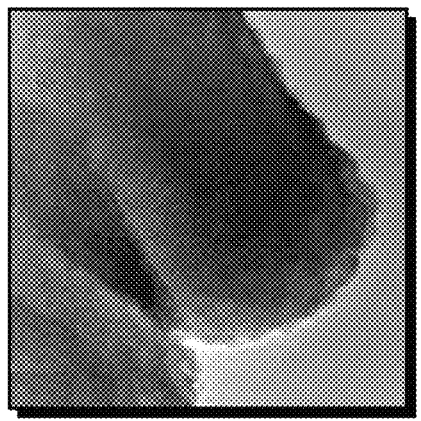

Alginate porogens were fabricated using the above-mentioned protocol and were characterized by optical microscopy (FIG. 1A-1B) (Nikon Eclipse TS 100), confocal microscopy (FIG. 1C) (Leica MD 6000), and scanning electron microscopy (SEM) (FEI Quanta 400 ESEM FEG) (FIGS. 1D-1F). The samples were sputtered with 20 nm gold by a Plasma Sciences CrC-150 Sputtering System (Torr International, Inc) prior to SEM analysis.

FIGS. 1B-1C (top center and top right) also includes images of mesenchymal stem cells stained with a fluorescent dye. Calcium alginate beads were synthesized by the emulsion process described above with the incorporation of cells into the aqueous alginate phase. The stem cells were stained with the green fluorescence dye Carboxyfluorescein diacetate, succinimidyl ester (CSFE) using a 25 µm staining solution. After 12 hours of incubation post-staining, the cells were trypsinized and re-suspended in the 5% alginate/PRP solution at $2 \times 10^6$ cells per ml. The emulsion was then performed as described above, thereby creating alginate and PRP beads encapsulating live cells. Beads with cells were then incubated in DMEM complete media (10% FBS, 1% antibiotic) at 37 degrees Celsius prior to imaging.

Enhancing the Mechanical Properties of a Porous Polymer Matrix Through Incorporation of Alginate Porogens PPF and alginate scaffolds were created using Teflon molds with dimensions 6 mm d×12 mm h. Briefly, the PPF monomer was diluted with N-vinyl-2-pyrrolidone (NVP) using a 1:4 ratio prior to dispersion. A mixture of 40% alginate porogens by weight within PPF was mechanical stirred. 20 mg of benzoyl peroxide (BP) was then added to initiate the cross-linking of PPF along with N,N-Dimethyl-p-toluidine (DMT) to accelerate the reaction. The mixture was then poured into the Teflon mold and placed at 60 degrees Celsius overnight to fully cross-link.

The compressive mechanical properties of the alginate-incorporating constructs were measured according to ISO5833 standards. 6 mm×12 mm cylindrical scaffolds (n=5) incorporating 40% alginate microspheres by weight were compressed along their long axis using a mechanical testing machine with a 10 kN load cell (MTS). As a comparison, 80% salt PPF scaffolds of equivalent size were created and the salt leached out to create a porous structure. The 80% salt porous scaffolds were then tested using the same methods described above. The young's modulus and stress at offset yield were recorded and are illustrated in FIGS. 8A-8B, respectively.

Results from MTS Testing Showing Mechanical Reinforcement Due to Presence of Alginate Microparticle Porogens As summarized in FIGS. 8A-8B, the alginate porogens provide an 8-fold increase in mechanical strength compared to pre-fabricated PPF porous scaffolds by temporarily filling the voids until they undergo biodegradation. Furthermore, the elastic modulus of the porogen composite provides a significantly closer match to that of trabecular bone within the vertebral body (165-291 MPa)[1] than the current PMMA standard (48-76 MPa)[2].

The addition of calcium alginate porogens into the (PPF) based matrix renders the temperature increase, from the exothermic cross-linking reaction, virtually undetectable. This may alleviate existing concerns with current injectable polymers of damaging surrounding neural and vascular structures.

FIG. 9 presents temperature profile of PPF cross-linking with varying alginate porogen content. Calcium alginate beads were synthesized by emulsion/internal gelation methods described above without the addition of cells. The change in temperature of the scaffold during cross-linking was measured by recording the temperature of the mixture as a function of time after the addition of the last component. The mixture was packed into a Teflon cylindrical mold (According to ISO5833 for acrylic resin cements) where a temperature probe connected to a multimeter was positioned at the center of the mold to record the temperature of the mixture every 1 second until the temperature began to drop and then stabilize.

Controlled Release of Growth Factors from Platelet Rich Plasma to Induce Cell Migration, Proliferation and Differentiation Alginate beads with platelet-rich plasma were fabricated and separated into three size ranges using various sieves (x<212 µm, 212<x<500 µm, and x>500 µm). 100 mg of swelled alginate beads of each size range were weighted out into eppendorf tubes and 200 ul of DMEM was added to each sample. Samples were then placed horizontally on a rotator at 37 degrees Celsius. At various time point samples were spun down (2500 rpm for 5 min) and 100 µl of supernatant was removed from each sample and stored at −20 C for later ELISA analysis.

Figure 10B:
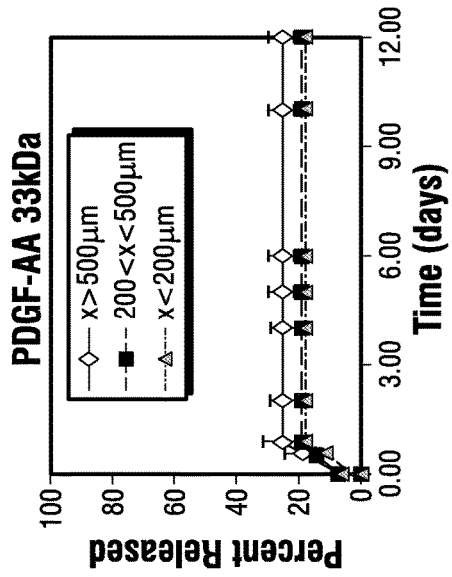
Figure 10A:
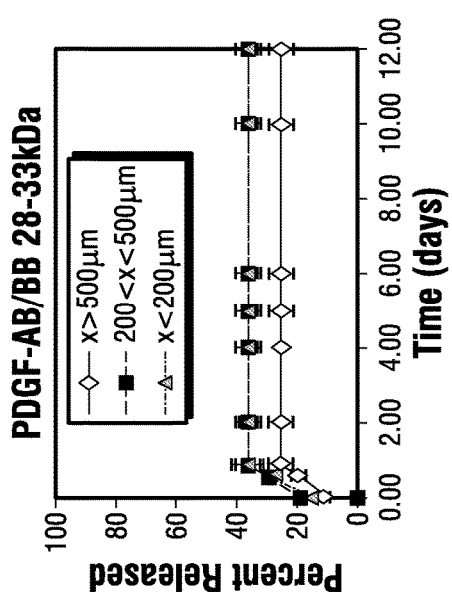
FIGS. 10A-10O show various studies relating to the physiological effects of alginate porogens.
Figure 10D:
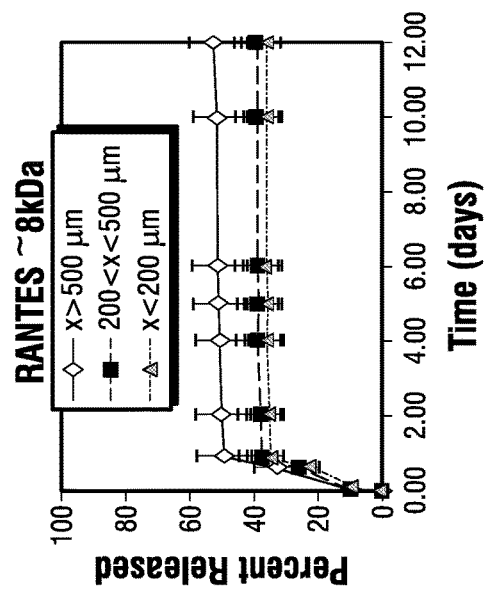
Figure 10C:
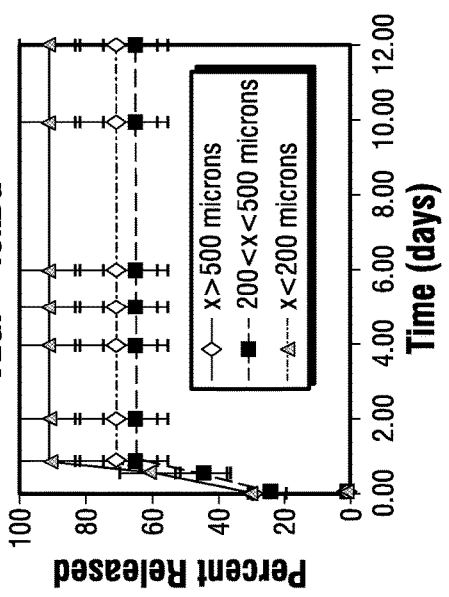
Figure 10N:
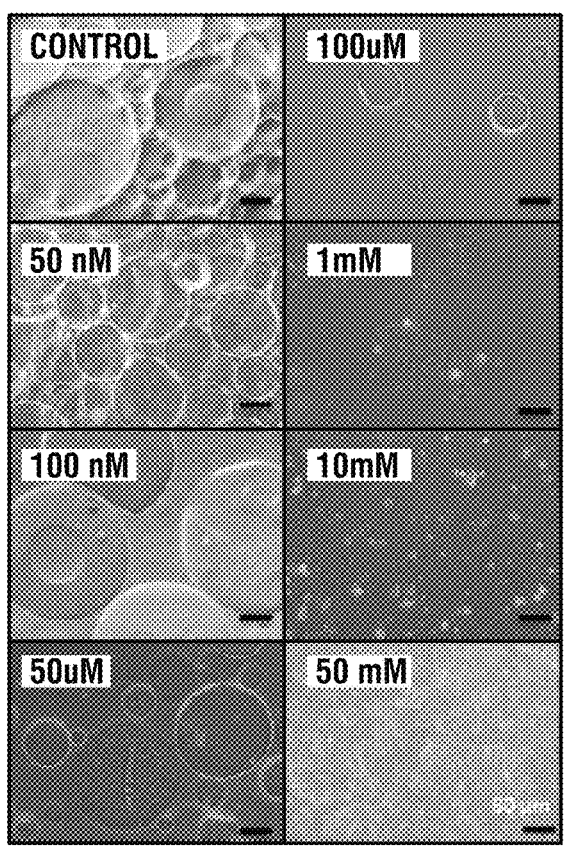
FIG. 10N shows calcium alginate accelerated degradation using sodium citrate as a chelation agent at various concentrations (top panel). Cytotoxicity of Alginate/PRP porogens from the top panel on rat cortical bone mesenchymal cells (MSC) are shown on the bottom panel (FIG. 10O).
Figure 10O:
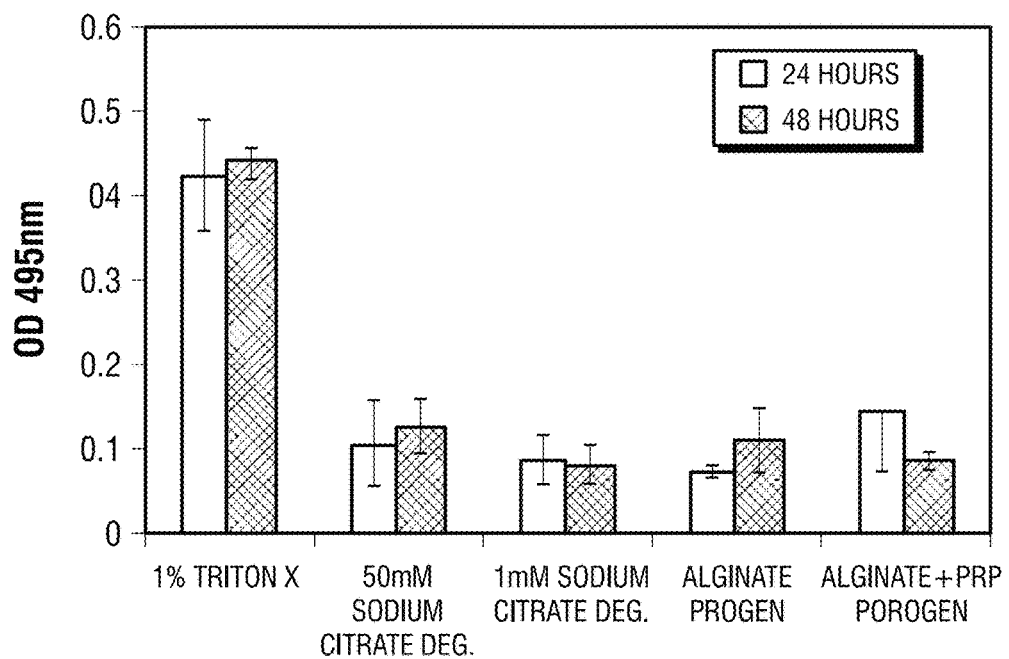
Figure 12:
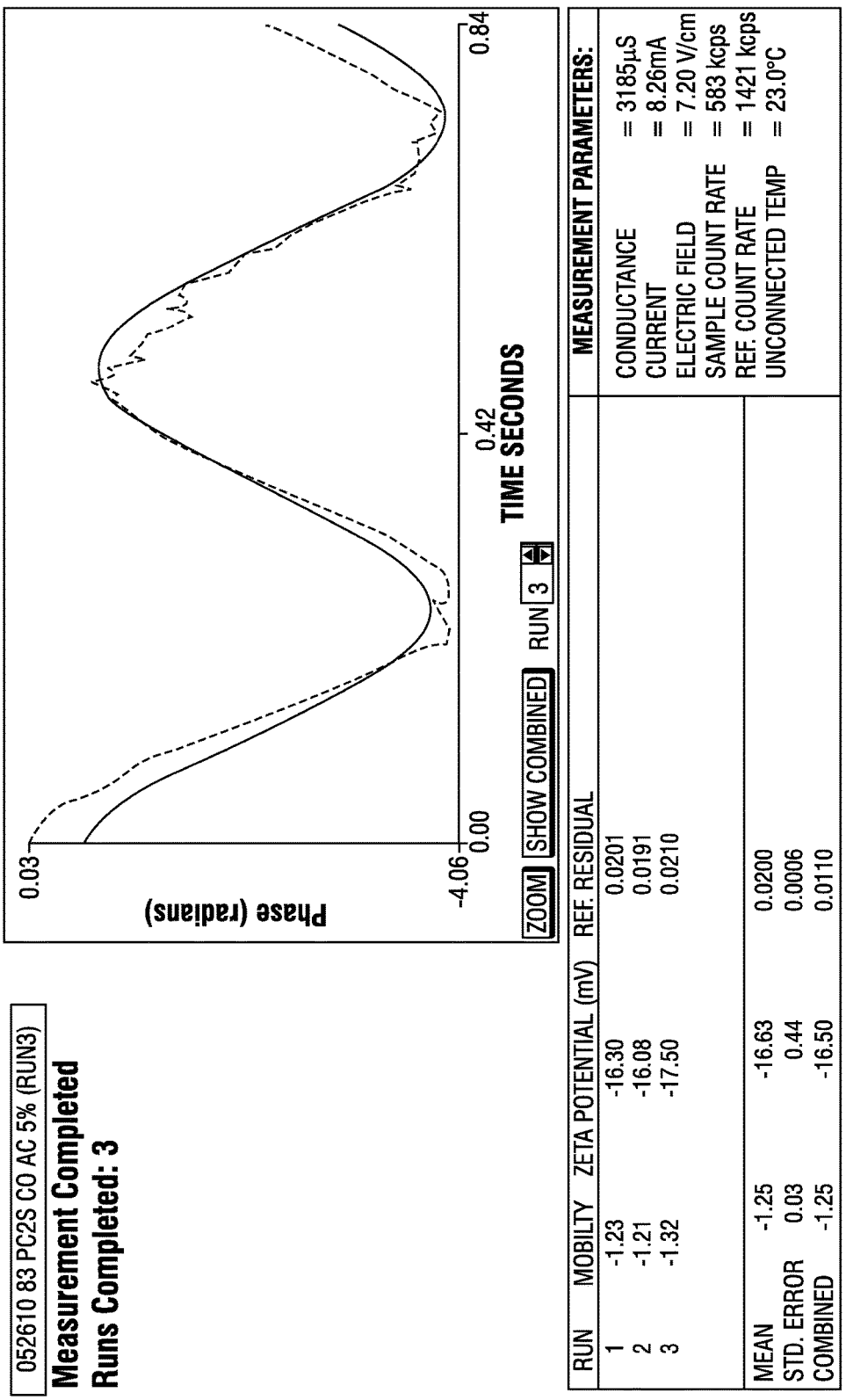
FIG. 12 presents results of measuring zeta potential for co-condensed acrylate nanorods showing a surface charge of around −17 mV. Oxidized silica (unmodified) has a surface charge of around −40 mV.

The release of PDGF, VEGF, and RANTES from PRP with alginate porogens of varying sizes is demonstrated in FIG. 10A. The effect of the mitogenic growth factors, PDGF-AB/BB/AA on cell proliferation is demonstrated in FIG. 10B. Similarly, the stimulatory effect of RANTES release from the complex is illustrated in FIG. 10C. Furthermore, the induction of angiogenesis was been confirmed in a Lewis Rat subcutaneous implantation of the PRP/alginate porogens (FIG. 10D).

Cryopreservation of Biological Components

As shown in the cell viability assays of FIG. 10E, porogen particles also provide cell viability protection during the injecting and cross-linking process of the polymer scaffold. Furthermore, as demonstrated in FIG. 10F, The degradation of the porogen can be artificially controlled through the controlled delivery of calcium chelation agents that cause dissolution of the porogens.

Example 4. Synthesis and Characterization of Silica Nanorods

The following experiments pertained to porous silica nanorod fabrication with desired aspect ratios for mechanical reinforcement. In the adjustments of reagents such as ammonia, CTAB, TEOS and 3-(trimethoxysilyl)propyl methacrylate silane, the aspect ratio of the silica may be increased to the desired size for nano reinforcement. In addition, mesoporous silica nanorods may contain one or more active agents (including but not limited to, contrast agents, metallic ions, fluorescent dyes, and cations), which may be incorporated into porous silica nanorod matrices during the fabrication process. The following protocols also describe surface modification methods to covalently bond the porous silica nanorod to the backbone (or side chains) of polymer matrices to be reinforced.

Protocol for Synthesis of Silica Nanoparticles with Incorporated Barium Sulfate

CTAB was dissolved in 70 ml $H_2O$ for 30 minutes. Ammonium hydroxide was added and the mixture was stirred vigorously for 1 hr. TEOS and Barium Sulfate (70 mol % TEOS) (optional) was added and stirred for 4 hr. The solution was centrifuged at 13,000 rpm for 10 min and washed in a mixture of ethanol and water several times. The particles were dried under vacuum overnight at room temperature. The surfactant was removed by placing the dried particles in 100 ml ethanol and 1 ml concentrated HCl for 6 hours. The solution was centrifuged at 13,000 rpm for 10 min and washed in a mixture of ethanol and water several times. This washing process allows for removal of surfactant and the survival of the oxidized, active surface. The molar ratio of the reaction was 100 TEOS: 29 CTAB: 35,700 $H_2O$: 714 $NH_3$—$H_2O$ (varies with desired size/aspect ratio). Size and morphology were characterized by dynamic light scattering (DLS) transmission electron microscope (TEM), and scanning electron microscope (SEM). Surfactant removal was characterized through zeta potential and FTIR. Pore size and volume were observed through BET. The results are summarized in Table 2 below and depicted in FIGS. 11A-11C and FIGS. 14-16.

TABLE 2

Increase in aspect ratio and decrease in size through adjustment of TEOS, CTAB and Ammonia.

| | CTAB | $H_2O$ | $NH_3$ | TEOS |
|---|---|---|---|---|
| 1 | 0.4 (567 mg) | 1000 (70 ml) | 20 (3.03 ml) | 2.8 (2.41 ml) |
| 2 | 0.8 (1134 mg) | 1000 (70 ml) | 20 (3.03 ml) | 2.8 (2.41 ml) |
| 3 | 0.4 (567 mg) | 1000 (70 ml) | 10 (1.51 ml) | 0.7 (0.6025 ml) |

Protocol for Synthesis of Silica Nanoparticles with the Incorporation of Acrylate Surface Modification for Better in Corporation into Polymer Matrix Nanorods were also synthesized in the same manner with the inclusion of 3-(trimethoxysilyl)propyl methacrylate (3.5 mol % TEOS) with TEOS and Barium Sulfate. The molar ratio of the reaction was 100 TEOS: 14 CTAB: 142,000 $H_2O$: 1428 $NH_3$—$H_2O$. The results are illustrated in FIGS. 11A-11C.

Protocol for the Post-Synthesis Modification of Silica Nanorods

Figure 13:
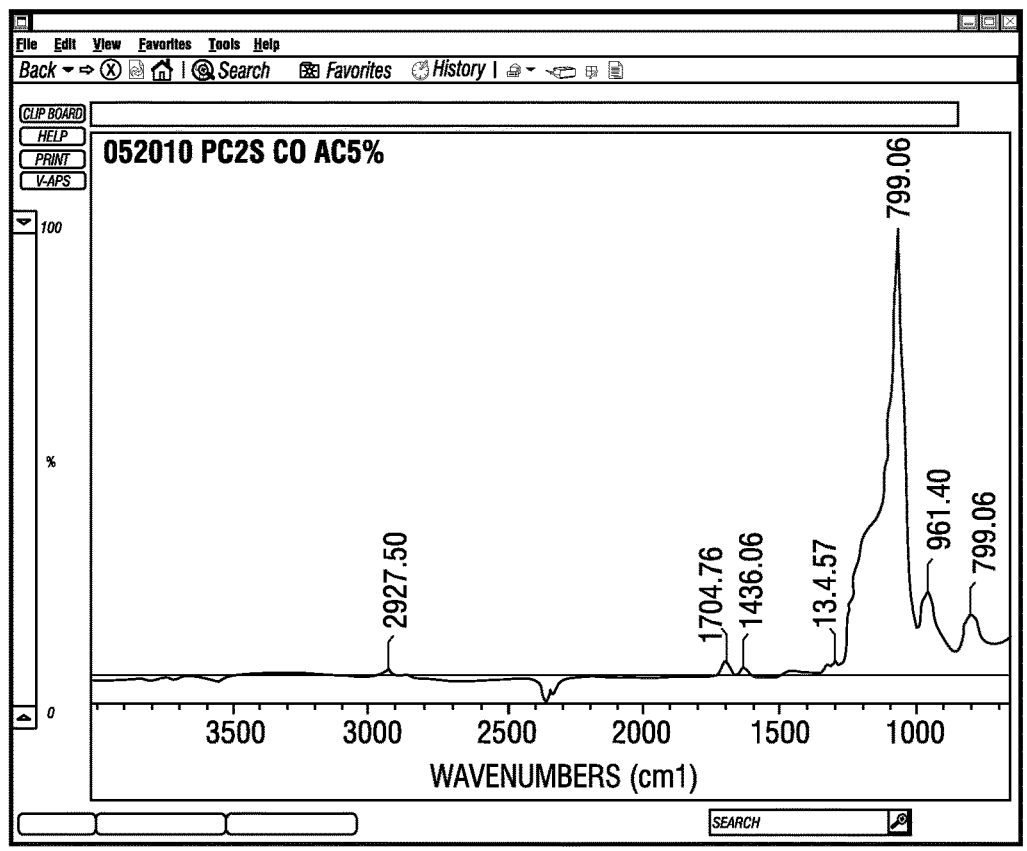
FIG. 13 presents Fourier transform infrared spectrum (FTIR) for post-modified acrylate nanorods showing C=O peaks at 1716 $cm^{-1}$ and C=C peaks at 1621 $cm^{-1}$.
Figure 14:
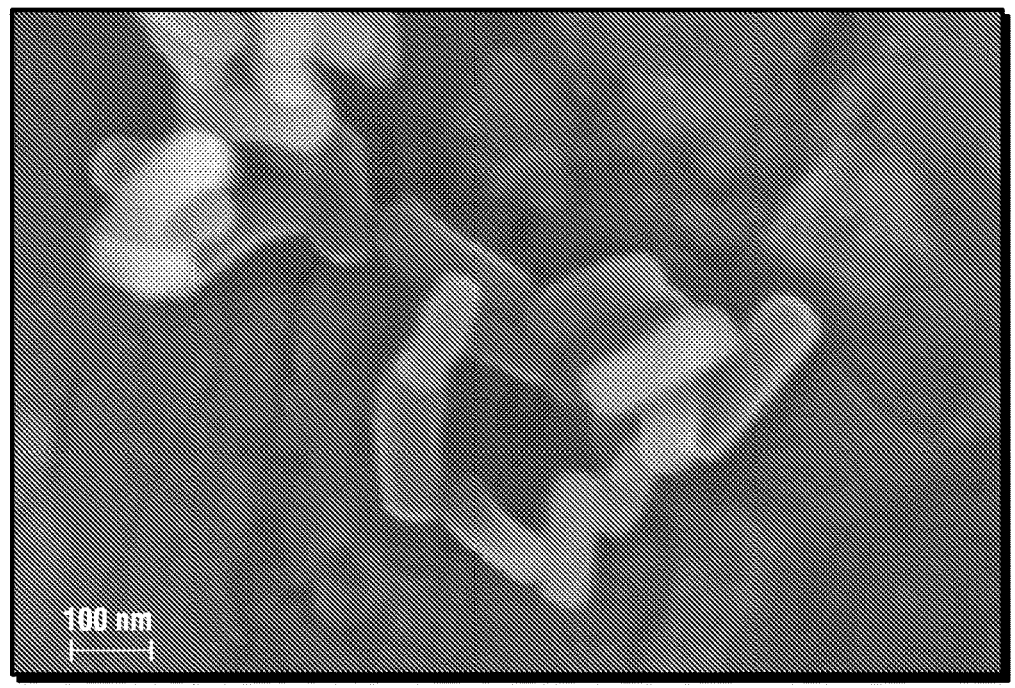
FIGS. 14-16 show silica nanorods with 2.5% trimethoxysilyl propyl methacrylate (FIG. 14); 5% trimethoxysilyl propyl methacrylate (FIG. 15); and 10% trimethoxysilyl propyl methacrylate (FIG. 16).
Figure 15:
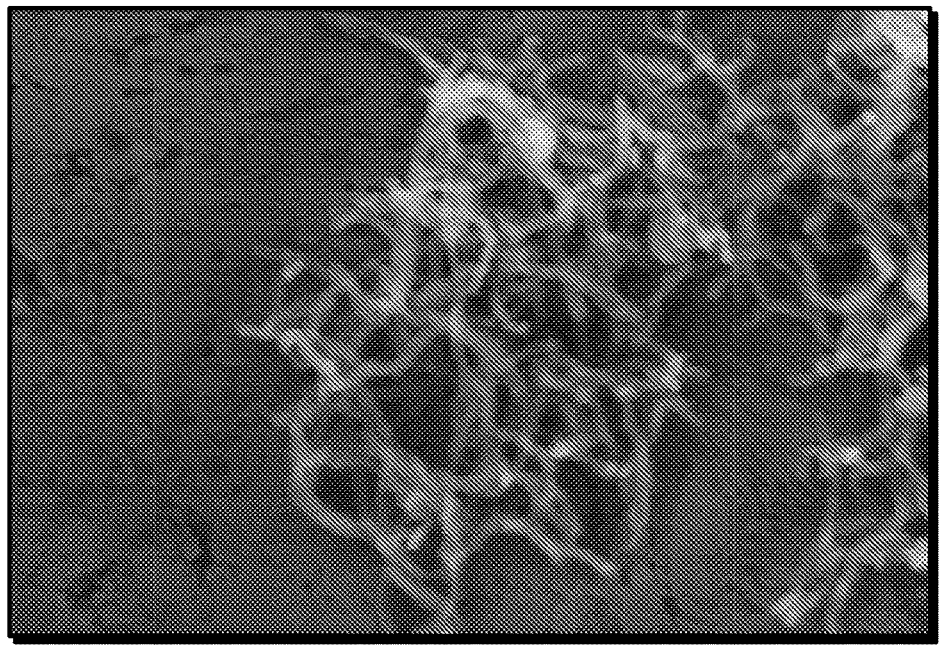
Figure 16:
Figure 17:
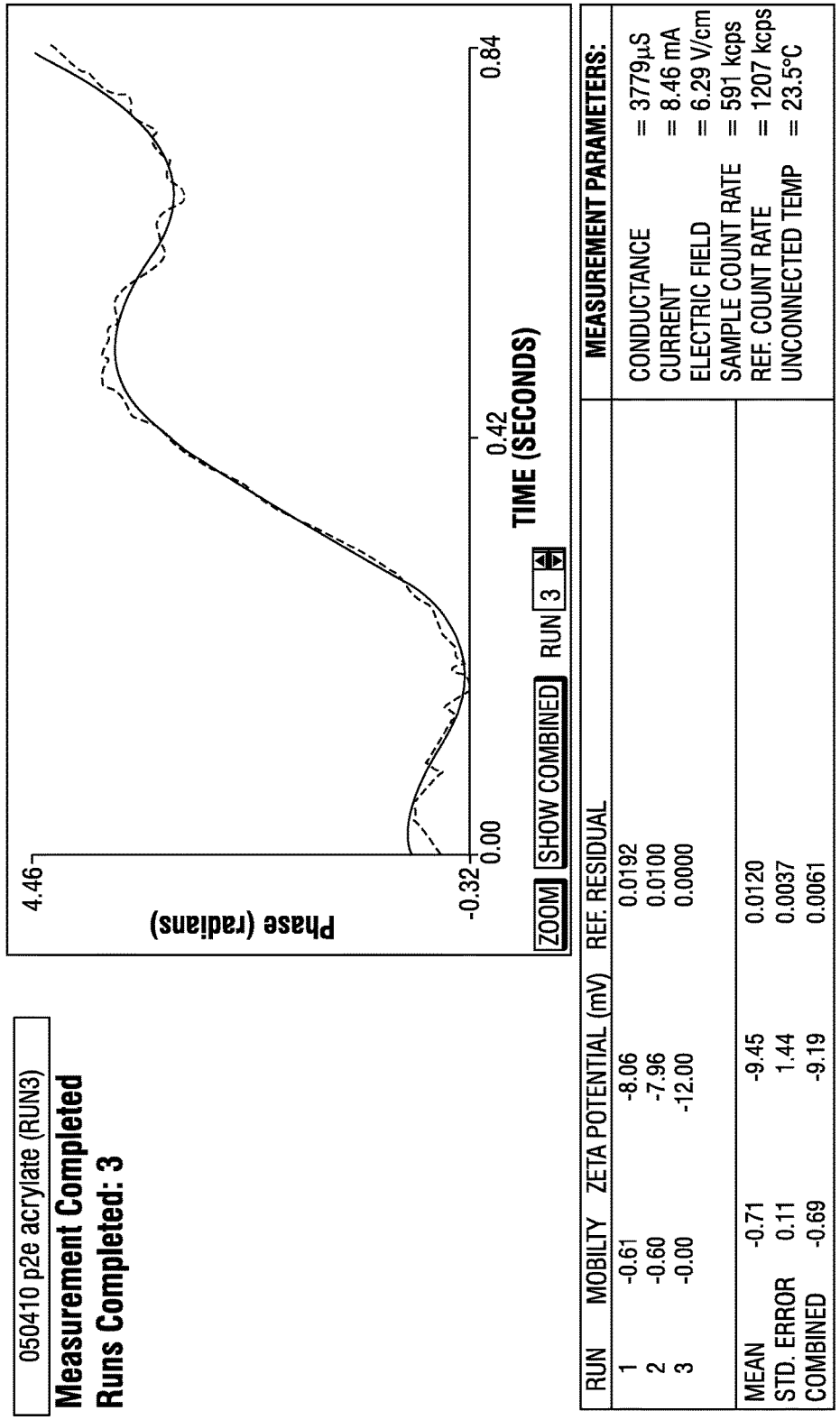
FIG. 17 presents results of measuring zeta potential for co-condensated acrylate particles showing a surface charge of around −17 mV. Oxidized silica (unmodified) has a surface charge of around −40 mV.

20 µl of millipore water was added to 1 mg of particles and sonicated for 10 minutes. A solution of 2.04% acrylate silane and 3.06% Millipore water (optional percentages) in IPA was prepared (980 µl). The solution was mixed at 35° C. at 1300 RPM for 2 hours. After modification, the particles were centrifuged at 13000 rpm for 10 minutes. The supernatant was then removed and replaced with 100% anhydrous IPA for washing. This step was repeated two more times. The supernatant was then removed and the particles were moved to a vacuum oven overnight at 60° C. The results are depicted in FIG. 13.

Characterization of Two Forms of Silica Synthesis and Modification and Barium Incorporation SEM and TEM images of silica nanorods are presented in FIGS. 3A-3D, FIGS. 11A-11C and FIGS. 14-16. Particle morphology of these materials was determined by scanning electron microscopy (SEM) using a (FEI Quanta 400 ESEM FEG). with 10 kV accelerating voltage and 0.005 nA of beam current for imaging. For transmission electron microscopy (TEM) studies, a small aliquot was taken from a suspension of isopropal alcohol and placed in a lacey carbon-coated TEM grid, which was pulled through the suspension and allowed to dry in air. The resulting sample was examined with a Philips model CM-30 TEM operated at 300 kV.

BET (Brunauer-Emmett-Teller) of silica nanorod pore size distribution is presented in FIGS. 19A-19B. The median pore diameter were measured using $N_2$ adsorption/desorption measurements in a Micromeritics ASAP 2000 BET surface analyzer system. The data were evaluated using the Brunauer-Emmett-Teller (BET) and Barrett-Joyner-Halenda (BJH) methods to calculate the size distribution.

Biocompatibility of Silica Nanorods

Figure 20A:
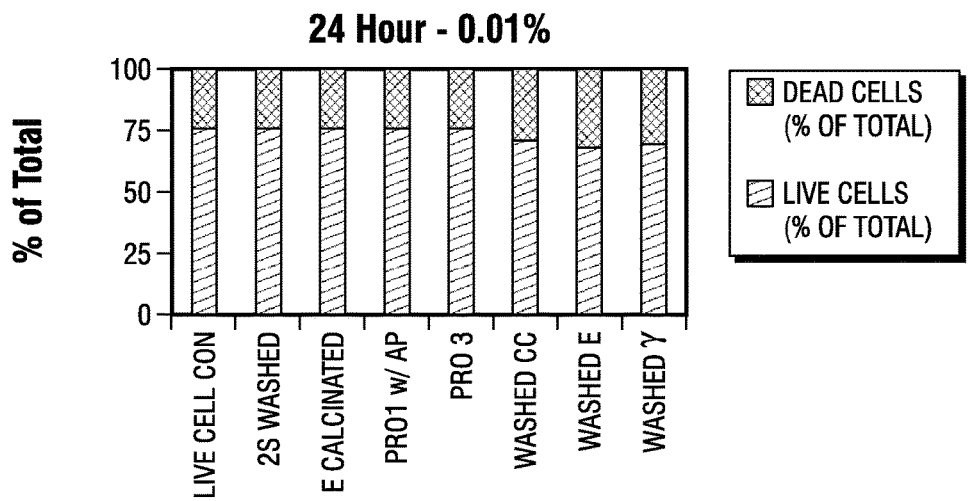
FIGS. 20A-20C demonstrate biocompatibility of mesoporous silica.
Figure 20B:
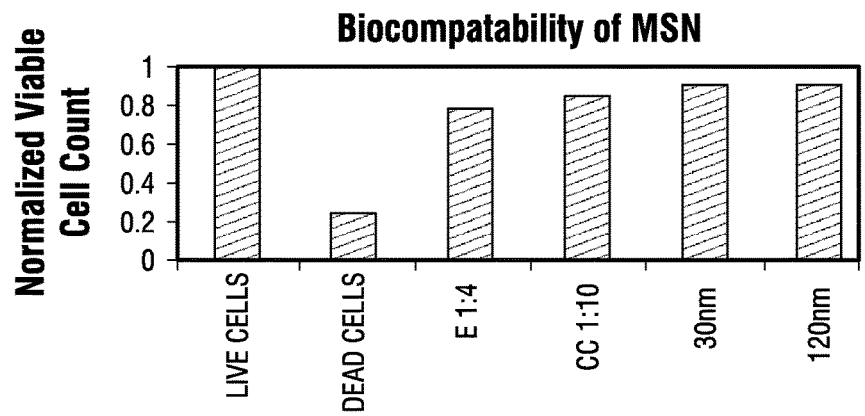
Figure 20C:
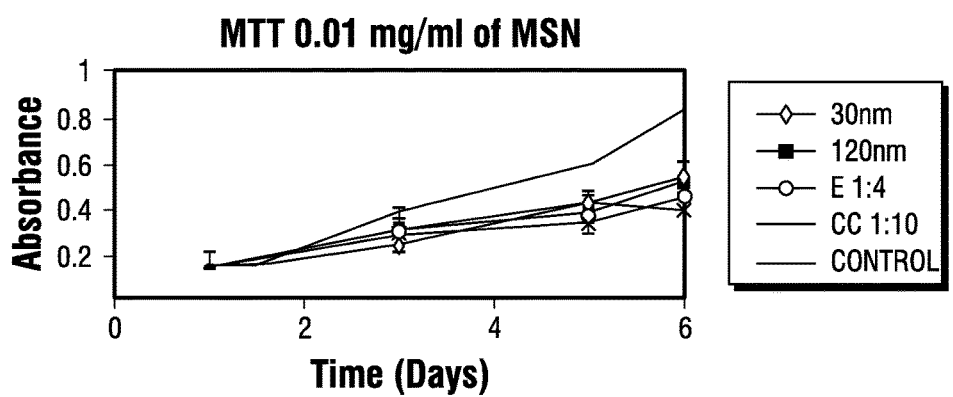

Biocompatibility data for silica nanorods is presented in FIGS. 20A-20C. Acrylate modified silica nanoparticles were dispersed in complete media at a concentration of 0.01 mg/ml. This media was added to MDA 231 cells and allowed to incubate for 8 and 24 hours. After incubation, the media was removed and saved. The cells were then washed with PBS twice, removed from the wells with trypsin, and placed in the corresponding Eppendorf tube containing the original media. Additional fresh media was added to the tubes to stop trypsin activity. The tubes were then centrifuged in at 1,500 rpm for 4 minutes to remove the media. The cells were then washed with Annexin Binding Buffer and centrifuged at 1,500 rpm for 4 minutes to remove the buffer. The samples were then stained with Annexin V conjugated with Alexa Fluor 488. Annexin V is a protein that attaches to phosphatidylserine on the outer surface of the cell only during apoptosis. Staining with Annexin V conjugated with Alexa Fluor 488 will cause apoptotic cells to be fluorescent. The samples were then analyzed for viability using a flow cytometer.

Acrylate modified silica nanoparticles were assessed for biocompatibility. The silica nanoparticles are biocompatible at the concentration of 0.01 mg/ml as seen by the greater than 90% similarity of viability compared to the control cells not incubated with silica nanoparticles.

Next, contrast agents were incorporated to enable the monitoring of the scaffold degradation and tissue infiltration.

X-Ray Detection of Barium Sulfate in Loaded Silica

Figure 21:
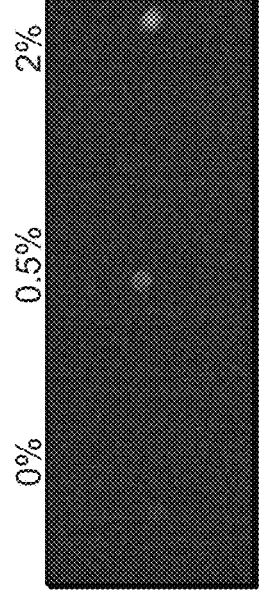
FIG. 21 shows an X-ray image of agarose composites with different concentrations of silica nanorods containing barium sulfate (from right to left: 0%, 0.5% and 2%).
Figure 22:
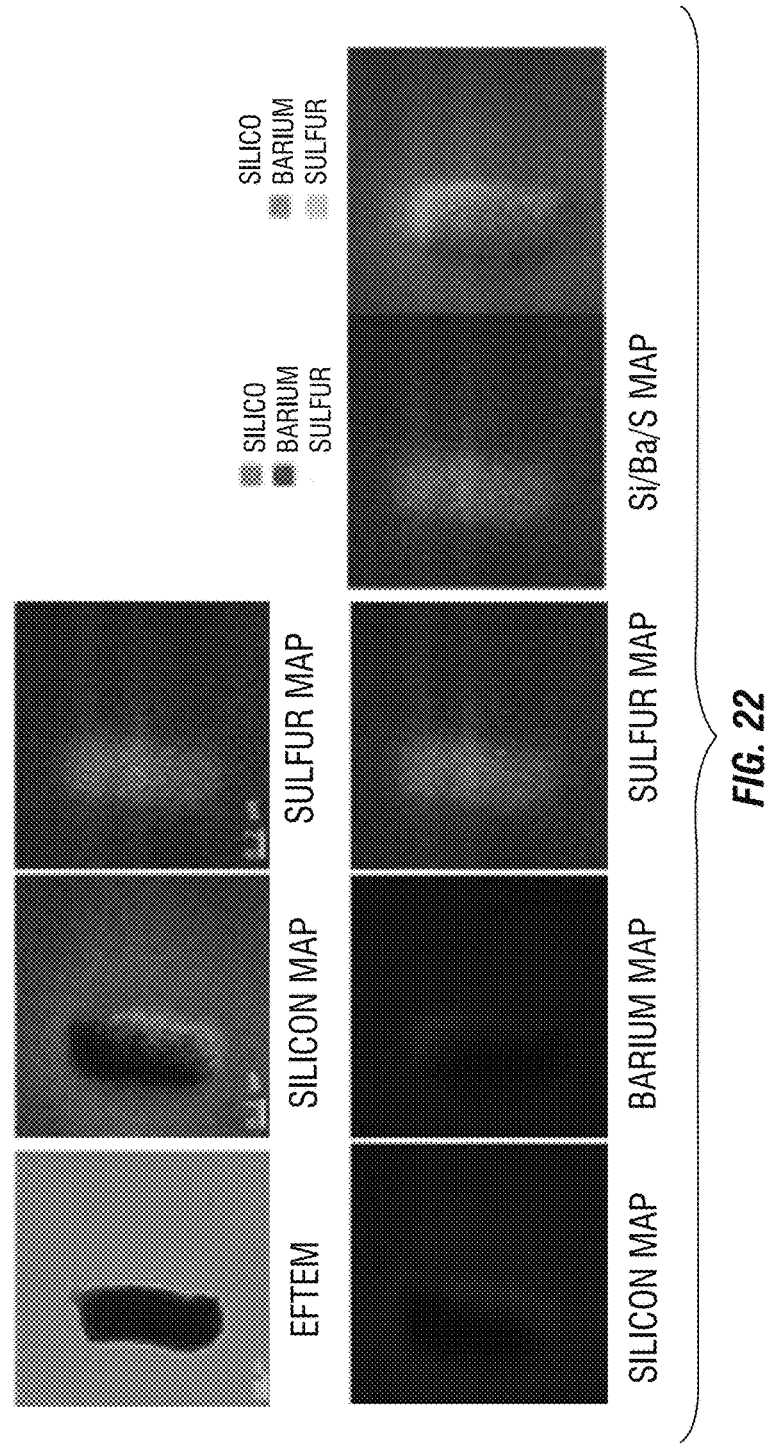
FIG. 22 shows GIF images through TEM showing the presence of barium and sulfur within silica nanorods.

Agarose scaffolds containing Barium Sulfate loaded silica of 0, 2.5 and 5% silica were prepared. Low melt agarose (2.3%) was mixed with barium sulfate loaded silica dispersed in 400 µl of $H_2O$. The mixture was subsequently loaded into cylindrical molds (6 mm×20 mm) and placed in ice for one hr. The agarose rods were place in a high resolution x-ray and read at 85 kV to show the ability to track silica and scaffold degradation through imaging. FIG. 21 shows X-ray image of agarose composite with from right to left 0%, 0.5% and 2% silica nanorods containing barium sulfate. FIG. 22 shows GIF (Gatan Energy Filter) image through TEM showing presence of barium and sulfur within silica nanorods.

Protocol for Loading and Releasing Bioactive Agents into Silica Nanorods

Weigh out 10 mg of dexamethasone and place into eppendorf tube. Add 20 µl of solvent and dissolve the dexamethasone. Add the dexamethasone solution to 1 milligram of particles. Disperse the silica in the solution and place in the thermomixer for 1 hour at 35° C. Centrifuge the particles and remove the supernatant and place it into a labeled tube for loading amount determination. Dry particles. Wash particles before using.

Controlled Release of Glucose, Antibiotics, and Anti-Inflammatory Drugs

Figure 23:
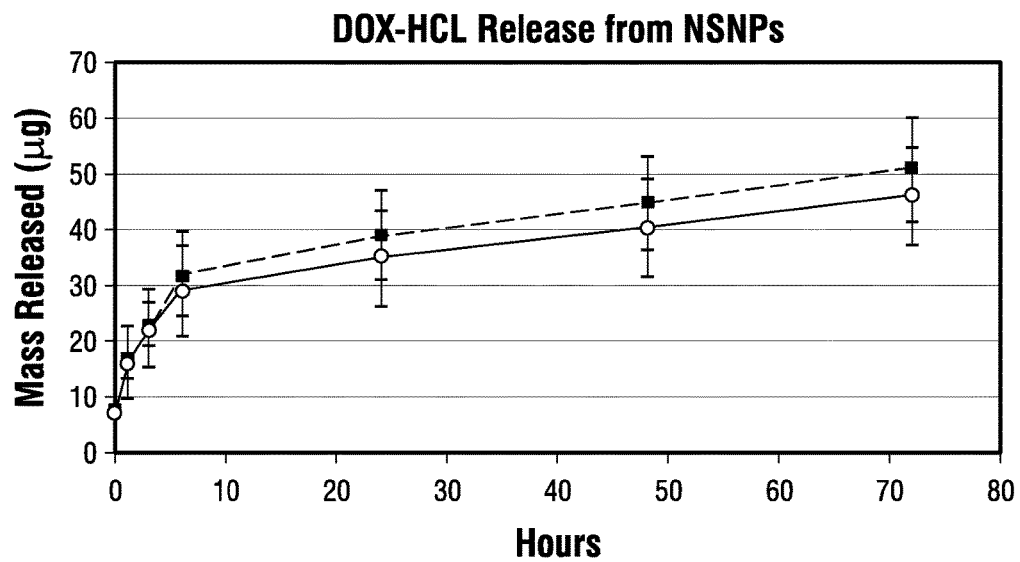
FIG. 23 is a graph demonstrating controlled release of a model drug, DOX-HCl, from silica nanorods.
Figure 24:
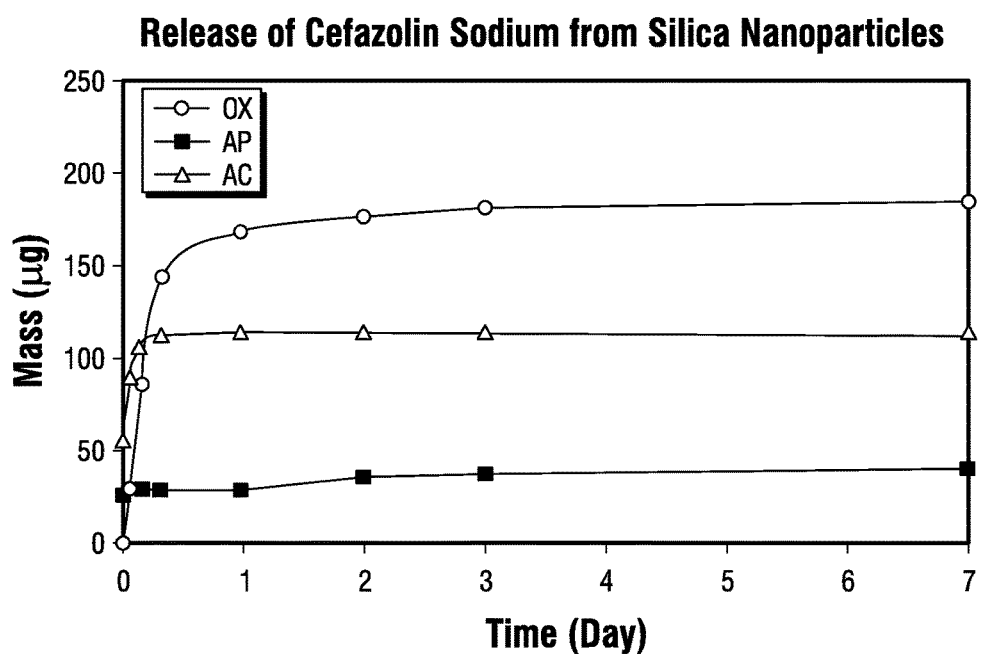
FIG. 24 is a graph demonstrating controlled release of Cefazolin from silica nanorods.

FIG. 23 is a graph demonstrating controlled release of model drug, DOX-HCl, from silica nanorods. FIG. 24 is a graph demonstrating controlled release of Cefazolin from silica nanorods. Next, the porous silica nanorods were dispersed within a polymer matrix.

Nanocomposite Fabrication

PPF was mixed in NVP in a 1:2 mass ratio. Silica nanorods (co-condensated and post modified) were then mixed into the polymer blend at loading concentrations of 2.5, and 5 wt %. The cross-linking initiator, bp, was prepared in a 0.1 g/mL NVP solution and added to the composite mixture at 0.5 wt %. Samples for compressive testing were prepared by pouring the nanocomposite mixture into Teflon molds (6.5 mm diameter, 40 mm length). Samples were subjected to vacuum to remove air bubbles within the polymer and then placed in the oven at 60 degrees. Once dried, samples were cut using a diamond saw into compression testing bars of approximately 6.5 mm diameter and 13 mm height.

Enhancing the Mechanical Properties of Polymer Matrix Through Incorporation of Silica Nanorods Mechanical properties of solid nanocomposite samples were determined by an 858 Material Testing System mechanical testing machine (MTS System Corporation, Eden Prairie, Minn.) with a sample size of five for each group (except for comparison studies with mixed and silica nanorod composites which were conducted with a sample size of three). Compressive mechanical testing was conducted in accordance with ASTM D695-95. Cylindrical samples were placed between two plates as the cross-head lowered onto the sample at a constant rate of 1 mm/min until failure. The cross-head was lowered at a rate of 10 mm/min to the center of each specimen until failure. Force and displacement measurements were recorded and converted to stress and strain based on sample dimensions. The compressive modulus was calculated as the slope of the initial linear region of the stress-strain curve. Compressive fracture strength was calculated as the maximum stress applied prior to failure.

Figure 25A:
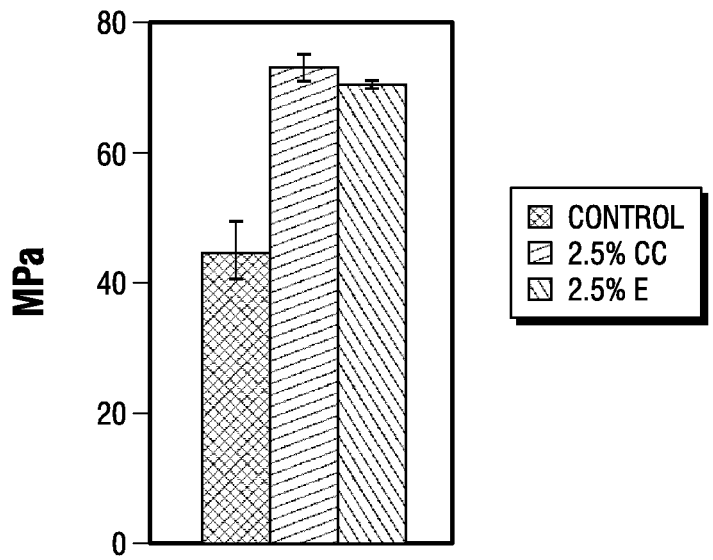
FIGS. 25A-25B show various data related to the mechanical strength of silica nanorods.
Figure 25B:
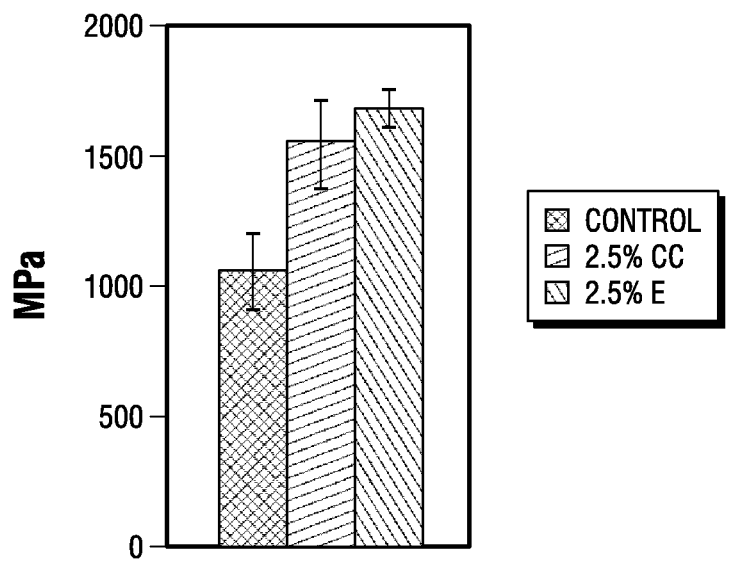

FIG. 25A shows stress offset of control, 2.5% co-condensated silica nanorods (CC) and post-modified silica (E). FIG. 25B shows compressive modulus of 2.5% co-condensated silica nanorods (CC) and post-modified silica when dispersed in PPF polymer.

Enhancing Cell Viability Through the Controlled Release of Glucose into the External Environment of the Scaffold.

Glucose Lactam loading and release was determined as follows. 18.81 mg of 2-keto-D-glucose was weighed out and placed into an eppendorf tube. 250 µL of water was added to dissolve the glucose (final concentration: 75.24 mg/mL). 20 µL of the 2-keto-D-glucose solution was added to 1 milligram of particles. The silica was then dispersed in the solution and placed in the thermo-mixer for 1 hour at 35° C. The particles were then centrifuged. The supernatant was removed and placed into a labeled tube for loading amount determination. The particles were then washed twice with water-save the supernatants and dried for 1 hour in lyophilizer To release the glucose lactam from the silica, the particles were rotated and incubated at 35° C. and centrifuged. The supernatant was removed at 1 hr, 2, hr, 3 hr, 6 hr, 8 hr, 12 hr, 24 hr, 48 hr etc. 200 ul of fresh PBS was then added to the particles and the particles were re-suspended and placed back on the rotator at 35° C. The supernatant at the different time points was then read through a spectrophotometer and measured against a standard curve of glucose lactam to understand the quantity of glucose lactam released.

Enhancing the Osteoconductive Properties of Composite Scaffold Materials

FIG. 26A presents mineralization data showing increase in Calcium and phosphate in the presence of silica. In the sample of the agarose substrate in osteogenic media, where silica nanoparticles are present, there was a higher amount of calcium and phosphate deposited on the surface of the agarose compared to that of the control where the silica nanoparticles are not present (FIG. 26B)

Example 5. Development of Injectable Composite Putty

Simultaneously, we have developed an injectable scaffold featuring in situ setting polymer matrices with alginate-bead based porogens. Through the use of porogens within the putty matrix, the cells, and bioactive molecules loaded within degradable microparticles can be delivered slowly in vivo by the degrading porogen while simultaneously creating pores of optimal size for tissue and blood vessel infiltration. The porogen technique involves dispersing particles, such as hydrogel microspheres in a matrix of scaffold material [7]. After the scaffold material hardens, a composite consisting of the porogen and polymer remains and complete dissolution of the porogen can occur in vivo over time. The end result is a 3D porous scaffold. The porogens will therefore serve three key functions: (1) provide immediate mechanical stability to the scaffold (2) protect and delivers cells and biological molecules essential for accelerating the regenerative process and (3) create pores within the scaffold post-injection to invoke the infiltration of natural bone. The porogens can be tailored to control the pore size and porosity of the scaffold. The size of the porogen sphere determines the size of the pores within the scaffold and the polymer to porogen ratio is what determines the scaffold's porosity. The developed porogen will encapsulate the growth factor-releasing nanoporous silicon enclosures (NSE), bioactive PA, MSC, and a nutrient rich cocktail of PRP prior to injection. Once injected, the physiological fluid will degrade the porogen thereby releasing the contents into the surrounding environment and creating a porous structure.

The alginate beads were combined with PPF to form a composite putty capable of in situ cross-linking after injection into a fracture site. While PPF cross-linking causes significantly less exothermic heating than PMMA, we supplemented the PPF phase with pre-cross-linked (but still chemically viable) PPF microparticles to serve as a "heat sink" and minimize exothermic reactions in vivo. It was found that by including pre-polymerized PPF particulates into the putty, peak temperature reached only 10° C. above body temperature for a duration of 1 to 3 minutes (FIG. 26C). The addition of 15% pre-cross-linked PPF dampened the temperature increase by half. Peak temperature occurred at 1 minute 45 seconds. An increase of 5-6° C. within the bone is comparable to a fever and biologically acceptable. Mechanical testing that followed indicated no loss in compressive strength due to using pre-polymerized PPF.

To test the compressive strength of the putty, PPF and PPF-alginate bead composite scaffolds were fabricated in cylindrical Teflon molds. It was observed that the addition of porogen beads significantly increased the compressive modulus of the material compared to porous scaffolds and closely matched that of trabecular bone, the intended tissue for regeneration (FIG. 8A).

In sum, mesoporous silicon nanorods can incorporate the following five properties: 1) mechanical reinforcement of the polymer matrix; 2) delivery of active agents, such as bioactive molecules; 3) mineral deposition, 4) increase in cell viability and 5) provide imaging/monitoring capability through incorporation of imaging agents, such as contrast agents into the porous silica nanorod.

Example 6. Surface Functionalization of Mesoporous Particles for the Sustained Delivery of Antibiotics for Orthopedic Applications The present inventors discovered that functionalization of a surface of porous or mesoporous particle with a polymer may provide for a sustained release of an active agent, such as a therapeutic and/or imaging agent, contained in the particle's pores.

SUMMARY AND BACKGROUND

Bacterial infection is one of the most common problems after orthopedic implant surgery. If not prevented, bacterial infection may result in serious and life threatening conditions, such as osteomyelitis, which has shown a great necessitate for local antibiotic delivery systems in the treatment of infections. Mesoporous silicon (MPS) with antibiotics may be one of the relevant approaches for obtaining a controlled drug release. To characterize MPS, surface charge, surface modification and size distribution, and in vitro antibiotic release from them were carried out. HPLC and UV spectroscopy were used for the assay of two different antibiotics: Cefazolin and Clindamycin sodium and the assays method were validated. MPS with 10-100 µL diameter having 200 nm in length obtained by etching technique and sorted by centrifugation are used in this study as novel drug delivery. It has shown that surface modification of MPS leads to decelerating the release of the integrated antibiotics. As well, biodegradability of MPS in phosphate buffer saline (PBS) solution was demonstrated.

Such antibiotic release from the MPS may provide more reliable antibiotic protection at a targeted site of a bone defect.

Despite particular treatment, open fractures (broken bones in communication with the environment) present high rates of complications because of the risk of bacterial infections and chronic osteomyelitis that can threaten the viability of the limb and even the life of the patient. Standard care for open fractures requires irrigation, debridement, stabilization, and antibiotic therapy and often results in multiple procedures according to the severity of the wound and the onset of infections. [1]

The lack of proper control over a drug release rate and target delivery area is a huge disadvantage for conventional drug tablets. Tablets tend to provide rapid and immediate release of therapeutic agents and require more frequent and repeated dosages for maintaining therapeutic levels, causing unwanted fluctuations in drug amounts delivered to the blood and tissue. In order to circumvent problems in drug adsorption, metabolism, and irregular concentrations and to optimize the therapy itself, a controlled release dosage is advantageous over conventional tablets. Biomaterials with nanoscale features have become increasingly popular as controlled release reservoirs for drug delivery. Nanoscale drug delivery systems may be able potentially tune release kinetics, enhance availability and distribution over time, and minimize toxic side effects, thus increasing the therapeutic effect of a given drug. Localization, controlled release, and sustainability of drugs over long periods of time within the body may be some of the challenges in the design of effective drug therapies.

Delivery systems able to release antibiotics over an extended period of time may solve all these issues and provide efficacious alternative solutions to the current approaches. The objective of this study is to prove that MesoPorous Silicon (MPS) may be effectively used in combination with orthopedic implants and/or with scaffolds for bone tissue engineering to reduce the onset of infections and to enhance the ability of bone to heal in a timely fashion. MPS may offer significant advantageous properties for drug delivery applications as it favorably extend drug pharmacokinetics, stability as well as bio-absorbability.

Biodegradable MPS with well-controlled shapes, sizes and pores have been developed. [2] The size of the pores may confine the space for the entrapment of the antibiotic of choice while MPS surface chemistry may affect the stability and duration of its interaction with the antibiotic. The size of the pores and the surface chemistry can be easily altered and controlled to tune release kinetics. The ability to load drugs within the porous matrix of the particle at room temperature enabled the use of MPS also with sensitive compounds susceptible to temperature dependent degradation or inactivation.

Mesoporous Silicon Fabrication

Porous silicon fragments were produced by fractionation of sonicated multilayer porous silicon films. The multilayers were produced by anodic etch of a 100 mm p++ Si wafer in a 1:2 HF:Ethanol solution. A 5 A current was applied for 2-6 s followed by a 2 A current for 20 s. The two step process was repeated for 30 cycles with a stop of 8 s in between each cycle. Finally a release current of 7 A was applied for 5 s. The wafer was rinsed in DI water and briefly sonicated in isopropanol to detach the porous layer. The porous silicon suspension in isopropanol was transferred to a glass bottle and sonicated for 24 hours to reduce average fragment size. Successive centrifugation steps fractionated the obtained porous silicon fragments. Initial centrifugation at 4300 rpm sedimented the micron and supra-micron fraction. The supernatants were transferred to Oak Ridge Teflon Centrifuge Tubes, and centrifuged at 10K×g RCF using a Beckman Ultracentrifuge to sediment the sub-micron fraction. The supernatants were centrifuged again at 26K×g RCF to sediment the low sub-micron fraction, while the nanometric fraction remained suspended and kept in solution. After centrifugation, fragments were fractionated into micron, sub-micron, low sub-micron, and nanometer ranges. We characterized each production lot by SEM verifying their compliance to the required standards. The fragments were oxidized in hydrogen peroxide solution.

Particle Size Distribution

5 µL of resuspended 20 ml of Isopropanol mixture of MPS in solution was diluted in 10 mL double filtered Isotonic solution, ultrasonicated for a few seconds, and subjected to inverting for few times before measurement to achieve well mixing. MPS were then sized using a Beckman Mutisizer IV. Triplicate analyses were made on each suspension, which corresponded to a single batch. Results are expressed as the mean MPS diameter (mm) of the three batches as a function of volume (%).

MPS Surface Charge

5 µL of resuspended 20 ml of Isopropanol mixture of MPS in solution was washed and diluted in 1400 µL 10 mM 7.4 pH Phosphate buffer, ultrasonicated for a few seconds, and subjected to vortexing for 5 minutes to prevent aggregation. MPS were then analyzed using a Brookhaven Zeta potential analyzer. Triplicate analyses were made on each suspension, which corresponded to a single batch. Results are expressed as the mean MPS surface charge of the three batches.

MPS Surface Modification

The mesoporous silicon were transfer to premeasured ultra-centrifuge tubes. They were spanned down using Beckman Coulter Ultracentrifuge at 12000 RPM for 20 min at 4° C. The supernatant of each vial was removed and stored separately. The fragments were dried out using vacuum oven for approximately 2-4 hour depends upon volume of the fraction at 75-80° C. The mass of the dried fragments was measured before proceed to oxidation step. 4 mL of $H_2O_2$ were Added to each tubing and shaked for a few times by hand and left for 2-3 hours. Each sample was sonicated for 1-2 minutes. The sonicated sample was placed in the oven set at 90° C. for 2 hours to be completely oxidized. Isopropanol alcohol (IPA) was added to cover 1 cm above the height of the dried-out fragments level. The samples were washed 3× with IPA.

Loading of Antibiotics

At room temperature (25° C.), the MPS samples were placed in a vacuum (10-4 Torr) for approximately 20-30 min to rid nanopores of any trapped alcohol. The high concentration antibiotic solution loaded was 1 mg/mL of each antibiotics (from Sigma Aldrich). The samples were incubated for 2 hours to allow sufficient time for the drug to fully penetrate into pore structure and then the drug-loaded MPS samples were washed two times with phosphate-buffered saline (PBS), pH 7.2 (GIBCO).

Agarose Coated MPS 5 mg and 10 mg of agarose (Sigma) were reconstituted into 1 mL of deionized water respectively and the well-mixed powder was melted at 65 C for 20 minutes and cool down to 37 C. Then, 20 µL of agarose solution was added 20 uL of fragments loaded, suspended and sonicated. The samples were mix and stored in the thermo-shaker for 15 min. The samples were centrifuged down (10 min; 14000 rpm; 37 C) and the supernatant was collected while the solution was still warm. Then, the samples were resuspended in deionized water and sonicated for few min.

Gelatin Coated MPS

All MPS were coated by modified hot-melt method. The well-mixed gelatin powder was melted at 65 C and brought to 37 C. The mixture was then diluted into two concentration solutions, and cooled at room temperature. The resulting coated MPS were washed and dried in vacuum.

Release Studies

MPS samples were individually incubated in a humidified 95% air/5% v/v CO2 incubator at 37° C. in 500 µL of fresh PBS. At designated time points, 500 µL of the release medium was exchanged and the antibiotic concentration was determined as described below.

Quantification of Antibiotic Concentrations

Both drugs have characteristic spectra by UV-VIS (ultraviolet and visible light) absorption spectroscopy with peaks at 210 nm and 270 nm for Clindamycin and Cefazolin, respectively. With drug standards ranging from 1 to 200 µg/mL, absorbance calibration curves obtained at these peak wavelengths gave linear graphs with correlation coefficients greater than 0.98. High performance liquid chromatography (HPLC) methods were used to further investigate Clindamycin and Cefazolin release from MPS. HPLC was performed with a Hitachi chromatography system with LaChrom software control. The chromatography system used a Agilent Technologies Zorbax Eclipse Plus C18, a 50-µL injection volume, detection at 210 nm and 270 nm and a mobile phase was composed of 0.05M Monobasic Potassium Phosphate: Acetonitrile: Tetrahydrofuran) (76.5:23.0:0.5, v/v/v), at a flow rate of 1 mL/min Calibration graphs were linear in the 1-200 µg/mL concentration range. A relatively good resolution of Clindamycin peak from interferences was achieved at retention time between 1.3-1.5 min.

Scanning Electron Microscopy (SEM) Analysis

MPS were observed by scanning electron microscopy. Samples were washed with ethanol. Specimens were mounted on SEM stubs (Ted Pella, Inc.) using conductive adhesive tape (12 mm OD PELCO Tabs, Ted Pella, Inc.). Samples were sputter coated with a 10 nm layer of gold using a Plasma Sciences CrC-150 Sputtering System (Torr International, Inc.). SEM images were acquired under high vacuum condition, at 20 kV, spot size 3.0-5.0, using an FEI Quanta 400 FEG ESEM equipped with an SE detector.

Results and Discussion

The release of antibiotics from non coated MPS was characterized by a 30% burst within the first day (FIG. 27) and subsequent release of remaining antibiotics within 4-6 days. In contrast, surface coated MPS released only 10-15% within first day. Substantial release was completed within 6 days. Bare MPS controls, without any surface modification, showed 60-70% antibiotic release within 1-2 days as expected. This proved that the nanostructures of MPS pores were controlling the sustained drug release. This shape of release profile was similar for both antibiotics from MPS. Nevertheless, a near sustain drug release was achieved over 5-6 days with an average release rate over all the time points was 400-500 µg. The desired release profile for many drugs would follow this type of sustained release so that the drug levels in the body remain constant while the drug is being introduced.

FIGS. 28 and 29 illustrate the accumulative release profile of Cefazolin within 5-6 days from MPS agarose and APTES coated, respectively. MPS matrix degradation over time was evaluated with flow cytometric analysis and multisizer analysis, as shown in FIGS. 30A-30C and 31, respectively.

FIGS. 32 and 33 show FACS analyses of the MPS. FIGS. 34A-34B present zeta potential of differently surface modified MPS.

Morphological Changes

To clarify the release mechanism, MPS morphology was studied by SEM during course of release. The images of MPS matrix loaded with antibiotics have been showing significant dissolution of the drug due to the porosity and surface degradation of the MPS matrix nanostructure which can be tailored for some biomedical applications.

In our MPS delivery system and as it has been suggested by others, an active carrier system can sometimes be a part of an additional treatment in terms of contribution to the healing of the surrounding environment tissue. Another benefit of silicon degradation byproduct is that it is nontoxic. Cefazolin and Clindamycin are few examples of common pharmaceutical antibiotics that reduce the bacteria biofilm formation which were used as a model drug for this study.

Current advanced drug delivery improves delivery efficiency and localization which may directly reduce prescribed dosages to the patient. In medical practice, antibiotics are given in large dosages but, controlled sustained release, would help reduce the toxic side effects, drug waste, and additional complications. In addition, the sustained release from MPS may be tailored to provide the correct therapeutic dose to avoid adverse effects. Other properties, such as interactions between drug and matrix, pore size, pore geometry, and matrix reactions with surrounding media are just a few other aspects needed to be considered for controlled drug delivery system design.

REFERENCES

[1] Starr A J. J Bone Joint Surg Am. 2008 February: 90 Suppl 1:132-7.
[2] Tasciotti E, Liu X, Bhavane R, Plant K, Leonard A D, Price B K, Cheng M M, Decuzzi P, Tour J M, Robertson F, Ferrari M. Nat Nanotechnol. 2008 March; 3(3):151-7. Epub 2008 March
[3] Chiappini, Ciro., Tasciotti, E., Fakhoury, J. R, Fine, D., Pullan, L., Wang, Y C, Fu, L., Liu, X, Ferrari, M. J ChemPhysChem.[In Press].
[4] Vallet-Regi M. 2006. Chem Eur J 12:5934-5943.
[5] Horcajada P, Ramila A, Perez-Pariente J, Vallet-Regi M. 2004. Micropor mesopor mater 68:105-109.

Example 7. Agarose Surface Coating Influences Intracellular Accumulation and Enhances Payload Stability of a Nano-Delivery System Protein therapeutics often requires repeated administrations of the drug over a long period of time. Proteins' instability is a major obstacle to the development of systems for their controlled and sustained release. In this work we describe a surface modification of nanoporous silicon particles (NSP) with an agarose hydrogel matrix that enhances their ability to load and release proteins, influencing intracellular delivery and preserving molecular stability.

We developed and characterized an agarose surface modification of NSP. Stability of the released protein after enzymatic treatment of loaded particles was evaluated with SDS-page and HPLC analysis. FITC-conjugated BSA was chosen as probe protein and intracellular delivery evaluated by fluorescence microscopy.

We showed that agarose coating does not affect NPS protein release rate while fewer digestion products were found in the released solution after all the enzymatic treatments. Confocal images show that the hydrogel coating improves intracellular delivery, specifically within the nucleus, without affecting the internalization process.

This modification of porous silicon adds to its tunability, biocompatibility and biodegradability, the ability to preserve protein integrity during delivery without affecting release rates and internalization dynamics. Moreover it may allow the silicon particles to function as protein carriers that enable control of cell function.

During the last few decades protein therapeutics has developed dramatically and gained a significant role in many fields of medicine (1). Proteins such as growth factors, hormones, and cytokines are achieving widespread recognition as therapeutic agents (2), while protein epitopes are now being mapped and used for vaccination that provides broad protection against infectious agents (3). Various therapeutic proteins have been proposed in the literature with a wide range of roles and functions in the body (4-7): formation of receptor domains on the cell surface, improvement of the intracellular and/or extracellular molecular transport, enzymatic catalysis of biochemical reactions, enzymatic or regulatory activity, targeting, vaccines (8, 9) and diagnostics (10-12). Protein drugs are able to act selectively on biological pathways but often require repeated administration, making their clinical use even more challenging than that of conventional drugs (13-16). The controlled and sustained release of proteins may enhance their therapeutic efficacy and reduce the pain and inconvenience of frequent injections. However, this route of administration faces a single major issue: protein instability (17). Proteins are unstable molecules and once injected in the bloodstream they are rapidly degraded and deactivated by specific enzymes (18). Growth factors such as FGF and VEGF, for example, have half-life as short as 3 and 50 minutes respectively (19, 20). Furthermore sustained release (days to months) and formulation of the delivery system often exposes the protein to harmful conditions that disrupt its integrity and ultimately compromises its therapeutic efficacy (21, 22).

In the past years, many drug-delivery systems have been developed. Some organic ones (e.g liposomes, micelles, nanoparticles) are able to deliver drugs to a specific site and at the desired rate; yet, most of these systems are rapidly eliminated by the reticulum endothelial system (RES). Furthermore, polymeric formulations (such as PLGA), release acidic byproducts upon degradation, and can induce local inflammatory responses that negatively impact protein integrity and activity (23, 24).

Porous silicon (pSi) has been proposed as an ideal biomaterial for drug delivery thanks to its biocompatibility (25, 26), tunability of the porous structure (27, 28), ease and versatility of processing through standard semiconductor technology (29, 30), and for the well established protocols for the optimization of its surface chemistry (31, 32). As a result, pSi has been successfully used to improve drug solubility, increase bioavailability, and modulate release rates, thus paving a promising path for the realization of pSi drug delivery devices (33-35). pSi has been successfully employed for the loading and release of peptides, proteins and nanoparticles in a controlled and sustained fashion (35-38). Peptides loaded into porous silicon particles have been systemically delivered in vivo resulting in a prolonged effect compared to their free administration (39). Post synthesis modification of pSi provided controlled release and enhanced loading of bioactive molecules (33, 36, 37, 40). However, the stability of the loaded/encapsulated protein has not been guaranteed thus far.

This work describes a novel surface modification with agarose hydrogel developed to enhance protein stability within nanoporous silicon particles (NSP) during sustained and controlled release, and during enzymatic digestion. Moreover we report the coating's control over NSP intracellular trafficking and uptake. The enhancements to protein delivery of this NSP surface matrix coating may extend the use of pSi as a versatile delivery system for enzymes, vaccine antigens, and protein therapeutics in general.

Nanoporous Silicon Particles Synthesis and APTES Modification

NSP were designed and fabricated in the Microelectronics Research Center at The University of Texas at Austin by established methods (29, 35). In brief, after low pressure chemical vapor deposition of 100 nm silicon nitride (SiN), photoresist was spun cast on a 100 mm, 0.005 Ω-cm p-type Si wafer. A pattern consisting of 2 μm dark field circles with 2 μm pitch was transferred to the photoresist by contact photolitography. Then the pattern was transferred for 100 nm into the silicon substrate by reactive ion etching with $CF_4$ gas. The photoresist was removed from the substrate for anodic etch preparation by piranha clean. The porous particles were formed by selective porosification through the SiN mask by anodic etch. The SiN layer was removed by soaking in HF, the substrate was dried and the particles were released in isopropanol by sonication. Particles were then oxidized by piranha (solution of 2:1 vol. H2SO4 (96%) in H2O2 (30%)) for 2 h at 120° C. Then modified with aminopropyltriethoxysilane (APTES—2% in IPA) for 2 hours at 35° C. to provide a controlled positive charge to the particle surface that enhances protein loading capacity.

Modification of Nanoporous Silicon Particles with Agarose Matrix

Agarose coating was performed by suspending NSP in warm (40° C.) agarose solution for 15 minutes and then the solution was cooled at 4° C. for 30 min. Agarose coating solutions were prepared at different concentrations ranging from 0.05 to 0.5%$_w$ with low melt certified agarose (BIO-RAD), used as received. To remove excess gel, particles were washed with warm PBS (35° C.) and cooled at room temperature twice. Agarose coating of loaded NSP was performed after loading before any washing step.

NSP Characterization

The volume, size and concentration NSPs were characterized by a Multisizer™ 4 Coulter Counter (Beckman Coulter). Before the analysis, the samples were dispersed in the balanced electrolyte solution (ISOTON VR II Diluent, Beckman Coulter Fullerton, Calif.) and sonicated for 5 s to ensure a homogenous dispersion. Their surface charge before and after APTES modification and agarose coating was measured in a PB buffer at pH 7.4 using a ZetaPALS Zeta Potential Analyzer (Brookhaven Instruments Corporation; Holtsville, N.Y.). The surface area and pore size distribution of the NSPs were measured using N2 adsorption-desorption isotherms on a Quantachrome Autosorb-3B Surface Analyzer. To prepare the sample, 10 mg of NSPs was transferred to a sample cell, and dried in a vacuum oven at 80° C.

The sample was degassed at 200° C. for 12 hours, and the N2 adsorption-desorption isotherm was measured at 77K over the relative pressure (P/PO) range of 0.015-0.995. Nanopore size distributions and porosities were calculated from the desorption branch of the isotherms using the BJH model. NSP size and shape was also evaluated at different timepoints during incubation in PBS at room temperature by scanning electron microscope (SEM) (FEI Quanta 400 ESEM FEG). To prepare SEM sample, a drop of PSN IPA solution is directly placed on a clean aluminum SEM sample stub and dried. Ag samples were sputter-coated with gold for 2 min at 10 nm layer using a CrC-150 Sputtering System (Torr International, New Windsor, N.Y.). All the samples were loaded in SEM chamber, and SEM images were measured at 5 kV and 3-5 mm working distance using an In-lens detector. Size variation over time was also examined by fluorescence activated cell sorting (FACS) (Becton Dickinson, FACSCalibur). Solution pH was measured with pH strips (colorPHast—EMD).

Protein Loading and Release

Lyophilized and fluorescein isothiocyanate (FITC) conjugated bovine serum albumin (BSA) was chosen as a protein probe, purchased from Sigma-Aldrich, and used as received. BSA was loaded into NSP by suspending $10^8$ NSP in 200 µL of 25 mg/mL BSA (1.2% of BSA was FITC-conjugated) aqueous solution (prepared in PBS—GIBCO Invitrogen). The suspension was continuously mixed in dark at 4° C. for 2 hours, then spun down and the supernatant was removed. To remove excess of probe three washing steps were performed. Coated and not coated particles underwent the same number of washing steps.

To measure the loading efficiency of NSP, the fluorescence and concentration of the BSA solution used for the loading (as prepared for the loading procedure and as recovered after incubation), was quantified by spectrofluorimetry with SpectraMax M2 spectrophotometer (Molecular Devices). The BSA loss during coating procedure was also taken into account by measuring coating and washing solutions fluorescence/concentration.

Protein release over time from NSP (bare (not coated—NC) and agarose coated (Ag) with two agarose concentrations (0.05 and 0.125%$_w$)), was studied by collecting all the supernatants and replacing them with fresh PBS at each timepoint. Release quantification was performed measuring protein content in the supernatant with the Bradford method, by spectrofluorimetry and by FACS (Becton Dickinson, FACSCalibur).

Protein Stability Analysis

NC and Ag (0.125%) NSP loaded with BSA, were treated with trypsin (25 µg/mL) for different times and enzymatic digestion was ended adding equal volume of bleaching solution (20% acetonitrile-$CH_3CN$ and 4% trifluoroacetic acid-TFA in water) at the different time points. The structural integrity of the BSA, released after 24 hours from NC and Ag NSP after the different trypsin treatments, was analyzed with sodium dodecyl sulfate polyacrylamide gel electrophoresis (SDS-page) using Criterion Tris-HCl Gel (BioRad) in non reduced condition and high performance liquid chromatography (HPLC) (ELITE LaChrome, Itachi). Digestion products were also quantified analyzing SDS page silver stained bars with ImageJ.

Cell Culture and Confocal Microscopy

Human umbilical vein endothelial cells (HUVEC) were cultured in complete Dulbecco's modified eagle's medium (DMEM) at 37° C. and in 5% $CO_2$ using 2 different systems: (a) 4 chamber tissue culture treated glass slides and (b) circular glass coverslip of 8 mm diameter placed in 12 well plates. 120,000 and 240,000 cells were seeded per chamber and well respectively. Cells were allowed to settle for 2 hours before adding NSP. On the glass slide 600,000 NC or Ag NSP loaded with BSA FITC-conjugated were added directly to the cells in each chamber and incubated for 24 and 48 hours. In the multi-well plate 1,200,000 NC or Ag NSP loaded with BSA FITC-conjugated were added in a transwell over the cells to each well, avoiding direct contact between cells and NSP.

Cellular internalization of NSP and uptake of BSA were observed for both systems by confocal microscopy (Leica MD 6000) after 24 and 48 hours incubation with Ag or NC particles. Cells were stained with fluorescent phalloidin (actin filaments) and DRAQ5 (nuclei) after fixation in 4% paraformaldehyde. Cellular uptake of BSA from 1 mg/mL BSA-FITC conjugated solution prepared in DMEM was also evaluated. All images used for quantification were acquired by keeping the same acquisition setting (pinhole, gain, laser power, optical path, line average, zoom and image resolution) for the whole duration of the experiment. Numerical evaluation of the fluorescence was performed using the Nikon Elements software. The average fluorescence within the cytoplasm or the nuclei was measured in different, representative field of views (at least 5 cells per image per timepoint). Cellular uptake of BSA from protein dispersed in solution was not numerically quantified because by using the same confocal setting most of the cells appeared supersaturated thus not allowing a direct comparison between the two conditions.

Statistical Analysis

Reported data are the averages of at least three different measurements, and statistical significance ($p<0.05$) was evaluated with ANOVA (Origin), if not otherwise stated in the text.

Characterization of Nanoporous Silicon Particles

NSP used in this work are quasi-hemispherical shells of 3.2 µm diameter and 600 nm shell thickness (FIG. 35A and FIG. 35F) designed for drug delivery application(41). Pore size is 15 nm with 51% porosity as estimated from the desorption branch of nitrogen adsorption/desorption isotherms. APTES modification altered particles' surface charge (zeta potential from −23 mV to +1 mV) and allowed the loading of about 10 µg of BSA per million of NSP (7 µg). BSA is negatively charged and could not be loaded in oxidized particles (loaded particle zeta potential was −28 mV).

The agarose coating was developed and optimized to assure a protective function against harmful agents during long-term release. SEM images (FIGS. 35B-35E) indicated that the resulting agarose coating was uniform and density increased with agarose concentration. Agarose hydrogel matrix filled the pores and covered the particles' surface completely but did not alter appreciably the size and charge of the NSP (zeta potential was +2 and −30 mV for not loaded and loaded NSP respectively).

Agarose coatings appeared to be uniform and smooth for all conditions considered. At the highest agarose concentrations (0.25 and 0.5%) hydrogel residues and particle aggregates appeared (see supplementary information). To assure stable uniform coating and good dispersion of the particles, 0.05 and 0.125 agarose concentrations (A1 and A2 respectively) were selected for further analysis, together with bare (not coated—NC) NSP for comparison.

Degradation process of NC NSP as observed at SEM is shown in FIGS. 36A-36H.

SEM images show the progressive degradation of NSP (into orthosilicic acid as assessed by ICP, data not shown (35, 42, 43)) during degradation while their size slightly decreased. Degradation rate of exposed silicon was uniform across the entire particle. As previously reported, we observed higher degradation in the outer rim because of the higher surface area and porosity of this structure (42).

NSP degradation over time was also monitored with flow cytometry (FACS) (FIGS. 37A-37N) quantifying NPS size variation through the change in the forward scattering intensity. Polystyrene beads of given size were used as calibration standards. FACS data showed that NPS size reduced in three days from about 3 to almost 2 μm (FIGS. 37A, 37D, 37H, and 37K) as was observed also at the SEM. FACS analysis reveals no significant differences between NC and Ag NSP with either agarose concentrations (A1 and A2) (FIGS. 37A-37N and FIGS. 37O-37P).

Quantification of Protein Release

To assess protein release from Ag NSP, fluorescent BSA was used as model. Loading and release of BSA from Ag NSP with two agarose concentrations (A1 and A2) and NC NSP were quantified by fluorescence spectroscopy. Loading efficiency was about 70% for both NC and Ag NSP (FIG. 38A); hence the agarose coating did not affect protein loading. FACS and spectrometric BSA release data are shown in FIGS. 38B and 38C respectively.

FACS results (FIG. 38B) showed that NSP fluorescence exponentially decreased ($y=A*e^{-B*x}$-$R^2$>0.91) in three days. Moreover there was no significant difference between NSP NC and Ag with both agarose concentrations. Spectrofluorimetry data (FIG. 38C) also showed that all the loaded protein was released with a logarithmic profile ($y=A*\ln(x)+B$-$R^2$>0.98) within three days for NSP NC and Ag with both agarose concentrations. FACS and spectrofluorimetry data agreed showing that while the BSA was released from NSP the particles' fluorescence decreased accordingly (see supplementary information for fitting curves and parameters); after 3 days almost all BSA was released (~90%) and NSP were almost not fluorescent anymore (~5%). Protein release study results indicated that agarose coating does not affect protein release from NSP.

Released Protein Integrity Analysis

Figure 39A:
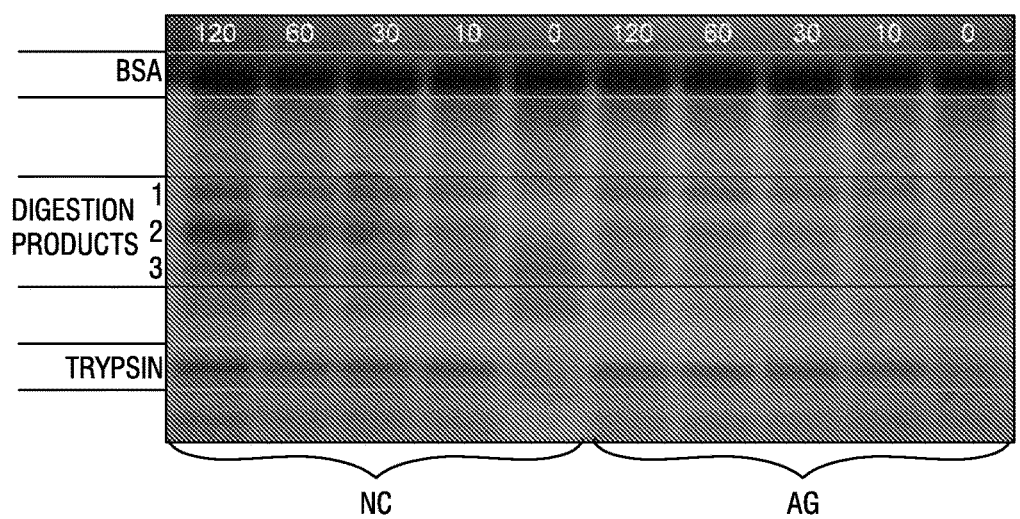

To assess the protection of protein integrity provided by agarose coating, BSA loaded NSP were treated with trypsin for 10, 30, 60 and 120 minutes, and released BSA solution analyzed with SDS page. Resulting gel for NC and Ag (composition A2) NSP is shown in FIG. 39A.

The gel analysis showed several protein fragments, digestion products, together with BSA and trypsin (when added), and no aggregates (see supplementary information). The concentration and number of fragments appeared higher in the solutions released from the NC NSP. Moreover the presence of protein fragments increased with trypsin treatment time while trypsin and BSA amounts were about the same in all the samples.

Figure 39B:
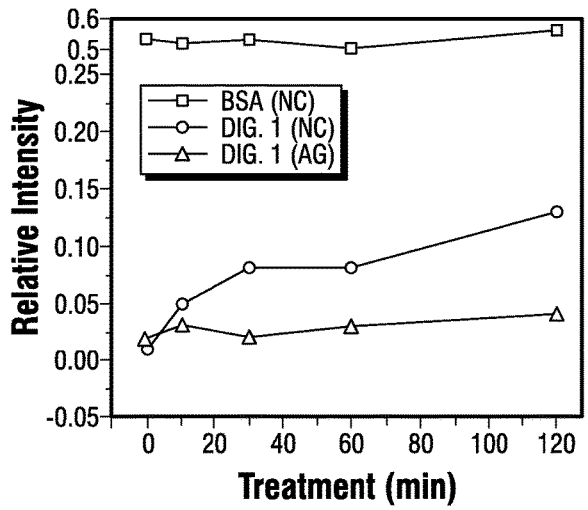
Figure 39C:
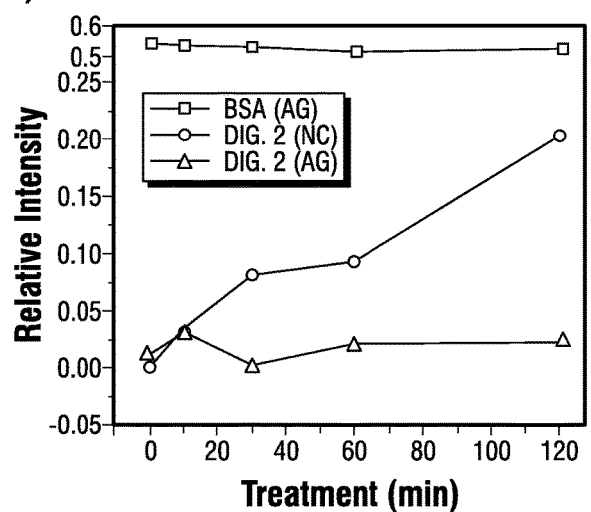
Figure 39D:
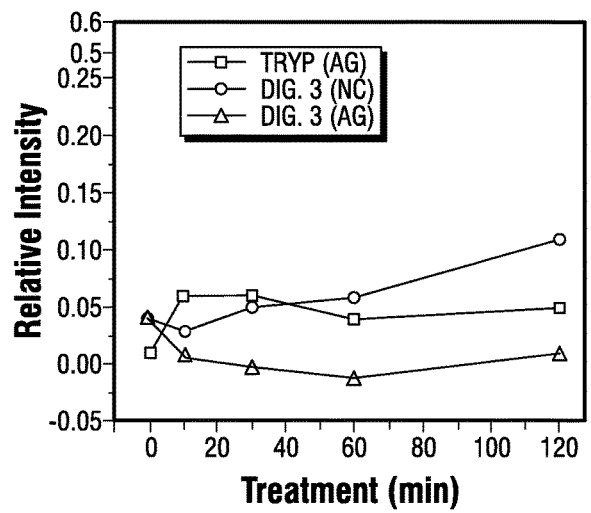

To better quantify protein, enzyme, and digestion products the SDS result was also analyzed with ImageJ and the three most abundant digestion products plotted as function of trypsin treatment duration (FIGS. 39B-39D). The quantitative analysis showed that solution recovered from NC NSP samples contained a higher concentration of digestion products than the one recovered from Ag NSP for all treatment conditions. The samples not treated with trypsin showed no difference between NC and Ag NSP. The amount of BSA and trypsin was the same in all treated samples. The amount of fragments increased with trypsin treatment time for the NC NSP samples but was almost constant in the Ag NSP ones.

HPLC analysis performed on BSA solution recovered after 24 hours from NSP not treated and treated with trypsin for 15 minutes, 2 hours, 4 hours, 8 hours and 18 hours is shown in FIGS. 40A-40B.

Graphs show an increase of digestion products concentration and number with duration of trypsin treatment. There were more digestion products in the solution released by NC particles especially for longer trypsin treatment time, as evidenced especially for the three species pointed by the arrows. These results are in agreement with the SDS-page analysis and confirm the protective function of the agarose coating from enzymatic digestion.

Cellular Internalization of NSP and Uptake of Protein

Cellular uptake of protein was studied using fluorescent BSA and evaluating the fluorescence within HUVEC by confocal microscope imaging after 24 and 48 hours. Particles internalization and BSA uptake after 48 hours of incubation with NC and Ag (composition A2) NSP added into the media with the cells or in a transwell on top of them is shown in FIGS. 41A-41F.

After 48 hours of incubation with cells, both NC and Ag NSP were completely internalized and BSA was released within the cells. Confocal microscopy showed that the internalization process was not affected by the agarose coating and NSP accumulated in the lysosomes in less than 1 hour, as previously reported (44).

NSP internalization was inhibited using the transwells and BSA was first released in the media and then incorporated into the cells. Images show that uptake of BSA released from NSP in the transwell or from BSA solution was not uniform within the cells and the protein probably accumulated within the lysosomes. The fluorescence within the cells receiving BSA from the transwell was comparable with that of the cells that internalized NSP. The cellular uptake of BSA from protein dispersed in solution (1 mg/mL) appears higher than the one achieved by NSP release (to avoid pixel oversaturation, different confocal settings were used to acquire FIG. 41F).

This can be attributed to less BSA being released from NPS resulting in a lower overall BSA concentration in the media. A difference in the cellular uptake of BSA between internalized Ag and not coated particles was observed. We hypothesized that the agarose coating was able to induce a change of pH within the lysosomes and influence the cellular uptake. To assess if the agarose coating matrix would affect the pH within the lysosomes, different volumes of pH 5 solution and agarose coating solution were mixed at room temperature and the change of pH was measured (FIG. 42).

As shown in FIG. 42, pH increased from 5 to 6 or more, depending on the ratio of agarose coating solution (AG), while no change of pH was observed if agarose was prepared with DI water instead of PBS. This experiment revealed that the agarose solution used to coat the particles had a buffering capacity which could have been instrumental for the local modification of the pH in the small acidic lysosomal environments.

The progression over time of the uptake process relative to HUVEC incubated with NC and Ag NSP is shown in FIGS. 43A-43D. After 24 hours of NSP incubation, cellular uptake of BSA was visible but still not evident especially for NC NSP. BSA accumulated in the cells where the NSP, both NC and Ag particles, were internalized. The protein, escaping from the lysosomes, was uniformly distributed throughout the nuclei and the cytoplasm of the cells. We hypothesize that the agarose coating affected lysosome pH once NSP were internalized and hence facilitated protein escape.

To better quantify the BSA uptake within the cells, the average green fluorescence intensity of confocal images within the cytoplasm and the nucleus of the cells was quantified with Elements (Nikon) and correlated with the number of NSP internalized in each cell (FIGS. 43E-43F). Data showed a higher uptake of BSA within cells incubated with Ag NSP than with NC NSP. Uptake of the protein was also proportional to the number of particles internalized. Uptake of BSA released from Ag NSP increased more rapidly with the number of internalized NSP than from NC NSP. Additionally protein accumulated within the nuclei more than within cytoplasm.

These data suggested that agarose coating increases cellular uptake of the protein and avoids extended entrapment in the lysosomes.

Conclusion

In this work we successfully modified with hydrogel NSP, designed and fabricated for drug delivery application, to improve their efficacy for intracellular protein release. We verified that the agarose coating protects the payload from enzymatic digestion while it does not affect its release from the NSP. We also showed that the hydrogel coating increases cellular uptake and influences intracellular trafficking of the protein in comparison with what was observed from proteins dispersed in solution. Furthermore the agarose coating is able to improve intracellular protein delivery and increases the accumulation of the protein within the nuclei. Thus the agarose coating of NSP may extend the use of pSi as versatile delivery system for enzymes, vaccine antigens, gene therapy and other protein therapeutics. Additionally it may act effectively in combination with other controlled release systems (e.g. PLGA encapsulation) to preserve protein stability during controlled drug delivery formulation and long term release.

Notations

FGF=fibroblast growth factor, VEGF=vascular endothelial growth factor, BSA=bovine serum albumin, PLGA=poly (lactic-co-glycolic acid), NSP=nanoporous silicon particles, NC=bare-not coated, Ag=agarose coated, A1=agarose composition 0.125%, A2=agarose composition 0.05%, APTES=aminopropyltriethoxysilane, pSi=porous silicon, SiN=low stress silicon nitride, SEM=scanning electron microscope, FACS=fluorescence activated cell sorting, SDS-page=sodium dodecyl sulfate polyacrylamide gel electrophoresis, HPLC=high performance liquid chromatography, HUVEC=human umbilical vein endothelial cells.

REFERENCES

1. B. Leader, Q. J. Baca, and D. E. Golan. Protein therapeutics: a summary and pharmacological classification. Nat Rev Drug Discov. 7:21-39 (2008).
2. W. J. Murphyand D. L. Longo. Growth hormone as an immunomodulating therapeutic agent. Immunology Today. 21:211-213 (2000).
3. D. J. Chen, N. Osterrieder, S. M. Metzger, E. Buckles, A. M. Doody, M. P. DeLisa, and D. Putnam. Delivery of foreign antigens by engineered outer membrane vesicle vaccines. Proceedings of the National Academy of Sciences. 107:3099-3104.
4. J. L. Rosado, N. W. Solomons, R. Lisker, and H. Bourges. Enzyme replacement therapy for primary adult lactase deficiency. Effective reduction of lactose malabsorption and milk intolerance by direct addition of [beta]-galactosidase to milk at mealtime. Gastroenterology. 87:1072-1082 (1984).
5. M. Haase. Human recombinant factor IX: safety and efficacy studies in hemophilia B patients previously treated with plasma-derived factor IX concentrates. Blood. 100:4242 (2002).
6. P. J. Mease. Etanercept in the treatment of psoriatic arthritis and psoriasis: a randomised trial. Lancet. 356:385-390 (2000).
7. J. D. Gorman, K. E. Sack, and J. C. Davis. Treatment of ankylosing spondylitis by inhibition of tumor necrosis factor [alpha]. N Engl J Med. 346:1349-1356 (2002).
8. W. Szmuness. Hepatitis B vaccine: demonstration of efficacy in a controlled clinical trial in a high-risk population in the United States. N Engl J Med. 303:833-841 (1980).
9. L. Shi. Gardasil: prophylactic human papillomavirus vaccine development [mdash] from bench top to bed-side. Clin Pharm Ther. 81:259-264 (2007).
10. D. B. Sodee. Multicenter ProstaScint imaging findings in 2154 patients with prostate cancer. Urology. 56:988-993 (2000).
11. R. Taillefer, S. Edell, G. Innes, and J. Lister-James. Acute thromboscintigraphy with Tc-99m-apcitide: results of the phase 3 multicenter clinical trial comparing Tc-99m-apcitide scintigraphy with contrast venography for imaging acute DVT. J Nucl Med. 41:1214-1223 (2000).
12. C. A. Meier. Diagnostic use of recombinant human thyrotropin in patients with thyroid carcinoma (phase I/II study). J Clin Endocrinol Metab. 78:188-196 (1994).
13. A. Velgvalriand G. Marko-Varga. Clinical Protein Science and Bioanalytical Mass Spectrometry with an Emphasis on Lung Cancer. Chemical Reviews. 110:3278-3298 (2010).
14. D. McVey, M. M. Hamilton, C. Hsu, C. R. King, D. E. Brough, and L. L. Wei. Repeat Administration of Proteins to the Eye With a Single Intraocular Injection of an Adenovirus Vector. Mol Ther. 16:1444-1449 (2008).
15. I. Mahmoodand M. D. Green. Pharmacokinetic and pharmacodynamic considerations in the development of therapeutic proteins. Clin Pharmacokinet. 44:331-347 (2005).
16. S. D. Putneyand P. A. Burke. Improving protein therapeutics with sustained-release formulations. Nature Biotech. 16:153-157 (1998).
17. K. Fu, A. M. Klibanov, and R. Langer. Protein stability in controlled-release systems. Nat Biotech. 18:24-25 (2000).
18. P. Tayaliaand D. J. Mooney. Controlled Growth Factor Delivery for Tissue Engineering. Advanced Materials. 21:3269-3285 (2009).
19. E. R. Edelman, M. A. Nugent, and M. J. Karnovsky. Perivascular and intravenous administration of basic fibroblast growth factor: vascular and solid organ deposition. Proc Natl Acad Sci USA. 90:1513-1517 (1993).
20. D. F. Lazarous, M. Shou, M. Scheinowitz, E. Hodge, V. Thirumurti, A. N. Kitsiou, J. A. Stiber, A. D. Lobo, S. Hunsberger, E. Guetta, S. E. Epstein, and E. F. Unger. Comparative Effects of Basic Fibroblast Growth Factor and Vascular Endothelial Growth Factor on Coronary Collateral Development and the Arterial Response to Injury. Circulation. 94:1074-1082 (1996).
21. J. Wang, K. M. Chua, and C.-H. Wang. Stabilization and encapsulation of human immunoglobulin G into biodegradable microspheres. Journal of Colloid and Interface Science. 271:92-101 (2004).
22. M. van de Weert, W. E. Hennink, and W. Jiskoot. Protein Instability in Poly(Lactic-co-Glycolic Acid) Microparticles. Pharmaceutical Research. 17:1159-1167 (2000).
23. H. Sah. Protein Instability Toward Organic Solvent/Water Emulsification: Implications for Protein Microencapsulation Into Microspheres. PDA Journal of Pharmaceutical Science and Technology. 53:3-10 (1999).
24. J. L. Cleland, A. Mac, B. Boyd, J. Yang, E. T. Duenas, D. Yeung, D. Brooks, C. Hsu, H. Chu, V. Mukku, and A. J. S. Jones. The Stability of Recombinant Human Growth Hormone in Poly(lactic-co-glycolic acid) (PLGA) Microspheres. Pharmaceutical Research. 14:420-425 (1997).

25. L. T. Canham. Bioactive silicon structure fabrication through nanoetching techniques. Advanced Materials. 7: (1995).
26. N. H. Voelcker, Y.-L. Khung, S. P. Low, L. R. Clements, and K. A. Williams. *Porous Silicon Science and Technology Conference*, Valencia, 2010.
27. R. Herino. The Properties of Porous Silicon. In L. T. Canham (ed.), INSPEC-IEE, London, U K, 1997.
28. J. Salonen, A. M. Kaukonen, J. Hirvonen, and V. P. Lehto. Mesoporous silicon in drug delivery applications. Journal of Pharmaceutical Sciences. 97:632-653 (2008).
29. C. Chiappini, E. Tasciotti, J. R. Fakhoury, D. Fine, L. Pullan, Y.-C. Wang, L. Fu, X. Liu, and M. Ferrari. Tailored Porous Silicon Microparticles: Fabrication and Properties. ChemPhysChem. 11:1029-1035 (2010).
30. F. Cunin, T. A. Schmedake, J. R. Link, Y. Y. Li, J. Koh, S. N. Bhatia, and M. J. Sailor. Biomolecular screening with encoded porous-silicon photonic crystals. Nat Mater. 1:39-41 (2002).
31. J. Linsmeier, K. Wilst, H. Schenk, U. Hilpert, W. Ossau, J. Fricke, and R. Arens-Fischer. Chemical surface modification of porous silicon using tetraethoxysilane. Thin Solid Films. 297:26-30 (1997).
32. C. Gurtner, A. W. Wun, and M. J. Sailor. Surface Modification of Porous Silicon by Electrochemical Reduction of Organo Halides. Angewandte Chemie International Edition. 38:1966-1968 (1999).
33. J. Salonen, L. Laitinen, A. M. Kaukonen, J. Tuura, M. Björkqvist, T. Heikkilä, K. Vänd-Heikkilä, J. Hirvonen, and V. P. Lehto. Mesoporous silicon microparticles for oral drug delivery: Loading and release of five model drugs. Journal of Controlled Release. 108:362-374 (2005).
34. C. A. Prestidge, T. J. Barnes, C. H. Lau, C. Barnett, A. Loni, and L. Canham. Mesoporous silicon: a platform for the delivery of therapeutics. Expert Opin Drug Deliv. 4:101-110 (2007).
35. E. Tasciotti, X. W. Liu, R. Bhavane, K. Plant, A. D. Leonard, B. K. Price, M. M. C. Cheng, P. Decuzzi, J. M. Tour, F. Robertson, and M. Ferrari. Mesoporous silicon particles as a multistage delivery system for imaging and therapeutic applications. Nature Nanotechnology. 3:151-157 (2008).
36. C. A. Prestidge, T. J. Barnes, A. Mierczynska-Vasilev, I. Kempson, F. Peddie, and C. Barnett. Peptide and protein loading into porous silicon wafers. physica status solidi (a). 205:311-315 (2008).
37. C. A. Prestidge, T. J. Barnes, A. Mierczynska-Vasilev, W. Skinner, F. Peddie, and C. Barnett. Loading and release of a model protein from porous silicon powders. physica status solidi (a). 204:3361-3366 (2007).
38. R. E. Serda, B. Godin, E. Blanco, C. Chiappini, and M. Ferrari. Multi-stage delivery nano-particle systems for therapeutic applications. Biochimica et Biophysica Acta (BBA)—General Subjects. In Press, Corrected Proof:in press (2010).
39. M. Kilpelainen, J. Riikonen, M. A. Vlasova, A. Huotari, V. P. Lehto, J. Salonen, K. H. Herzig, and K. Järvinen. In vivo delivery of a peptide, ghrelin antagonist, with mesoporous silicon microparticles. Journal of Controlled Release. 137:166-170 (2009).
40. E. J. Anglin, M. P. Schwartz, V. P. Ng, L. A. Perelman, and M. J. Sailor. Engineering the Chemistry and Nanostructure of Porous Silicon Fabry-Perot Films for Loading and Release of a Steroid. Langmuir. 20:11264-11269 (2004).
41. M. Ferrari. Nanogeometry: Beyond drug delivery. Nat Nano. 3:131-132 (2008).
42. B. Godin, J. Gu, R. E. Serda, R. Bhavane, E. Tasciotti, C. Chiappini, X. Liu, T. Tanaka, P. Decuzzi, and M. Ferrari. Tailoring the degradation kinetics of mesoporous silicon structures through PEGylation. Journal of Biomedical Materials Research Part A. 94A:1236-1243 (2010).
43. R. E. Serda, A. Mack, M. Pulikkathara, A. M. Zaske, C. Chiappini, J. R. Fakhoury, D. Webb, B. Godin, J. L. Conyers, X. W. Liu, J. A. Bankson, and M. Ferrari. Cellular Association and Assembly of a Multistage Delivery System. Small. 6:1329-1340 (2010).
44. S. Ferrati, A. Mack, C. Chiappini, X. Liu, A. J. Bean, M. Ferrari, and R. E. Serda. Intracellular trafficking of silicon particles and logic-embedded vectors. Nanoscale. 2:1512-1520 (2010).

Example 8. Mesoporous Silicon-PLGA Composite Microspheres for the Double Controlled Release of Biomolecules for Orthopedic Tissue Engineering In this study, PLGA/pSi composite microspheres, synthesized by a solid-in-oil-in-water (S/O/W) emulsion method, are developed for the long-term controlled delivery of biomolecules for orthopedic tissue engineering applications. Confocal and fluorescent microscopy, together with material analysis show that each composite microsphere contained multiple pSi particles embedded in the PLGA matrix. The release profiles of FITC labeled-Bovine Serum Albumin (FITC-BSA), loaded in the pSi within the PLGA matrix, indicate that both PLGA and pSi contribute to control the release rate of the payload. Protein stability studies show that PLGA/pSi composite can protect BSA from degradation during the long term release. We find that during the degradation of the composite material, the presence of the pSi particles neutralizes the acidic pH due to the PLGA degradation by-products, thus minimizing the risk of inducing inflammatory responses in the exposed cells while stimulating the mineralization in osteogenic growth media. Confocal studies show that the cellular uptake of the composite microspheres is avoided, while the fluorescent payload is detectable intracellularly after 7 days of co-incubation. In conclusion, the PLGA/pSi composite microspheres could be ideal candidates as drug delivery vehicles for orthopedic tissue engineering applications.

Introduction

Porous silicon (pSi) has been widely used for tissue engineering and drug delivery in virtue of its biodegradable and biocompatabile nature.[1] As a scaffold, pSi is suitable for directing the growth of neuronal cells[2] and for stimulating mineralization in bone tissue engineering.[3, 4] For therapeutic delivery, pSi has been administered orally,[5] intravenously,[6] or been injected percutaneously and intraperitoneally in humans for brachytherapy without notable side effects.[7] A wide variety of therapeutic and imaging agents have been successfully loaded into and released from pSi particles including steroids,[8] hormones,[9] proteins,[10] cancer drugs,[11] iron oxide nanoparticles,[12] quantum dots, liposomes[13] and carbon nanotubes[14, 15] showing the great versatility of this material as a delivery system. Also, the size and shape as well as the porosity and pore size of the pSi particles can be engineered and tightly controlled during manufacturing in order to provide a material with constant and uniform physical features at the micro- and nano-scale and to control degradation time and kinetics as well as biodistribution and bioaccumulation.[16] Additionally, their surface can be functionalized to accomodate various drugs, control cellular uptake, target specific tissues[17] and alter their biodistribution in murine models,[13, 18] thus allowing for the accumulation of therapeutic agents at tumor sites,[19] or in reservoirs able to sustain the release of nanoliposomes carrying siRNA.[20]

Also PLGA, an FDA approved biodegradable polymer, has been widely investigated for drug delivery applications due to a number of advantageous features.[21, 22] First, its degradation rates can be tailored to obtain controlled delivery of drugs. Secondly, the material properties can be adjusted by changing the lactic acid and glycolic acid ratio or molecular weight. Thirdly, PLGA nanoparticles or microparticles can be formulated in order to load not only small molecules but also proteins and larger payloads.[23-25] However, some issues that remain unsolved include the achievement of a uniform, zero order, sustained, linear release and to prevent the initial burst release typical of most PLGA systems.[26] Additionally, the acidic PLGA degradation by-products decrease the pH of the surrounding environment, which may cause undesired inflammatory responses.[27] Finally, the available fabrication methods for PLGA microparticles are incompatible with water-soluble proteins as they may degrade or denature at the organic/inorganic interface during formulation processes.[28]

In this study we show that the addition of pSi particles to PLGA microspheres offers a solution to each one of the aforementioned issues. pSi particles due to their high surface area and to their interconnected pores allow for the storage and protection of large amounts of therapeutic molecules.[29] Additionally, PLGA coating provides a tunable layer to seal pSi pores, slow down pSi degradation, and control the release of the payload. Orthosilicic acid, the by-product of pSi degradation,[30] can neutralize the acidic pH of the PLGA degradation products thus creating less harsh and more cell friendly conditions in the microenvironment both in vitro and in vivo.[31] The use of hydrophilic pSi particles increased the hydrophilicity of the PLGA/pSi system and improved cell anchorage while not affecting cell proliferation. When the soluble proteins were efficiently loaded within the pores of the pSi particles, their structural integrity (biostability) was preserved. Furthermore, orthosilicic acid is involved in the collagen formation and facilitates the deposition of calcium and other minerals, thus stimulating bone formation in orthopedic tissue engineereering applications.[32,33]

pSi Particles

Quasi-hemispherical shaped pSi shells of 3.2 μm in diameter and 600 nm shell thickness (as shown in FIGS. 45A-45D) were fabricated according to established protocols.[14] Average Pore size was 20 nm with 51% porosity as determined from the desorption branch of nitrogen adsorption/desorption isotherms (data shown in supporting material). In order to turn the pSi surface from hydrophobic to hydrophilic, the pSi surface was modified with (3-Aminopropyl) triethoxysilane (APTES). Zeta potential analysis showed that the surface charge of the particles after APTES modification had a value of 6.44 mV, while the oxidized pSi surface had a surface charge of −30.39 mV. Once resuspended in IPA, the surface charge of the APTES modified particles showed no notable change for 2 weeks, thus indicating stable modification of the exposed silicon layer (data shown in FIGS. 56-58).

PLGA/pSi Microsphere Characterization

Figure 46A:
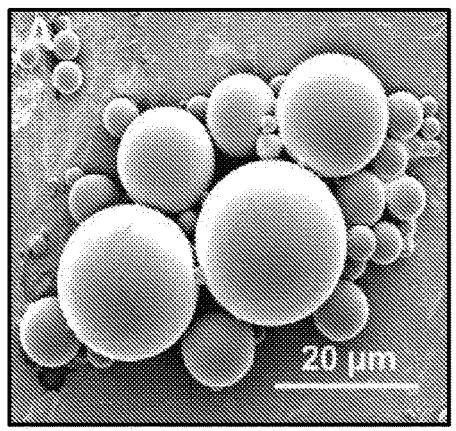
Figure 46B:
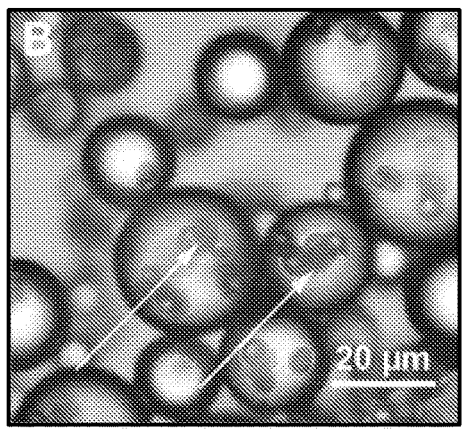
Figure 46C:
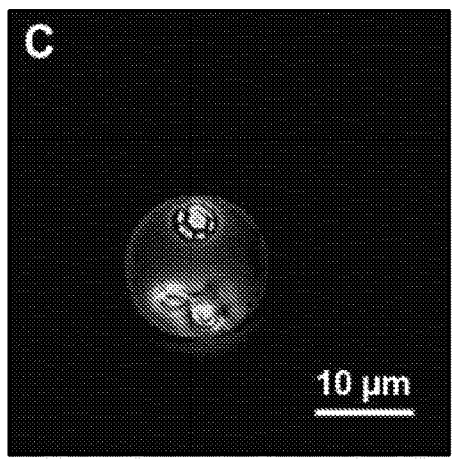
Figure 46D:
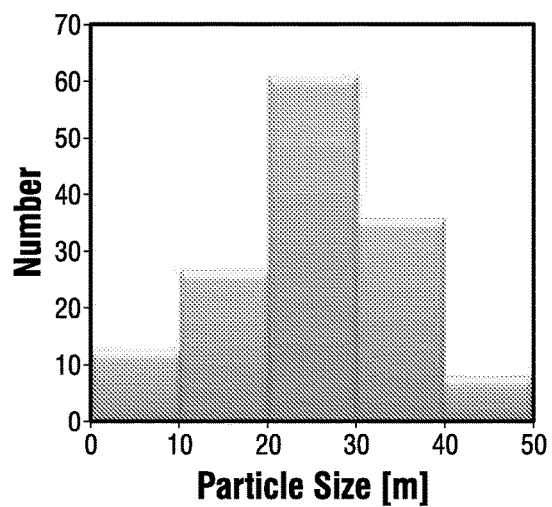

The overall aspect and the morphology of the microspheres were characterized by optical, confocal, and scanning electron microscopy. FIG. 46A shows the SEM images of FITC-BSA loaded microspheres. FIG. 46B shows the transmission microscopy image of the composite material that allows to appreciate the pSi particles (brown dots, see arrows) embedded in the transparent spherical PLGA particles. These images indicate that the pSi particles had been fully encapsulated in the PLGA spheres. Fluorescent microscopy image (FIG. 46C) shows the same results. FITC-BSA diffused from pSi particles into the PLGA layer. FIG. 46D shows the size distribution of the PLGA/pSi microspheres. The microspheres displayed a distribution of sizes ranging from a few microns to approximately 35 μm with an average diameter of 24.5±9.54 μm (145 microspheres were measured).

PLGA/pSi Microsphere Sorting

PLGA/pSi microspheres prepared with 488-DyLight conjugated pSi particles were characterized before and after centrifugation sorting by fluorescence activated cell sorting (FACS) and confocal microscopy (FIGS. 47A-47E). FACS data (FIGS. 47A-47B) show that the mean fluorescence and hence the percentage of coated particles increases of about one order of magnitude after centrifugation sorting. The coated-fluorescent fraction was initially only the 10% of the sample and after the centrifugation process, it increased to 80%. Moreover the negligible fluorescence of the supernatant reveals the absence of coated particles in it. Its mean fluorescence is two order of magnitude lower than the original sample and only 1% of it has a comparable fluorescence (FIGS. 47A-47B). FIG. 47C shows the fluorescence intensity and distribution of 488-DyLight conjugated pSi particles (light green), nonsorted microspheres (blue), sorted microspheres (dark green), and supernatant solution (black).

Confocal images show a mix of fluorescent and not fluorescent microspheres with polydistributed sizes in the not sorted sample (FIG. 47D) and a more uniform particles size after the sorting procedure (FIG. 47E) confirming that the sequential centrifugation procedure achieved a good separation of PLGA/pSi microspheres from smaller empty PLGA microspheres.

Evaluation of FITC-BSA Loading

The mechanism of loading and retention of the molecules inside the pores of the pSi particles is based on the electrostatic interactions between the amino groups on the surface of the APTES modified pSi particles and the carboxylic portion of the amide groups in the protein. The loading efficiency of FITC-BSA into pSi particles varied between 9.77% to 86%, depending on the concentrations of the loading solutions (data shown in supporting material). During the microemulsion step, the loss of the FITC-BSA was approximately 13.24%, 9.84%, and 5.14% from the composites and it inversely correlated with the density of the different PLGA coatings (6%, 10%, and 20% respectively). This result demonstrated that during synthesis higher concentrations of the coating solutions resulted in lower protein loss.

In Vitro Release of FITC-BSA

Figure 48A:
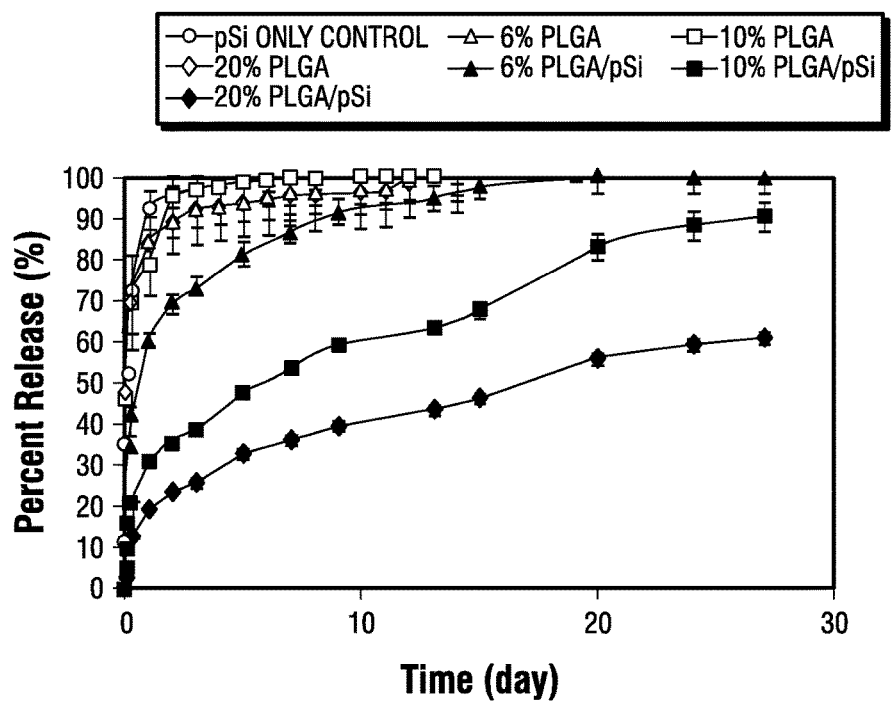
Figure 48B:
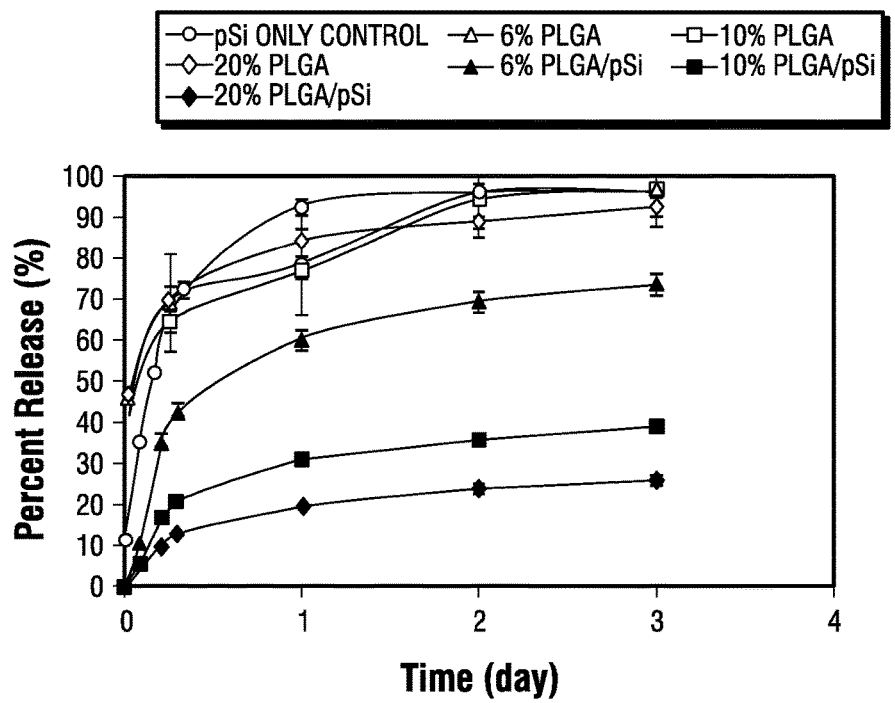

The release profiles of FITC-BSA from pSi particles (control), PLGA microspheres (control) and PLGA/pSi microspheres are shown in FIG. 48A. In the case of pSi particles and PLGA microspheres (6%, 10%, and 20%), protein release showed a massive initial burst release which reached the plateau after less than 3 days. On the contrary, PLGA/pSi microspheres released approximately 70% (6% PLGA), 38% (10% PLGA), and 25% (20% PLGA) of the payload at day 3 (FIG. 48B). After 2 weeks, the release of FITC-BSA from the composite reached approximately 100% (6% PLGA/pSi), 60% (10% PLGA/pSi), and 40%

Figure 48C:
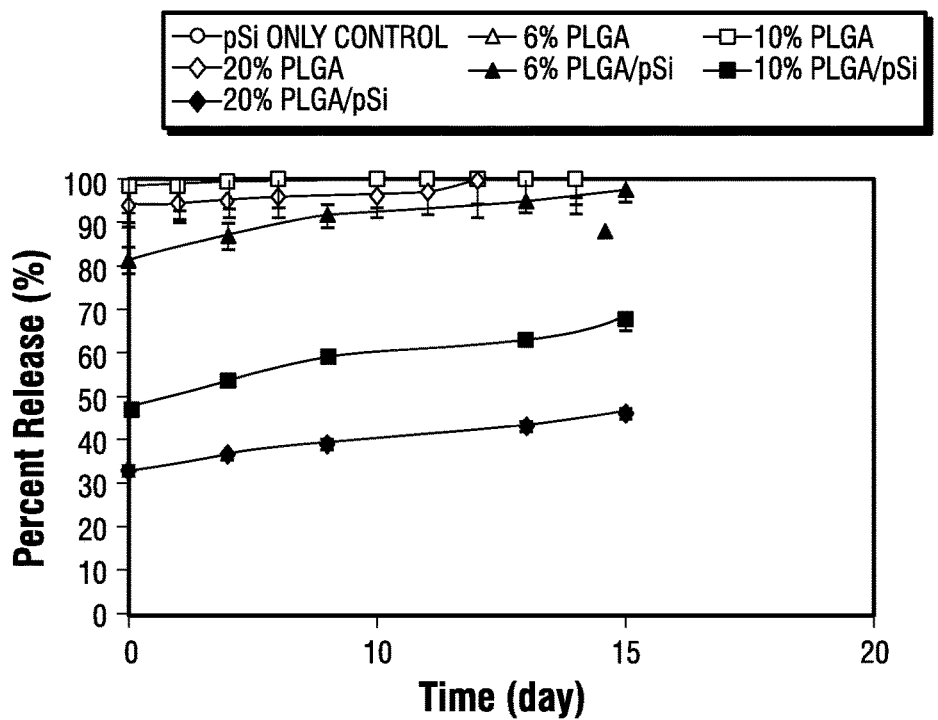
Figure 48D:
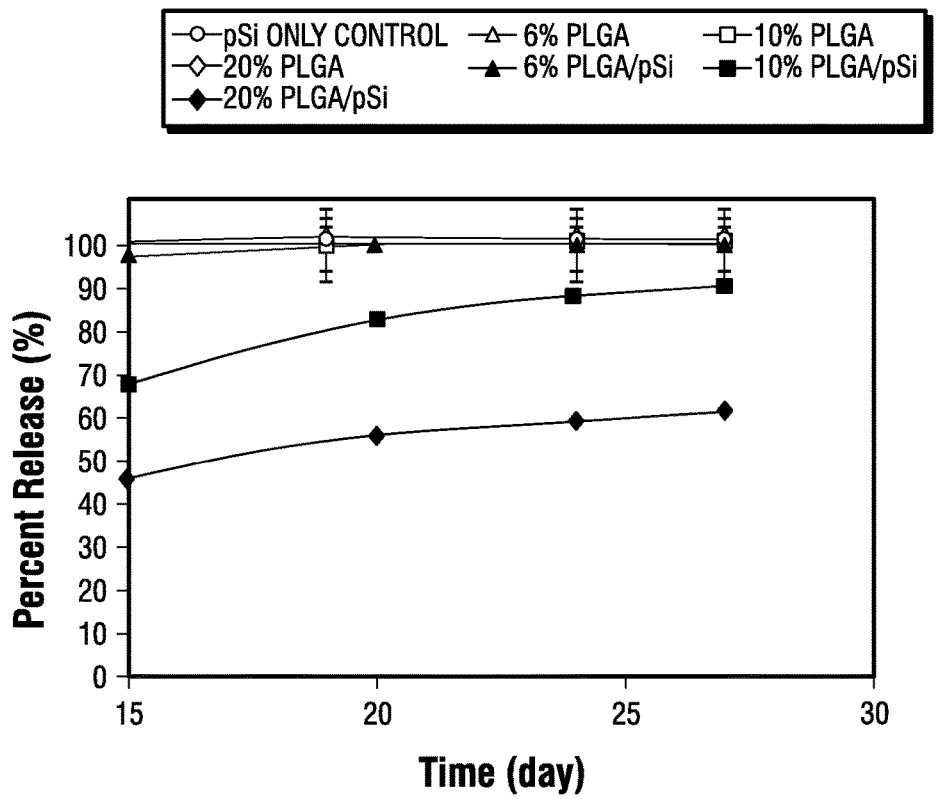

(20% PLGA/pSi) of the payload as shown in FIG. 48C and it continued to be released for other 2 weeks from the higher density PLGA coatings (10% and 20%) (FIG. 48D). FIGS. 49A and 49B show that at all time points, PLGA/pSi microparticles showed consistently higher fluorescence when compared to controls. Due to the initial burst release of FITC-BSA during the first 3 days, the fluorescence of PLGA microspheres decreased at fast pace and dropped to its minimum. Conversely, the addition of pSi particles to the PLGA microspheres reduced the FITC-BSA release rate as demonstrated by the higher fluorescence intensity measured throughout the experiment.

All together, the study of the in vitro release of FITC-BSA demonstrated that the PLGA coating played an important role in controlling the release kinetics from the microspheres. A higher concentration of PLGA resulted in a coating layer characterized by higher density and thickness. As a consequence, the diffusion of FITC-BSA through the PLGA layers was slowed down, resulting in lower release rates and more sustained delivery of the payload. Similarly, a thicker layer of PLGA delayed the degradation of the composite microspheres thus additionally slowing down the release of the encapsulated proteins. In all profiles, the two phases observed during protein release were attributed to a minor fraction of the pSi loaded BSA which diffused into the PLGA layer during the microsphere fabrication process and was released earlier than the fraction still loaded into the pores of pSi particles.

PLGA/pSi Microsphere Degradation

The PLGA/pSi microsphere degradation was studied by monitoring the mophology changes using SEM. FIGS. 50A-50H and FIGS. 50J-50P show the SEM images of three types of PLGA/pSi microspheres (6%, 10%, and 20% PLGA coatings) degradation over 6 weeks in PBS. At week 1, pores were observed on the surface of all three types of microspheres, showing an early-stage degradation. Pore number and size increased with time and after 3 weeks, 6% and 10% PLGA/pSi microspheres appeared deformed and partially collapsed. At week 4, more pores appeared on the surface of the 6% PLGA/pSi microspheres, while the surface layers of polymer coatings were peeled off from the 10% and 20% PLGA/pSi mircospheres and a porous, sponge-like morphology was observed beneath the surface. At week 6, the 6% PLGA/pSi microspheres completely lost their spherical morphology, while the 10% and 20% PLGA/pSi broke into pieces revealing the inner porous structure of the microsphere.

FIGS. 51A-51B demonstrate the change of pH in the medium during the degradation of PLGA, pSi, and PLGA/pSi microspheres. The control sample (pSi) kept a constant pH value of approximately 7.2 during the 4-week degradation. PLGA microsphere degradation induced a pH drop at two weeks (FIG. 51A). However, when pSi microparticles were introduced to the PLGA microspheres, the pH values recorded were approximately around 7 over the four-week degradation period, and only the microspheres with the thickest coating (20% PLGA) generated acidic conditions after four weeks (FIG. 51B). This is due to the fact that the pSi degradation product, silicic acid buffered the pH at higher values.[34, 35] The mass ratio of PLGA to pSi is 5:1 (6% PLGA/pSi), 8:1 (10% PLGA/pSi), and 16:1 (20% PLGA/pSi). The PLGA and pSi particles degrade concurrently, which allows silicic acid to buffer the acidic environment when the acidic products of PLGA are produced. As expected, lower ratios showed higher buffer capacity than the higher ratio.

BSA Stability Studies

BSA, like all other proteins, is susceptible to hydrolytic degradation in aqueous solutions. These reactions can be catalyzed by acidic molecules, such as the byproducts of PLGA. In order to minimize protein degradation during loading, FITC-BSA was first loaded into pSi microparticles and lyophilized prior to PLGA coating. This step reduces exposure to water during particle preparation and during eventual PLGA degradation. SDS-PAGE of released FITC-BSA and degraded byproducts is exhibited in FIG. 52. The appearance of bands for degraded proteins is substantially less for PLGA/pSi-released BSA than controls at 7 days. Between 9 and 14 days, a relatively small amount FITC-BSA is released which is insignificant compared to controls and 7 day time points. However, 10% and 20% coating groups show only an intact FITC-BSA band and not small byproducts, indicating that molecules released after one week have not been hydrolytically degraded. This is likely because molecules stored deep within the core of the microparticles are not exposed to any water until the PLGA coating has been sufficiently eroded.

In Vitro Mineralization Studies

Figure 53A:
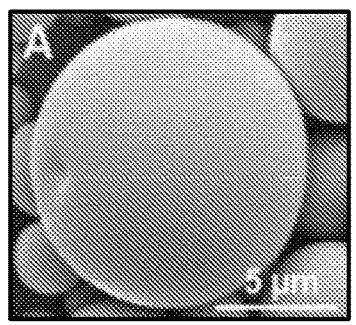
Figure 53B:
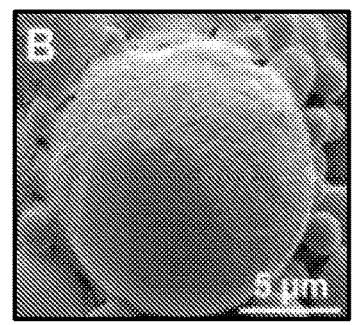
Figure 53C:
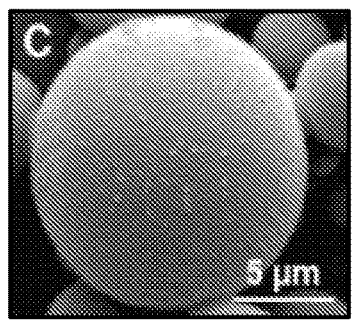
Figure 53D:
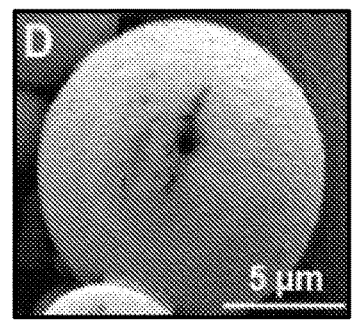
Figure 53E:
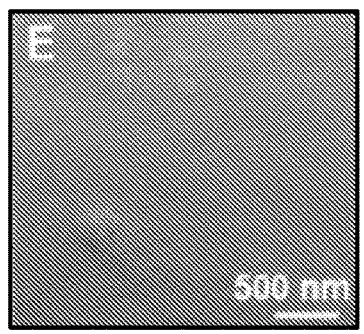
Figure 53F:
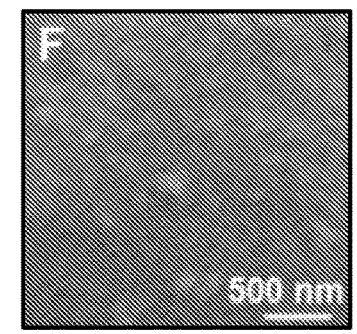
Figure 53G:
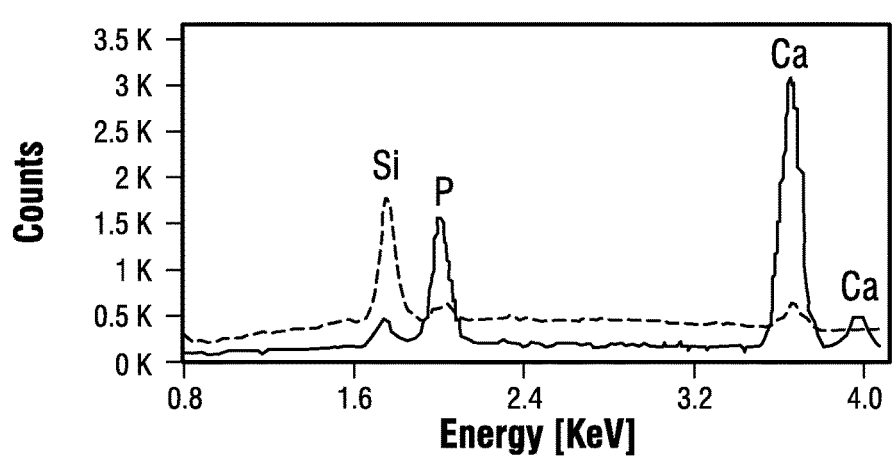

PLGA microspheres do not calcify in the absence of bioactive materials which stimulate deposition of calcium phosphate (CaP) bone mineral. This study has investigated if the addition of pSi microparticles to PLGA microspheres can render these inert microspheres bioactive. After incubation in the osteogenic media for 3 days, the smooth surface of the PLGA/pSi microspheres was covered with a porous rough layer (FIGS. 53A-53G), while the control PLGA microspheres remained smooth with just minimal crystal deposition on the surface (FIG. 53A). After 21-day incubation, SEM images showed that the surface of PLGA/pSi microspheres was uniformly covered with a layer of mineral deposites (FIG. 53D) while the control samples showed negligible signs of calcification under the same conditions at the same time intervals (FIG. 53C). This phenomenon was confirmed at higher magnification at SEM (FIG. 53E-53F). These data suggested that the pSi contained in the PLGA microspheres has the ability to stimulate the formation of a mineralized layer on the surface. As a confirmation of the formation of the calcium phosphate crystals on the surface of the microspheres, in the EDX spectrum showed calcium and phosphorous peaks on the surface layer at day 3 (grey dot line) and day 8 (black solid line) (FIG. 53G). The mechanism of calcium phosphate deposition is that the polymerized silicic acid acted as heterogeneous nucleation substrate to stabilize the growing of calcium phosphate nuclei. The uniformly coated osteoactive mineral layer will further enhance the osteogenic qualities and the osteoconductive potential of the scaffolds, while still allowing the release of the bioactive molecules due to the inherent porosity of the surface mineralization (see FIG. 9)[33]

PLGA/pSi Microsphere Internalization by BMSCs

Most growth factors and differentiating stimuli function by binding to cell surface receptors to start active transmembrane signal transduction while the ligand is still in the extracellular space. When growth factors or differentiation stimuli are vehicled by a nanosized carrier and the carrier is internalized by the target cells, they fail to interact with the membrane receptors and hence, completely lose their function and bioactivity.[36] The intended function of our composite particles is to release bioactive proteins at the site of tissue repair. In these scenarios, macrophages and other inflammatory cells often internalize and degrade nano-size particles through endocytosis, pinocytosis and phagocytosis.[37, 38] In this study, BSA was used as a moel growth factor to be delivered by PLGA/pSi microspheres. The PLGA coating around pSi particles prevents internalization due to its size, while providing a hydrophobic barrier to enzymes released by the cells thus protecting for longer times their bioactive payloads. One of the purposes of this study was to determine if the PLGA/pSi microspheres could serve as potential vehicles to successfully deliver growth factors. Confocal microscopy images showed that the 10% PLGA/pSi microspheres (average diameter 24.5 µm) were not internalized by the cells after 0.5 h (FIGS. 54D and 54G), 48 h (FIGS. 54E and 54H) and 120 h incubation (FIGS. 54F and 54I). The control images showed accumulation of the uncoated pSi (~3 micron) inside the bone marrow stromal cells within an hour from the beginning of the incubation (FIG. 54A, 30 min incubation) and after 48 h (FIG. 54B) and 120 h incubation (FIG. 54C). No cell death, morphological changes or overall cytotoxicity to BMSCs was observed in vitro during the entire cell culture period, confirming the compatibility of these composite microspheres to cells and surrounding environment. FIG. 54J shows a cartoon describing the mechanism of action of the pSi particles (right side of the dashed line) versus the PLGA/pSi composite microspheres (left side of the dashed line). While pSi are internalized by BMSCs (FIG. 54J), the PLGA/pSi particles lay on the surface of the BMSCs avoiding cellular uptake (FIG. 54J).

Furthermore, the internalization of the pSi inside the cell would inevitably result in its entrapment into the lysosomal compartment as shown in FIG. 54J. The acidic environment of lysosomes would denature the growth factors, affect their bioactivity and natural site of action thus resulting in the complete absence of a response to the treatment (FIG. 54J).[39,40] On the contrary, the ability of the PLGA/pSi microspheres to escape internalization results in the double advantage of preventing the exposure of the payload to the hostile lysosomal environment while releasing it in close contact to the external layer of the cellular membrane where most of protein mediated signaling starts. As a consequence of membrane receptor triggering, the signal pathway arrives to the nucleus thus allowing for a change in cell functions (color change in FIG. 54J).

Cellular Uptake of FITC-BSA Released from PLGA/pSi Microspheres

BSA, like many growth factors, is internalized through receptor-mediated endocytosis (clathrin-mediated endocytosis) and fluid phase endocytosis,[41-46] and was selected as a model protein for the release and cellular uptake studies. As mentioned previously, BSA released from PLGA/pSi microspheres first activated cell surface receptors to start signal transduction to alter intracellular response and then BSA was internalized by the cells (FIG. 54J). To assess the rate of cellular uptake of the BSA released from the PLGA/pSi microspheres, human umbilical vein endothelial cells (HUVEC) were studied using confocal microscopy after 7 days in culture. HUVEC cells were plated in a transwell without microspheres and incubated with PLGA/pSi in the top chamber (FIGS. 55A-55E). Confocal images show an evident cellular uptake of BSA after 7 days of incubation with PLGA/pSi microspheres. Cellular uptake appeared in discrete spots that probably suggesting protein accumulation in subcellular organelles. The control group (BSA in solution) did not show any BSA accommulation in cells. Fluorescence quantification of the confocal images showed 35 fold increase of the corresponding green fluorescence, while no difference was recorded in the red and blue fluorescence associated to the cytoscheleton (actin) and nucleus (blue) respectively. These results suggest that PLGA/pSi microspheres can be used as tunable carriers for releasing bioactive proteins to cells in a controlled and predictable fashion.

Conclusions

A novel class of PLGA/pSi microspheres was fabricated by an S/O/W emulsion method by incorporating polymer science with micro-litography and electrochemical etching. This system provides a number of unique advantages over pre-existing drug delivery materials thanks to its ability to: 1) prevent the burst release of proteins and prolong the delivery rate over a longer period of time through the tuning of the PLGA coating; 2) counteract the acidification of the environment by PLGA degradation byproducts via buffering with degradation products of the pSi particles; 3) preserve protein stability and half-life as the S/O/W method prevents protein degradation during the fabrication process; 4) control cellular internalization and protein accumulation by increasing the particle diameter with PLGA coatings and controlling biomolecular release based on PLGA properties, respectively. PLGA/pSi microspheres can not be internalized by cells due to their size, which is particularly important for the delivery of growth factors and proteins interacting with extracellular receptors. 5) stimulate mineralization by promoting the deposition of calcium phosphate ions on the particle surface. All together, these findings demonstrate that the PLGA/pSi microspheres show superior properties than traditional PLGA microspheres and represent a promising alternative as drug delivery vehicles for tissue engineering applications. Their use has been already successfully tested in different orthopedic tissue engineering applications in small and large animal models of bone fracture repair (manuscript in preparation).

EXPERIMENTAL pSi Particle Fabrication:

The pSi particles were fabricated as previously described.[29] Briefly, an layer of silicon nitride ($Si_3N_4$) (80 nm) was deposited by low pressure chemical vapor deposition on a 4" p-type Si wafer with resistivity <0.005. AZ5209 photoresist (AZ Electronic materials) was spun cast at 5000 R.P.M. for 30 s on the substrate, followed by pre-exposure baking at 90° C. in an oven for 10 min. A pattern consisting of dark field circles (2 µm) with pitch (2 µm) was transferred on the photoresist with a MA/MB6 mask aligner. The pattern was developed for 20 s in MIF 726 developer, and then transferred into the silicon nitride ($Si_3N_4$) layer and 300 nm into the silicon substrate by two step Reactive Ion Etch (first step: Plasmatherm 790, 25 sccm $CF_4$, 200 mTorr, 250 W RF, 2 min 20; second step: Oxford Plasmalab 80, 20 sccm $SF_6$, 100 mTorr, 200 W RF, 4 min). The photoresis was removed from the substrate by an 8 min piranha clean ($H_2O_2$:$H_2SO_4$ 1:2 v/v). The porous particles were formed by anodic etch in Hydrofluoric acid (HF): ethanol (1:3 v/v) applying a current (0.3 A) for 60 s followed by 3.8 A for 6 s in a custom Teflon etching cell. The $Si_3N_4$ layer was removed by soaking in HF for 30 min, the substrate was dried and the particles were released in isopropanol (IPA) (Acros) by sonication.

Z2 Analysis and Surface Modification of pSi:

For oxidation, the dried pSi particles were resuspended in a piranha solution and heated to 110-120° C. for 2 h. The suspension was washed with DI water until the pH was approximately 5.5-6.0. Oxidized pSi particles were suspended in ISOTON® II Diluent, and counted by a Multisizer 4 Coulter® Particle Counter (Beckman Coulter) with an aperture (20 µm). PSi particles were surface modified with APTES (Sigma Aldrich) as reported previously. [16] $1 \times 10^8$ oxidized particles were suspended in of Millipore water (20

μl). A solution was prepared of 2.0% APTES and 3.0% Millipore water in IPA. This solution (980 μl) was added to the particles and mixed well. This vial was placed to a 35° C. thermomixer set to mix at 1300 rpm for 2 h. After modification, the particles were washed with anhydrous IPA 5 times and moved to a vacuum oven for annealing at 60° C. overnight.

Loading of FITC-BSA into APTES Modified pSi Particles:

FITC-BSA (Sigma Aldrich) solution (10 mg/ml) was prepared by dissolving FITC-BSA powder in distilled water. $4 \times 10^8$ APTES modified particles were immersed into of FITC-BSA solution (200 μl) in an eppendorf tube. The suspension was incubated on a thermal mixer at 37° C. under agitation for 30 min to allow the adsorption of the protein into the pores of pSi particles. The particles were separated by centrifugation and washed with PBS to remove the FITC-BSA physically absorbed on the surface. The FITC-BSA loaded particles were then lyophilized overnight. The amount of protein absorbed was measured by the difference between the protein concentrations of the stock solution and of the supernatant using SpectraMax M2 spectrophotometer (Molecular Devices).

Preparation of PLGA Particles and PLGA Coated pSi Particles:

pSi particles coated with PLGA were prepared by a modified S/O/W emulsion method [47] as shown in FIGS. 44A-44D. Briefly, PLGA (50:50) (Sigma Chemicals Co. St. Louis, Mo.) was dissolved in dicholoromethane (DCM) (Sigma Aldrich) to form 6%, 10%, and 20% w/v PLGA/DCM solution respectively. $8 \times 10^7$ FITC-BSA loaded particles were suspended in these solutions (1 ml, 6%, 10%, and 20%) respectively by sonicating the mixture. The organic phase containing the pSi was mixed with of Poly (vinyl alcohol) (PVA) (Fisher Scientific) (3 ml, 2.5% w/v) by vortex mixing and sonication. The mixture was gradually dropped into water (50 ml) containing PVA (0.5% w/v). The resulting suspension was stirred with a magnetic stir bar for 2 h and the DCM was rapidly eliminated by evaporation. The PLGA/pSi microspheres were washed with distilled water. Finally, the product was lyophilized and stored at 4° C. PLGA particles were prepared in the similar method as PLGA/pSi microsphere fabrication, except that BSA solution instead of BSA loaded pSi particles was mixed with PLGA/DCM.

Characterization of PLGA/pSi Microspheres:

The morphology of the microspheres was characterized by optical microscope (Nikon Eclipse TS 100), fluorescent microscope (Nikon Eclipse TE 2000-E), confocal laser microscope (Leica MD 6000), and scanning electron microscope (SEM) (FEI Quanta 400 ESEM FEG). The samples were analyzed by confocal laser microscope at 488 nm to identify the FITC-BSA loaded pSi. The microspheres were also examined by SEM under a voltage of 3 KV. The samples were sputtered with gold (20 nm) by a Plasma Sciences CrC-150 Sputtering System (Torr International, Inc) before SEM analysis.

Sorting Procedure:

Several centrifugation steps, optimizing time and rotation rate of each step, were performed to separate the PLGA/pSi microspheres from the empty PLGA microspheres. Separation was carried out by three centrifugation steps of 10 min each at 500, 1200 and 4500 rpm respectively with the Allegra X-22 Centrifuge (Beckman Coulter Inc.). pSi particles conjugated with DyLight 549 NHS-Ester (Thermo Scientific) coated with PLGA were analyzed by FACS (Becton Dickinson, FACSCalibur) before and after sorting procedure to assess sorting efficiency.

Evaluation of FITC-BSA In Vitro Release:

$2 \times 10^7$ FITC-BSA loaded PLGA/pSi microspheres were dispersed in PBS (1 ml) at 37° C. At predetermined time intervals, the suspension was centrifuged (4500 rpm; 5 min), and the supernatant (1 ml) was collected, and replaced with fresh PBS (1 ml). The amount of BSA released was determined by analysis of the collected supernatant using a spectrophotometer at 493/518 nm. The suspension was also analyzed by FACS and the samples were prepared by mixing NaCl solution (150 μl) with suspension (5 μl) removed from in vitro release samples.

Degradation Studies:

The in vitro degradation of the PLGA/pSi microspheres was investigated by monitoring the surface morphology of the microspheres and the pH of the degradation media. The pH level was monitored using a pH meter (Denver Instrument UB-10), and the surface morphology of the microspheres was examined by SEM.

BSA Stability Studies:

SDS-PAGE gel electrophoresis was performed to determine the hydrolysis of BSA during the FITC-BSA release from PLGA/pSi. Color Silver Staining Kit was used to stain the gel, Mark 12 (Invitrogen) was used as standards. Supernatant (100 μl) released from PLGA/pSi microspheres (6%, 10%, 20%) collected on day 7 and day 14 was filtered by Amicon Ultra-0.5 ml centrifugal filter (Millipore Ultracel-3 Membrane, 3 kDa) before SDS-PAGE.

In Vitro Mineralization Studies:

The osteogenic media were prepared by base media (α-MEM media) (Invitrogen) containing Fetal bovine serum (20%, FBS) (Invitrogen) supplemented with L-glutamine (1%), sodium pyruvate (1%, Invitrogen), penicillin/streptomycin (1%, Invitrogen), and osteogenic supplement. PLGA/PSi microspheres were immersed in osteogenic growth medium. After 3, 8 and 21 day incubation, the specimens were washed carefully with DI water, and dried under vacuum overnight before characterization. PLGA microspheres were used as control. The samples were analyzed by SEM coupled with energy dispersive x-ray (EDX) for mineralization studies.

In Vitro Internalization Studies:

6,500 BMSCs were seeded into a 4 chamber tissue culture treated glass slides. When the cells were 30% confluent, PLGA/pSi microspheres containing 65,000 pSi particles were added into each chamber. 65,000 pSi particles were used as control. After 0 h, 24 h, 48 h, and 120 h incubation, cells were washed with PBS and fixed with 4% paraformaldehyde (PFA) for 10 min at room temperature. PFA was removed and washed twice with PBS. Cells were permeabilized with 0.1% Triton X for 10 min, and then blocked with BSA (1%) in PBS for 30 min at room temperature. Triton X was removed, and cells were incubated with Alexa Fluor 555 conjugated phalloidin in BSA (1%) in PBS for 30 min Cells were washed and incubated with DRAQ5 for 1 h. DRAQ5 was removed and prolong gold was added on the slides to mount the sample.

In Vitro Cellular Uptake of FITC-BSA:

40,000 HUVEC were seeded and cultured on a glass coverslip in a 12 well plate with 500 million PLGA/pSi microspheres loaded with FITC-BSA in a transwell on top of the cells. The media were changed every 3 days. Cellular uptake of FITC-BSA released from the PLGA/pSi microspheres was observed by confocal microscopy staining cells with fluorescent phalloidin (actin filaments) and DRAQ5 (nuclei) after fixation (10% formaldehyde).

Confocal Microscopy Analysis:

Detection of the FITC-BSA loaded pSi particles was based on autofluorescence using 488 excitation laser and the cells were analyzed by using 561 and 632 excitation laser for pholloidin and DRAQ5 respectively. Images were acquired using a Leica MD 6000 upright confocal microscope equipped with a 63× oil immersion objective.

REFERENCES

[1] L. T. Canham, *Adv. Mater.* 1995, 7, 1033.
[2] A. H. Mayne, S. C. Bayliss, P. Barr, M. Tobin, L. D. Buckberry, *phys. status solidi A.* 2000, 182, 505.
[3] M. A. Whitehead, D. Fan, P. Mukherjee, G. R. Akkaraju, L. T. Canham, J. L. Coffer, *Tissue Engineering A.* 2008, 14, 195.
[4] M. A. Whitehead, D. Fan, G. R. Akkaraju, L. T. Canham, J. L. Coffer, *J. Biomed. Mater. Res. Part A.* 2007, 83A, 225.
[5] L. T. Canham, *Nanotechnology.* 2007, 18, 185704.
[6] F. J. Martin, K. Melnik, T West, J. Shapiro, M. Cohen, A. A. Boiarski, M. Ferrari, *Drugs in R&D.* 2005, 6, 71.
[7] G. A. Soon-Whatt, C. A. Yaw-Fui, L. R. Houa-Gong, L. Te-Neng, Y. S. Wing-Kwong, C. May, S. Somanesan, L. S. Li-Er, N. D. Chee-Eng, L. Beng-Choo, C. Stephen, C. Pierce Kah-Hoe, *Int. J. Radiat. Oncology. biol. phys.* 2007, 67, 786.
[8] E. J. Anglin, M. P. Schwartz, V. P. Ng, L. A. Perelman, M. J. Sailor, *Langmuir.* 2004, 20, 11264.
[9] A. B. Foraker, R. J. Walczak, M. H. Cohen, T. A. Boiarski, C. F. Grove, P. W. Swaan, *Pharm. Res.* 2003, 20, 110.
[10] C. A. Prestidge, T. J. Barnes, A. Mierczynska-Vasilev, W. Skinner, F. Peddie, C. Barnett, *phys. status solidi A.* 2007, 204, 3361.
[11] L. Vaccari, D. Canton, N. Zaffaroni, R. Villa, M. Tormen, E. di Fabrizio, *Microelectron. Eng.* 2006, 83, 1598.
[12] R. E. Serda, S. Ferrati, B. Godin, E. Tasciotti, X. Liu, M. Ferrari, *Nanoscale.* 2009, 1, 250.
[13] E. Tasciotti, B. Godin, J. O. Martinez, C. Chiappini, R. Bhavane, X. Liu, M. Ferrari. *Mol Imaging.* 2010, In press.
[14] E. Tasciotti, X. Liu, R. Bhavane, K. Plant, A. D. Leonard, B. K. Price, M. M. C. Cheng, P. Decuzzi, J. M. Tour, F. Robertson, M. Ferrari, *Nat. Nanotechnol.* 2008, 3, 151.
[15] J. S. Ananta, B. Godin, R. Sethi, L. Moriggi, X. Liu, R. E. Serda, R. Krishnamurthy, R. Muthupillai, R. D. Bolskar, L. Helm, M. Ferrari, L. J. Wilson, P. Decuzzi, *Nano Tech.* 2010, 5, 815.
[16] C. Chiappini, E. Tasciotti, J. R. Fakhoury, D. Fine, L. Pullan, Y. Wang, L. Fu, X. Liu, M. Ferrari, *ChemPhysChem,* 2010, 11, 1029.
[17] P. Decuzzi, B. Godin, T. Tanaka, S. Y. Lee, C. Chiappini, X. Liu, M. Ferrari, *J. Controlled Release.* 2010, 141, 320.
[18] R. E. Serda, A. Mack, M. Pulikkathara, A. M. Zaske, C. Chiappini, J. R. Fakhoury, D. Webb, B. Godin, J. L. Conyers, X. Liu, J. A. Bankson, M. Ferrari, *Small.* 2010, 6, 1.
[19] J. H. Park, L. Gu, G. von Maltzahn, E. Ruoslahti, S. N. Bhatia, M. J. Sailor, *Nat. Mater.* 2009, 8, 331.
[20] T. Tanaka, L. S. Mangala, P. E. Vivas-Mejia, R. Nieves-Alicea, A. P. Mann, E. Mora, H.-D. Han, M. M. K. Shahzad, X. Liu, R. Bhavane, J. Gu, J. R. Fakhoury, C. Chiappini, C. Lu, K. Matsuo, B. Godin, R. L. Stone, A. M. Nick, G. Lopez-Berestein, A. K. Sood, M. Ferrari, *Cancer Res.* 2010, 70, 3687.
[21] B. H. Woo, G. Jiang, Y. W. Jo, P. P. DeLuca, *Pharm. Res.* 2001, 18, 1600.
[22] M. van de Weert, W. E. Hennink, W. Jiskoot, *Pharm. Res.* 2000, 17, 1159.
[23] J. M. Chan, L. Zhang, K. P. Yuet, G. Liao, J. W. Rhee, R. Langer, O. C. Farokhzad, *Biomaterials.* 2009, 30, 1627.
[24] D. M. K. Jensen, D. Cun, M. J. Maltesen, S. Frokjaer, H. M. Nielsen, C. Foged, J. *Controlled Release.* 2010, 142, 138.
[25] B. C. Tang, M. Dawson, S. K. Lai, Y.-Y. Wang, J. S. Suk, M. Yang, P. Zeitlin, M. P. Boyle, J. Fu, J. Hanes, *Proc. Natl. Acad. Sci.* 2009, 106, 19268.
[26] W. J. E. M. Habraken, J. G. C. Wolke, A. G. Mikos, J. A. Jansen, *J. Biomater. Sci., Polym. Ed.* 2008, 19, 1171.
[27] W. Linhart, F. Peters, W. Lehmann, K. Schwarz, A. F. Schilling, M. Amling, J. M. Rueger, M. Epple, *J. Biomed. Mater. Res.* 2001, 54, 162.
[28] V. P. Torchilin, *Adv. Drug Delivery Rev.* 2006, 58, 1532.
[29] J. Salonen, A. M. Kaukonen, J. Hirvonen, V. Lehto, *J. Pharm. Sci.* 2008, 97, 632.
[30] D. Fan, G. R. Akkaraju, L. T. Canham, J. L. Coffer, *Nanoscale.* 2010, In press.
[31] J. Lee, S. Lee, S. Yu, J. Park, J. Choi, J. Kim, *Surface and Coatings Technol.* 2008, 20, 5757.
[32] D. C. J Eisinger, *Magnes Res.* 1993, 6, 247.
[33] D. M. Reffitt, N. Ogston, R. Jugdaohsingh, H. F. J. Cheung, B. A. J. Evans, R. P. H. Thompson, J. J. Powell, G. N. Hampson, *Bone.* 2003, 32, 127.
[34] A. J. Milligan, F. M. M. Morel. *Science,* 2002, 297, 1848.
[35] M. S. Bawa, V. S. Simpson, P. A. Miller, F. L. Allen, G. L. Etheridge, K. J. L'anglois, M. H. Grimes, U.S. Pat. No. 6,028,006, 2000.
[36] M. Das, T. Miyakawa, C. F. Fox, R. M. Pruss, A. Aharonov, H. R. Herschman, *Proc Natl Acad Sci USA.* 1977, 74, 2790.
[37] Y. Xiao, S. P. Forry, X. Gao, R. D. Holbrook, W. G. Telford, A. Tona, *Journal of Nanobiotechnology.* 2010, 8, 13.
[38] G. Sharma, D. T. Valenta, Y. Altman, S. Harvey, H. Xie, S. Mitragotri, J. W. Smith, *J controlled Release.* 2010, 147, 408.
[39] Y. J. Ma, H. C. Gu, *J Mater Sci Mater Med.* 2007, 18, 2145.
[40] R. A. Gemeinhart, D. Luo, W. M. Saltzman, *Biotechnology Progress.* 2005, 21, 532.
[41] H. A. Lucero, E. Kintsurashvili, M. E. Marketou, H. Gavras, *J. Biol. Chem.* 2010, 285, 5555.
[42] X. Huang, X. Meng, F. Tang, L. Li, D. Chen, H. Liu, Y. Zhang, J. Ren, *Nanotechnology.* 2008, 19, 5101.
[43] R. N. Jorissen, F. Walker, N. Pouliot, T. P. J. Garrett, C. W. Ward, A. W. Burgess, *Experimental Cell Research.* 2003, 284, 31.
[44] G. Carpenter, S. Cohen, *J. Cell. Biol.* 1976, 71, 159.
[45] L. Beguinot, R. M. Lyall, M. C. Willingham, I. Pastan, *Proc. Natl. Acad. Sci. USA.* 1984, 81, 2384.
[46] A. Sorkin, C. M. Waters, *Bioessays.* 1993, 15, 375.
[47] M. L. Ho, Y. C. Fu, G. J. Wang, H. T. Chen, J. K. Chang, T. H. Tsai, C. K. Wang, *J. Controlled Release.* 2008, 128, 142.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of treating a bone defect in a subject, wherein the method comprises:
    injecting into the site of the bone defect an injectable composition comprising:
        a biodegradable polymer matrix;
        at least one biodegradable reinforcing particle dispersed in the biodegradable polymer matrix,
            wherein the at least one biodegradable reinforcing particle is selected from the group consisting of porous oxide particles and porous semiconductor particles, and
            wherein the at least one biodegradable reinforcing particle provides mechanical stability to the biodegradable polymer matrix; and
        porogen particles dispersed in the biodegradable polymer matrix,
            wherein the porogen particles comprise at least one active agent, and
            wherein the at least one active agent is contained or encapsulated within the porogen particles;
    wherein a scaffold is formed in-situ from the composition in the body of the subject at the site of the bone defect,
        wherein the scaffold comprises at least the polymer matrix and the porogen particles, and
        wherein the porogen particles degrade on the scaffold to release the at least one active agent and form pores within the scaffold.

2. The method of claim 1, wherein the porogen particles comprise hydrogel porogen particles.

3. The method of claim 1, wherein the at least one active agent is selected from the group consisting of therapeutics, imaging agents, anti-inflammatory agents, antibiotics, proteins, platelet rich plasma, cells, degradation inducers of porous particles, and combinations thereof.

4. The method of claim 1, wherein the porogen particles contain at least one biodegradable porous particle within the porogen particles.

5. The method of claim 4, wherein the biodegradable porous particle facilitates or controls at least one of intracellular delivery of an active agent, bio-distribution of an active agent, stability of an active agent, and internalization of the porous particle by cells or organelles.

6. The method of claim 1, wherein the bone defect comprises a bone fracture.

7. The method of claim 1, wherein the subject is a human being.

8. The method of claim 1, wherein the bone defect is selected from bone fractures, maxillofacial defects, and craniofacial defects.

9. The method of claim 1, wherein the polymer matrix comprises an unsaturated biodegradable polymer.

10. The method of claim 1, wherein the polymer matrix is selected from collagen, alginate, gelatin, polycaprolactone, poly(lactic-co-glycolic acid) (PLGA), poly(propylene fumarate)(PPF) or poly(ε-caprolactone-fumarate).

11. The method of claim 9, wherein the unsaturated biodegradable polymer is poly(propylene fumarate) (PPF).

12. The method of claim 1, wherein the porogen particles comprise at least one natural or synthetic biodegradable particle.

13. The method of claim 1, wherein the porogen particles comprise poly(lactic-co-glycolic acid) (PLGA).

14. The method of claim 2, wherein the hydrogel porogen particles comprise at least one of alginates, fibrins, and gelatins.

15. The method of claim 2, wherein the hydrogel porogen particle comprises alginate.

16. The method of claim 1, wherein the porogen particles comprise at least one biocompatible vesicle.

17. The method of claim 16, wherein the biocompatible vesicle comprises at least one of a liposome or a micelle.

18. The method of claim 1, wherein the active agent comprises stem cells.

19. The method of claim 18, wherein the active agent comprises mesenchymal stem cells.

20. The method of claim 4, wherein the at least one biodegradable porous particle comprises a silicon porous particle.

21. The method of claim 4, wherein the at least one biodegradable porous particle comprises at least one active agent.

22. The method of claim 21, wherein the at least one active agent is selected from the group consisting of therapeutics, imaging agents, anti-inflammatory agents, antibiotics, proteins, platelet rich plasma, cells, degradation inducers of porous particles, and combinations thereof.

23. The method of claim 4, wherein a surface of the biodegradable porous particle is modified with a biodegradable polymer.

24. The method of claim 23, wherein the biodegradable polymer is agarose.

25. The method of claim 23, wherein the biodegradable polymer is poly(lactic-co-glycolic acid) (PLGA).

26. The method of claim 1, wherein the porogen particles in the composition are in solid form.

* * * * *

UNITED STATES PATENT AND TRADEMARK OFFICE
CERTIFICATE OF CORRECTION

PATENT NO. : 10,058,633 B2
APPLICATION NO. : 15/270324
DATED : August 28, 2018
INVENTOR(S) : Mauro Ferrari et al.

Page 1 of 1

It is certified that error appears in the above-identified patent and that said Letters Patent is hereby corrected as shown below:

On the Title Page

Item (71) Applicants should read:
--(71) Applicants: Mauro Ferrari, Houston, TX (US); Rachel Buchanan, Austin, TX (US); Christine Smid, Austin, TX (US); Ennio Tasciotti, Houston, TX (US); Matthew Murphy, Spring, TX (US); Enrica De Rosa, Pearland, TX (US)--

Item (72) Inventors should read:
--(72) Inventors: Mauro Ferrari, Houston, TX (US); Rachel Buchanan, Austin, TX (US); Christine Smid, Austin, TX (US); Ennio Tasciotti, Houston, TX (US); Matthew Murphy, Spring, TX (US); Enrica De Rosa, Pearland, TX (US)--

Signed and Sealed this
Twenty-seventh Day of January, 2026

John A. Squires
*Director of the United States Patent and Trademark Office*